United States Patent
Li et al.

(10) Patent No.: US 10,639,276 B2
(45) Date of Patent: May 5, 2020

(54) LIPOSOMES WITH GINSENOSIDE AS MEMBRANE MATERIAL AND PREPARATIONS AND USE THEREOF

(71) Applicant: SHANGHAI GINPOSOME PHARMATECH CO., LTD., Shanghai (CN)

(72) Inventors: Chong Li, Shanghai (CN); Yahua Wang, Shanghai (CN); Huaxing Zhan, Shanghai (CN)

(73) Assignee: Shanghai Ginposome Pharmatech Co., Ltd., Shanghai (CN)

( * ) Notice: Subject to any disclaimer, the term of this patent is extended or adjusted under 35 U.S.C. 154(b) by 0 days.

(21) Appl. No.: 15/300,688

(22) PCT Filed: Aug. 19, 2016

(86) PCT No.: PCT/CN2016/096005
§ 371 (c)(1),
(2) Date: Sep. 29, 2016

(87) PCT Pub. No.: WO2017/028811
PCT Pub. Date: Feb. 23, 2017

(65) Prior Publication Data
US 2017/0172920 A1    Jun. 22, 2017

(30) Foreign Application Priority Data

Aug. 19, 2015  (CN) .......................... 2015 1 0509404

(51) Int. Cl.
*A61K 9/127*    (2006.01)
*A61K 31/704*    (2006.01)
(Continued)

(52) U.S. Cl.
CPC ............ *A61K 9/127* (2013.01); *A61K 9/1272* (2013.01); *A61K 9/1277* (2013.01);
(Continued)

(58) Field of Classification Search
CPC ....................................... A61K 9/127
See application file for complete search history.

(56) References Cited

U.S. PATENT DOCUMENTS

2014/0220083 A1* 8/2014 Brito .................... A61K 9/1075
424/400

FOREIGN PATENT DOCUMENTS

CN    101530389 A  *  9/2009

OTHER PUBLICATIONS

Yu et al (International Journal of Pharmaceutics 450 (2013) 250-258).*
Tung et al (Arch Pharm Res vol. 34, No. 4, 681-685, 2011).*

* cited by examiner

Primary Examiner — Benjamin J Packard
(74) Attorney, Agent, or Firm — Weisun Rao; Venture Partner, LLC

(57) ABSTRACT

Among others, the present invention provides a blank liposome, preparation methods thereof, and a loaded liposome including the blank liposome and an active substance. The liposomes have a membrane comprising lipids and a ginsenoside of Formula I, and may further comprise a surfactant, a heat-sensitive excipient, a pH sensitive material, or an ion additive.

(Continued)

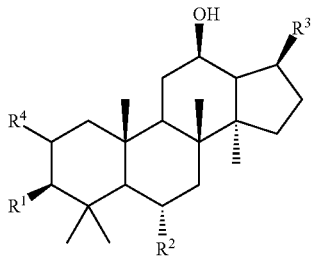
I
21 Claims, 26 Drawing Sheets
(51) Int. Cl.
A61K 31/337 (2006.01)
A61K 31/475 (2006.01)
A61K 31/513 (2006.01)
A61K 31/555 (2006.01)
A61K 31/7048 (2006.01)
A61K 31/713 (2006.01)
A61K 33/24 (2019.01)
A61K 31/57 (2006.01)
A61K 47/69 (2017.01)
(52) U.S. Cl.
CPC ........... *A61K 31/337* (2013.01); *A61K 31/475* (2013.01); *A61K 31/513* (2013.01); *A61K 31/555* (2013.01); *A61K 31/57* (2013.01); *A61K 31/704* (2013.01); *A61K 31/7048* (2013.01); *A61K 31/713* (2013.01); *A61K 33/24* (2013.01); *A61K 47/6911* (2017.08); *Y02A 50/463* (2018.01)

30-A      30-B      30-C

LIPOSOMES WITH GINSENOSIDE AS MEMBRANE MATERIAL AND PREPARATIONS AND USE THEREOF

CROSS-REFERENCE TO RELATED APPLICATIONS

This application is a U.S. national phase application of international application No. PCT/CN2016/096005, filed on Aug. 19, 2016, which claims priority to Chinese Patent Application No. 201510509404.8, filed on Aug. 19, 2015, the contents of which are incorporated herein by reference in their entireties.

BACKGROUND OF THE INVENTION

A liposome is a spherical vesicle having at least one lipid bilayer. It has been used as a targeted drug carrier and belongs to a new formulation of targeted drug delivery system. It can embed powder or solution of a drug in particle with a diameter at micron or nanometer level, the particle is similar to a bilayer micro vesicle of a biological membrane structure and has good biocompatibility. The reason for calling it targeted drug delivery system is, on one hand, after the surface-unmodified liposome enters a human body, it is usually susceptible to be phagocytized by the reticulo endothelial system, thereby activating the body's own immune function and changing the distribution of the embedded drug in the human body, which leads to the drug mainly accumulated in liver, spleen and other tissues and organs. Due to the enhanced permeability and retention effect of tumors (EPR effect), the liposome with a particle size at nanometer level can accumulate effectively at the tumor sites, this property can be called passive target of the liposome. On the other hand, the surface of the liposome can be modified by specific ligands in a covalent or non-covalent manner. The ligands include antibodies, polypeptides, aptamers, glycosyl and small molecules and so on. The liposome is efficiently absorbed by specific targeted cells through an interaction between ligands and receptors, which is called initiative target, often compared to "biological missile". The targeted drug delivery capability of the liposome can increase the therapeutic index of the drug, reduce the dosage and the toxicity of the drug.

A structure of the liposome is different from a micelle that is constructed by the surfactant. The latter is composed of a monomolecular layer, while the liposome is composed of bilayer which can embed a lipophilic drug or a water-soluble drug. The main components of the liposome are lipid (e.g., phospholipid) and cholesterol. Phospholipid is an amphiphilic material and contains phosphate groups and amino-containing basic groups (both hydrophilic), and two relatively long hydrophobic hydrocarbon chains. Cholesterol is an amphipathic material and has both a hydrophobic group and a hydrophilic group, but its hydrophobicity is stronger than its hydrophilicity. When the phospholipid forms a liposome, there are two hydrophobic chains pointing to the interior, the hydrophilic groups are on both inside and outside surfaces of the membrane. The phospholipid bilayer constitutes a closed compartment, which contains an aqueous solution. The aqueous solution in the compartment is surrounded by the phospholipid bilayer and independent, the phospholipid bilayer forms a vesicle and is separated by the aqueous medium. The cholesterol increases the stability of the liposome membrane, and other excipients have special functional effects.

The main components of a conventional liposome are phospholipid and cholesterol forming the liposome's membrane. The main components (except for the Taxol drug) of a paclitaxel liposome supplied by Cisco Nanjing (marketed as "Paclitaxel Liposome", herein also referred to simply as "paclitaxel") include lecithin (first main component), cholesterol (second main component), threonine (an amino acid generally used as an antioxidant or a buffer reagent), and glucose (glucide generally used as a freeze-dried excipient or a cryoprotectant). Other excipients can also be added into the liposome, such as adding a heat-sensitive excipient to prepare a heat-sensitive liposome, adding a pH-sensitive excipient to prepare a pH-sensitive liposome, adding a cation or an anion to prepare a cationic liposome or an anionic liposome, or adding a surfactant etc. According to different purposes, different excipients are added. Generally, the liposome before frozen dried has the phospholipid (generally with a proportion of 50% to 95%) and the cholesterol (about 5% to 50%) as main components, but during the process of freeze-drying, a certain amount of excipient will be added according to the specific conditions. Depending on different uses of the liposome, the proportion of the added excipient is greatly different. Some do not need to add excipients during freeze-drying, while some even require an addition of 50% excipients during freeze-drying. In addition, there are many modified phospholipids in the market at present, such as phospholipid modified by PEG or amino acid, which contains very small amounts of excipients. Therefore, mutual reference does not have significant meaning between liposomes with different uses and in different types since the specific components and the amount of each component are greatly different (Note: the percentage mentioned above refers to a percentage of each component relative to the total mass of the raw materials of the liposome).

There are corresponding technical requirements for preparation due to differences in physical and chemical properties of different types of drugs, such as structure, solubility, stability and so on. Meanwhile, it is necessary to continue improving technology, membrane materials, pilot scaling and other aspects. There are eight main indicators to evaluate the quality of liposomes, including morphology and particle size of liposomes (including dispersion), encapsulation efficiency, drug loading, burst and permeability, release in vitro, oxidation degree of the phospholipids, residual of organic solvent and functional evaluation in vivo and in vitro. But over all, the present liposomes still have shortcomings such as that the target-specific ability needs to be further improved, encapsulation efficiency is low, stability is poor and the process for preparation is complicated etc.

Therefore, it is always a key point and direction of the liposome to research a liposome with high efficiency, safety, stability, enhanced targetability, good uniformity, stable and reliable quality, and simple process for preparation.

Ginsenoside is a material having special amphipathic property with a glycosyl in the hydrophilic end and a long terminal chain in the lipophilic end. Ginsenoside has wide pharmaceutical uses, for example that ginsenoside F4 and Rg6 are used for treating lymphoma, ginsenoside Rg3 is used for treating dysmenorrhea and vitiligo, ginsenoside Rh1 can be used to improve steroid resistant induced by using dexamethasone and increase the anti-inflammatory effect of the dexamethasone, the ginsenoside Rb1 can be used to prevent and treat hypertension (see CN201310165926, CN201310165907, CN201210501652, CN201310011400 and CN201210486959). CN201210151597.0 discloses a liposome of ginsenoside Rg3 and its preparation method. The liposome of ginsenoside Rg3 is obtained by encapsulating the drug ginsenoside Rg3 into a liposome, which significantly increases the absorption and bioavailability of ginsenoside Rg3 and enhances its targetability to the tumor tissues, therefore, improves the drug efficacy.

In the prior art, there is no report on that the ginsenoside, as a liposome membrane material and meanwhile a targeted material and a drug, can be used to prepare a blank liposome and encapsulate drugs and other components.

BRIEF SUMMARY OF THE INVENTION

To overcome the disadvantages of the current liposome technology, such as low encapsulation efficiency, poor stability, complicated preparation process and the targetability which needs to be further improved, the present invention, among others, provides blank liposomes with ginsenoside as membrane material, preparation methods therefor, uses thereof, and loaded liposomes containing active substances and the blank liposomes of this invention. The blank liposomes of the present invention have the advantages of high efficiency, safety, stability, enhanced targetability, good uniformity, stable and reliable quality, and convenient preparation processes. They can be used to encapsulate drugs, cosmetically active substances, or substances with healthcare function to form a liposome loaded with active substances. When a blank liposome of the present invention is used to encapsulate such active substances, e.g., antitumor drugs, the loaded liposome thus prepared exhibited unexpectedly much better targeting effect on tumor cells, anti-multi-drug resistance effect, synergism effect, attenuation effect and drug synergism. Specifically, when compared to the ordinary liposomes, this liposome of the present invention has much more excellent indicators, especially as candidates for loading drugs and as drug carriers, targetability, anti-multi-drug resistance, synergism and attenuation and drug synergism etc.

In some aspect, the present invention provides a blank liposome having a membrane, wherein the membrane comprises lipid and a ginsenoside of Formula I:

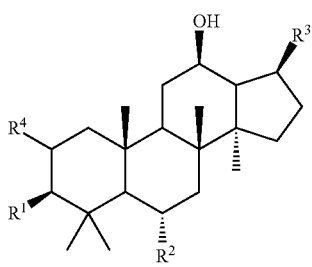

In Formula I,
each of $R^1$ and $R^2$ independently is H, OH, or $R^5$, and $R^1$ and $R^2$ are not both H at the same time;
$R^3$ is

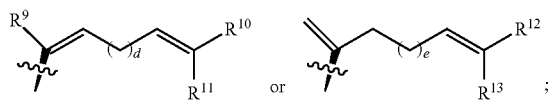

$R^4$ is H, OH, or $R^5$;
$R^5$ is $R^6$, $R^7$, or $R^8$;
$R^6$ is selected from the group consisting of: —O-Glc, —O-Rha, —O-Lyx, —O-Xyl, —O-Ara(p), —O-Ara(f), —O-Glc(2→1)Glc, —O-Glc(6→1)Glc, —O-Glc(2→1)Rha, —O-Glc(2→1)Xyl, —O-Glc(6→1)Xyl, —O-Glc(6→1)Rha, —O-Glc(2→1)Ara(p), —O-Glc(6→1)Ara(p), —O-Glc(2→1)Ara(f), —O-Glc(6→1)Ara(f), —O-Glc(2→1)Glc(2→1)Glc, —O-Glc(2→1)Glc(2→1)Xyl, —O-Glc(6→1)Glc(6→1)Xyl, —O-Glc(2→1)Glc(4→1)Xyl, —O-Glc(2→1)Lyx, —O-Glc(6→1)Lyx, —O-Glc(2→1)Glc(2→1)Rha, —O-Glc(2→1)Glc(2→1)Lyx, —O-Glc(2→1)Glc(2→1)Ara(f), —O-Glc(2→1)Glc(2→1)Ara(p), —O-Glc(2→1)Glc(6→1)Glc, —O-Glc(2→1)Glc(6→1)Rha, —O-Glc(2→1)Glc(6→1)Xyl, —O-Glc(2→1)Glc(6→1)Lyx, —O-Glc(2→1)Glc(6→1)Ara(f), —O-Glc(2→1)Glc(6→1)Ara(p), —O-Glc(6→1)Glc(2→1)Glc, —O-Glc(6→1)Glc(2→1)Rha, —O-Glc(6→1)Glc(2→1)Xyl, —O-Glc(6→1)Glc(2→1)Lyx, —O-Glc(6→1)Glc(2→1)Ara(f), —O-Glc(6→1)Glc(2→1)Ara(p), —O-Glc(6→1)Glc(6→1)Glc, —O-Glc(6→1)Glc(6→1)Rha, —O-Glc(6→1)Glc(6→1)Lyx, —O-Glc(6→1)Glc(6→1)Ara(f) or —O-Glc(6→1)Glc(6→1)Ara(p);
$R^7$ is a group formed by replacing one or more than one OH groups in $R^6$ with $R^8$ and each of the one or more than one $R^8$ groups independently can be the same as or different from each other;
$R^8$ is:
I) -mPEG, -Z-mPEG, -mPEO, -Z-PEO, -mPVP, -Z-PVP, -mEPEG, or -Z-EPEG, wherein m is H, alkyl, or acyl; Z is —CO(CH$_2$)$_a$CO—, —NH(CH$_2$)$_a$CO—, —NH(CH$_2$)$_b$X—, or —CO—Ar—CH$_2$—; X is O, S, or NH; a is 1, 2, 3, 4, 5, 6, 7, or 8; and b is 1, 2, 3, 4, 5, 6, 7, 8, 9, or 10; or
II) $C_{4-22}$ aliphatic acyl, a phosphate group, a succinic acid ester group, a n-butyl acid ester group, a sulfonate group, a malic acid ester group, or a sodium sulfate salt; or
III) a group formed by dehydrogenizing the carboxyl contained in Boc-glycine, Boc-alanine, Boc-arginine, Boc-lysine, Boc-serine, Acetyl phenylalanine, Acetyl-proline, Asparagine, Aspartic acid, Cysteine, Glutamine, Glutamic acid, Histidine, Isoleucine, Leucine, Methionine, Phenylalanine, Proline, Threonine, Tryptophan, Tyrosine, or Valine; or
IV) —O-PEO, —O-PVP, —O-PEG, —O-MPEG, —O-EPEG, —O-Glc (2→1)Glc(6→1)Mal or —O-Glc (2→1)Glc(6→1)Ac;
each of $R^9$, $R^{10}$, $R^{11}$, $R^{12}$ and $R^{13}$, independently, is $C_{1-3}$ alkyl;
each of d and e, independently, is 1, 2, or 3; and
the ginsenoside of Formula I can be optionally modified by replacing one or more OH groups therein with one or more $R^8$ groups, and each of the $R^8$ replacement groups (when 2 or more) independently can be the same as or different from each other.

As used herein, in a group such as —O-Glc(2→1)Glc, the numbers indicating carbon position, and the arrow → indicates the connection relationship; Glc refers to glucopyranosyl; Xyl refers to xylopyranosyl; Rha refers to rhamnopyranosyl; Ara(p) refers to arabinopyranosyl; Ara(f) refers to arabinofuranosyl; Lyx is lyxosyl; Ar refers to aryl; Mal refers to a malonyl; Ac refers to an acetyl; PEG refers to polyethylene glycol; PEO refers to polyoxyethylene or polyethylene oxide; MPEG refers to monomethoxy-terminated polyethylene glycol; EPEG refers to epoxy-terminated polyethylene glycol; PVP refers to povidone.

In —O-Glc- group, the structure of Glc is:

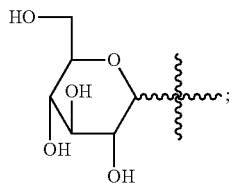

in —O-Ara(p) group, the structure of Ara(p) is:

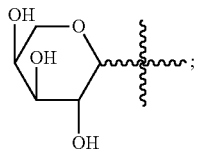

in —O-Lyx group, the structure of Lyx is:

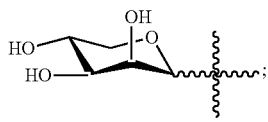

in —O-Ara(f) group, the structure of Ara(f) is:

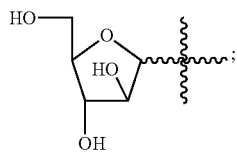

in —O-Rha group, the structure of Rha is:

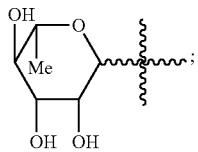

in —O-Xyl group, the structure of Xyl is:

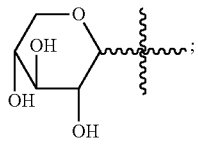

the structure of Mal is:

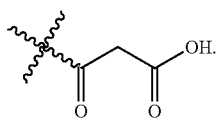

In some embodiments, the molecular weight of PEG, PEO, PVP, or EPEG is independently in the range of 200 to 20,000.

In some embodiments, the aliphatic acyl group can be an acyl of a natural saturated or unsaturated aliphatic acid, and an acyl of artificially synthesized saturated or unsaturated aliphatic acid, preferably a stearyl or a palmityl.

$R^3$ is preferably

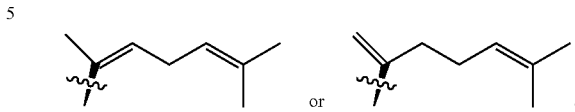

In the blank liposome, the ginsenoside of Formula I can be ginsenoside Rg5, ginsenoside Rg6, ginsenoside Rk1, ginsenoside Rk2, ginsenoside Rk3, ginsenoside Rk4, ginsenoside Rh3, ginsenoside Rh4, ginsenoside F4, ginsenoside Rs4, ginsenoside Rs5, ginsenoside Rs6, ginsenoside Rs7, notoginsenoside T5, damulin A, or damulin B.

As mentioned above, the ginsenoside of Formula I contained in the blank liposome of the present invention can be modified by replacing one or more hydroxyl (OH) groups in the ginsenoside with $R^8$, and each of $R^8$ groups (when more than one) can be the same as or different from each other, and $R^8$ is as defined above.

In the blank liposome of the present invention, the HPLC purity of the ginsenoside (including that as modified as described above) is preferably greater than or equal to 90%, more preferably greater than 95%, where the percentage is mass percentage.

Preferably, in the blank liposome, the ginsenoside of Formula I can also be in the form of micelle. Ginsenoside nano micelle refers to that the ginsenoside is in the form of micelle, specifically refers to CN Patent Application CN201310155639.2 filed on Apr. 28, 2013 and PCT Application PCT/CN2013/088558 filed on Dec. 4, 2013, which are hereby incorporated herein by reference in their entireties.

Preferably, in the blank liposome of the present invention, the lipid in the membrane comprises phospholipid; and the mass ratio of the phospholipid to the ginsenoside of Formula I is usually in the range of 0.5:1 to 100:1, preferably in the range of 0.5:1 to 20:1, more preferably in the range of 0.5:1 to 4:1 (such as in the range of 0.5:1 to 2:1).

Preferably, in the blank liposome of the present invention, the lipid in the membrane comprises phospholipid; the membrane further comprises cholesterol. The mass ratio of the phospholipid to the ginsenoside of Formula I is preferably in the range of 1:0.01 to 1:3 (such as in the range of 1:0.03 to 1:1), more preferably in the range of 1:0.05 to 1:0.9 (such as in the range of 1:0.3 to 1:0.75), most preferably in the range of 1:0.1 to 1:0.9 (such as in the range of 1:0.1 to 1:0.5). The mass ratio of the ginsenoside of Formula I to the cholesterol is preferably in the range of 0.1:1 to 100:1, preferably in the range of 0.5:1 to 50:1, more preferably in the range of 0.5:1 to 10:1 (such as in the range of 1.5:1 to 6:1, or 5:1).

In the blank liposome of the present invention, a mass percentage of the ginsenoside of Formula I in the membrane is preferably in the range of 0.01% to 80%, a mass percentage of the phospholipid in the membrane is preferably in the range of 5% to 99.9%, a mass percentage of the cholesterol in the membrane is preferably lower than 50%; the percentage (%) mentioned above refers to the percentage of the mass of each component relative to the total mass of the membrane.

The mass percentage of the ginsenoside of Formula I in the membrane is preferably in the range of 10% to 80%, more preferably in the range of 10% to 40%, most preferably in the range of 20% to 40% (such as in the range of 25% to 40%, preferably in the range of 25% to 35%). The mass percentage of the phospholipid in the membrane is preferably in the range of 10% to 70%, more preferably in the range of 30% to 70%, most preferably in the range of 30% to 60%. The mass percentage of the cholesterol in the membrane is preferably in the range of 0.5% to 50%, more preferably in the range of 5% to 40%, most preferably in the range of 5% to 30% (such as in the range of 10% to 20%).

In a preferred embodiment of the present invention, the blank liposome can further comprise and encapsulate within the membrane an antioxidant. A mass percentage of the antioxidant in the blank liposome is usually no more than 25%, preferably in the range of 0.001% to 15%, more preferably in the range of 0.01% to 10%, most preferably in the range of 0.01% to 5% (such as in the range of 0.1% to 1%), the percentage (%) refers to the percentage of the mass of the antioxidant relative to the total mass of the blank liposome.

In a preferred embodiment of the present invention, the blank liposome can further comprise and encapsulate within the membrane a cryoprotectant. A mass percentage of the cryoprotectant in the blank liposome is usually no more than 80%, preferably in the range of 0.5% to 60%, more preferably in the range of 5% to 60%, most preferably in the range of 30% to 60%, the percentage (%) refers to the percentage of the mass of the cryoprotectant relative to the total mass of the blank liposome.

In a preferred embodiment of the present invention, the blank liposome can further comprise and encapsulate within the membrane soybean oil and/or sodium oleate. A mass percentage of the "soybean oil and/or sodium oleate" in the blank liposome is usually in the range of 1% to 90%, preferably in the range of 15% to 80%, more preferably in the range of 20% to 70% (such as in the range of 25% or 62.5%), most preferably in the range of 20% to 30%, or 60% to 70%, the percentage refers to the mass of the "soybean oil and/or sodium oleate" relative to the total mass of the blank liposome. A mass ratio of the "soybean oil and/or sodium oleate" to the phospholipid in the blank liposome is preferably in the range of 1:0.1 to 1:10, more preferably in the range of 1:0.5 to 1:5, most preferably in the range of 1:0.5 to 1:4 (such as in the range of 1:1 to 1:2).

In a preferred embodiment of the present invention, the blank liposome comprises the following components: phospholipid and the ginsenoside of Formula I, or the ginsenoside of Formula I, phospholipid and an antioxidant, or the ginsenoside of Formula I, phospholipid and a cryoprotectant, or the ginsenoside of Formula I, "soybean oil and/or sodium oleate" and phospholipid, or the ginsenoside of Formula I, "soybean oil and/or sodium oleate", phospholipid and an antioxidant, or the ginsenoside of Formula I, "soybean oil and/or sodium oleate", phospholipid and a cryoprotectant, or the ginsenoside of Formula I, "soybean oil and/or sodium oleate", phospholipid, an antioxidant and a cryoprotectant, or the ginsenoside of Formula I, phospholipid and cholesterol, or the ginsenoside of Formula I, phospholipid, cholesterol and an antioxidant, or the ginsenoside of Formula I, phospholipid, cholesterol and a cryoprotectant, or the ginsenoside of Formula I, "soybean oil and/or sodium oleate", phospholipid and cholesterol, or the ginsenoside of Formula I, "soybean oil and/or sodium oleate", phospholipid, cholesterol and an antioxidant, or the ginsenoside of Formula I, "soybean oil and/or sodium oleate", phospholipid, cholesterol and a cryoprotectant, or the ginsenoside of Formula I, "soybean oil and/or sodium oleate", phospholipid, cholesterol, an antioxidant and a cryoprotectant.

In a preferred embodiment of the present invention, the blank liposome consists of the components mentioned above.

In a preferred embodiment of the present invention, the blank liposome comprises the following components: the ginsenoside of Formula I, the phospholipid, the cholesterol, the soybean oil and/or the sodium oleate, the antioxidant and the cryoprotectant. The mass ratio of the soybean oil and/or the sodium oleate to the cholesterol in the blank liposome is preferably in the range of 1:0.1 to 1:10, more preferably in the range of 1:0.5 to 1:5, most preferably in the range of 1:0.5 to 1:1. A mass percentage of the cholesterol in the membrane is preferably in the range of 1% to 20%, more preferably in the range of 10% to 20%, a mass percentage of the soybean oil and/or the sodium oleate in the blank liposome is preferably in the range of 1% to 90%, more preferably in the range of 15% to 80%, most preferably in the range of 20% to 70% (such as in the range of 25% or 62.5%, 20% to 30%, or 60% to 70%).

In a preferred embodiment of the present invention, the blank liposome consists of the phospholipid and the ginsenoside of Formula I.

In a preferred embodiment of the present invention, the blank liposome consists of the ginsenoside of Formula I, the phospholipid and the cholesterol.

In a preferred embodiment of the present invention, the blank liposome consists of the ginsenoside of Formula I, the phospholipid, the cholesterol, the antioxidant and the cryoprotectant.

In a preferred embodiment of the present invention, the blank liposome consists of the ginsenoside of Formula I, the phospholipid, the cholesterol, the soybean oil and/or sodium oleate, the antioxidant and the cryoprotectant.

The phospholipid can be a conventional phospholipid in this field, preferably comprises a natural phospholipid, semisynthetic phospholipid or fully synthetic phospholipid.

The natural phospholipid is typically derived from soybean, yolk, brain or organs of an animal, preferably comprises natural lecithin, soybean lecithin egg lecithin or cephalin.

The semisynthetic phospholipid or the fully synthetic phospholipid can be a conventional semisynthetic phospholipid or fully synthetic phospholipid in this field, preferably comprises a phospholipid of phosphatidylcholines, phosphatidylserine (PS), phosphatidylinositol (PI), a phospholipid of phosphatidylethanolamine, phosphatidylglycerol (DSPG), dicetyl phosphate (DCP), a PEG-modified phospholipid, cholesterol succinate (CHS) or 1-palmitoyl-2-oleoyl-sn-glycero-3-phosphocholine (16:0 to 18:1 PC, wherein 16:0 to 18:1 refers to the carbon chain of PC). Due to the heat-sensitivity of the semisynthetic or fully synthetic phospholipids such as dipalmitoyl phosphatidylcholine and distearoyl phosphatidylcholine etc., they can be used as heat-sensitive excipients at the same time.

The phospholipid of phosphatidylcholline can be a conventional phospholipid of phosphatidylcholline in this field, preferably comprises hydrogenated soybean lecithin (HSPC), dipalmitoyl phosphatidylcholine (DPPC), distearoyl phosphatidylcholine (DSPC), dimyristoyl phosphatidylcholine (DMPC), dilauroyl phosphatidylcholine (DLPC), dioleoyl phosphatidylcholine (DOPC), phosphatidylcholine (SPC), monopalmitoyl phosphatidylcholine (MPPC) or glycerol phosphatidylcholine (GPC).

The phospholipid of phosphatidylethanolamine can be a conventional phospholipid of phosphatidylcholline in this field, preferably comprises 1-palmitoyl-2-oleoyl phosphatidylethanolamine (POPE), dilauroyl phosphatidylethanolamine (DLPE), dierucoyl phosphatidylethanolamine (DEPE), dioleoyl phosphatidylethanolamine (DOPE), distearoyl phosphatidylethanolamine (DSPE), dipalmitoyl phosphatidylethanolamine (DPPE) or dimyristoyl phosphatidylethanolamine (DMPE).

The PEG-modified phospholipid can be a conventional PEG-modified phospholipid in this field, preferably comprises phosphatidylethanolamine-PEG (DMPE-PEG), dipalmitoyl phosphatidylethanolamine-PEG (DPPE-PEG), distearoyl phosphatidylethanolamine-PEG (DSPE-PEG), dioleoyl phosphatidylethanolamine-PEG (DOPE-PEG), C8 ceramide-PEG (C8 ceramide-PEG), C16 ceramide-PEG (C16 ceramide-PEG), distearoyl phosphatidylethanolamine-PEG-succinyl (DSPE-PEG succinyl), distearoyl phosphatidylethanolamine-PEG-carboxyl (DSPE-PEG carboxylic acid), distearoyl phosphatidylethanolamine-PEG-maleimide (DSPE-PEG maleimide), distearoyl phosphatidylethanolamine-PEG-propionamide bis-mercaptopyridine (DSPE-PEG PDP), distearoyl phosphatidylethanolamine-PEG-cyanuric chloride (DSPE-PEG cyanur), distearoyl phosphatidylethanolamine-PEG-amino (DSPE-PEG amine), distearoyl phosphatidylethanolamine-PEG-biotin (DSPE-PEG biotin), distearoyl phosphatidylethanolamine-PEG-folate (DSPE-PEG folate), distearoyl phosphatidylethanolamine-PEG-folate (DSPE-PEG folate), dilauroyl phosphatidylethanolamine-PEG (DLPE-PEG), distearoyl phosphatidylethanolamine-PEG-active ester (DSPE-PEG-NHS), phosphatidylethanolamine-PEG-active ester (DMPE-PEG-NHS), dipalmitoyl phosphatidylethanolamine-PEG-active ester (DPPE-PEG-NHS), dilauroyl phosphatidylethanolamine-PEG-active ester (DLPE-PEG-NHS), distearoyl phosphatidylethanolamine-PEG-maleimide (DSPE-PEG-maleimide), phosphatidylethanolamine-PEG-maleimide (DMPE-PEG-maleimide), dipalmitoyl phosphatidylethanolamine-PEG-maleimide (DPPE-PEG-maleimide), dilauroyl phosphatidylethanolamine-PEG-maleimide (DLPE-PEG-maleimide), distearoyl phosphatidylethanolamine-PEG-biotin (DSPE-PEG-biotin), distearoyl phosphatidylethanolamine-PEG-fluorescein (DSPE-PEG-FITC), distearoyl phosphatidylethanolamine-PEG-hydroxyl (DSPE-PEG-OH), distearoyl phosphatidylethanolamine-PEG-amino (DSPE-PEG-NH2), phosphatidylethanolamine-PEG-amino (DMPE-PEG-NH2), dipalmitoyl phosphatidylethanolamine-PEG-amino (DPPE-PEG-NH2), dilauroyl phosphatidylethanolamine-PEG-amino(DLPE-PEG-NH2), distearoyl phosphatidylethanolamine-PEG-carboxyl (DSPE-PEG-COOH), phosphatidylethanolamine-PEG-carboxyl (DMPE-PEG-COOH), dipalmitoyl phosphatidylethanolamine-PEG-carboxyl (DPPE-PEG-COOH), dilauroyl phosphatidylethanolamine-PEG-carboxyl (DLPE-PEG-COOH), distearoyl phosphatidylethanolamine-PEG-thiol (DSPE-PEG-SH), distearoyl phosphatidylethanolamine-PEG-silane (DSPE-PEG-silane), distearoyl phosphatidylethanolamine-PEG-azide (DSPE-PEG-N3), cholesterol-PEG (cholesterol PEG), methoxyl-PEG-cholesterol (mPEG-CLS), cholesterol-PEG-active ester (cholesterol PEG NHS ester), cholesterol-PEG-maleimide (CLS-PEG-Mal), cholesterol-PEG-biotin (cholesterol PEG biotin), cholesterol-PEG-fluorescein (cholesterol PEG fluorescein), cholesterol-PEG-carboxyl (cholesterol PEG COOH), cholesterol-PEG-amino (cholesterol PEG NH2) or cholesterol-PEG-thiol (Cholesterol PEG SH). The relative molecular weight of the PEG mentioned above is preferably in the range of 300 to 50000, more preferably in the range of 500 to 10000, e g. at about 300, 350, 500, 550, 1000, 2000, 3400, 5000, 10000, 20000, 30000, 40000 or 50000.

A number-average molecular weight of the DMPE-PEG is preferably 350, 550, 750, 1000, 2000, 3000 or 5000. A number-average molecular weight of the DPPE-PEG is preferably 350, 550, 750, 1000, 2000, 3000 or 5000. A number-average molecular weight of the DSPE-PEG is preferably 350, 550, 750, 1000, 2000, 3000, 5000, 10000, 20000, 30000 or 40000. A number-average molecular weight of the DOPE-PEG is preferably 350, 550, 750, 1000, 2000, 3000 or 5000. A number-average molecular weight of the C8 Ceramide-PEG is preferably 750, 2000 or 5000. A number-average molecular weight of the DLPE-PEG is preferably 2000 or 5000. A number-average molecular weight of the DSPE-PEG-NHS is preferably 1000, 2000, 5000, 10000, 20000, 30000 or 40000. A number-average molecular weight of the DMPE-PEG-NHS is preferably 3400 or 5000. A number-average molecular weight of the DPPE-PEG-NHS is preferably 3400 or 5000. A number-average molecular weight of the DLPE-PEG-NHS is preferably 3400 or 5000. A number-average molecular weight of the DSPE-PEG-Maleimide is preferably 1000, 2000, 3400, 5000 or 10000. A number average-molecular weight of the DMPE-PEG-Maleimide is preferably 1000, 2000, 3400, 5000 or 10000. A number-average molecular weight of the DPPE-PEG-Maleimide is preferably 1000, 2000, 3400, 5000 or 10000. A number-average molecular weight of the DLPE-PEG-Maleimid is preferably 1000, 2000, 3400, 5000 or 10000. A number-average molecular weight of the DSPE-PEG-Biotin is preferably 1000, 2000, 3400, 5000 or 10000. A number-average molecular weight of the DSPE-PEG-FITC is preferably 1000, 2000, 3400, 5000 or 10000. A number-average molecular weight of the DSPE-PEG-OH is preferably 2000, 3400 or 5000. A number-average molecular weight of the DSPE-PEG-NH2 is preferably 2000, 3400 or 5000. A number-average molecular weight of the DMPE-PEG-NH2 is preferably 2000, 3400 or 5000. A number-average molecular weight of the DPPE-PEG-NH2 is preferably 2000, 3400 or 5000. A number-average molecular weight of the DLPE-PEG-NH2 is preferably 2000, 3400 or 5000. A number-average molecular weight of the DSPE-PEG-COOH is preferably 2000, 3400 or 5000. A number-average molecular weight of the DMPE-PEG-COOH is preferably 2000, 3400 or 5000. A number-average molecular weight of the DPPE-PEG-COOH is preferably 2000, 3400 or 5000. A number-average molecular weight of the DLPE-PEG-COOH is preferably 2000, 3400 or 5000. A number-average molecular weight of the DSPE-PEG-SH is preferably 5000. A number-average molecular weight of the DSPE-PEG-Silane is preferably 3400. A number-average molecular weight of the DSPE-PEG-N3 is preferably 2000, 3400 or 5000. A number-average molecular weight of the mPEG-CLS is preferably 1000, 2000, 5000, 10000 or 20000. A number-average molecular weight of the Cholesterol PEG NHS ester is preferably 1000, 2000, 3400, 5000 or 10000. A number-average molecular weight of the CLS-PEG-Mal is preferably 2000, 3400, 5000 or 10000. A number-average molecular weight of the CLS-PEG-Biotin is preferably 2000, 3400 or 5000. A number-average molecular weight of the CLS-PEG-FITC is preferably 2000, 3400 or 5000. A number-average molecular weight of the Cholesterol PEG COOH is preferably 3400. A number-average molecular weight of the Cholesterol PEG amine is preferably 3400. A number-average molecular weight of the Cholesterol PEG Thiol/Sulfhydril is preferably 3400.

The antioxidant can be a conventional antioxidant in this field, preferably comprises sodium metabisulfite, sodium thiosulfate, propyl gallate, ascorbic acid, α-tocopherol, α-hydroxyl acid, flavonoid, a phenylpropanoid phenolic compounds, vitamin E, vitamin C, fumaric acid, cysteine, methionine, butyl hydroxy anisole (BHA), butyl hydroxytoluene (BHT), thiodipropionic acid, sulfites (e.g., sodium sulfite), hydrosulphite (e.g., sodium hydrosulfite), dithioaminobenzoic acid compounds, citric acid, malic acid, sorbitol, glycerol, propylene glycol, hydroquinone, hydroxycoumarin, ethanolamine, phosphoric acid or phosphorous acid.

The cryoprotectant can be a conventional cryoprotectant in this field, generally comprises a glucide, a polyol, an amino acid or a buffer reagent; wherein the glucide preferably comprises a monosaccharide, a disaccharide or a polysaccharide. The monosaccharide preferably comprises glucose, mannitol, xylitol or sorbitol. The disaccharide preferably comprises sucrose, lactose, galactose or maltose. The polysaccharide preferably comprises trehalose. The polyol preferably comprises mannitol, sorbitol or glycerol. The amino acid preferably comprises α-amino acid selected from the group consisting of threonine, glycine, glutamic acid, arginine and histidine. The buffer reagent generally refers to a buffer solution. The buffer solution can be a conventional buffer solution in this field, whose pH value is preferably in the range of 3 to 10, more preferably in the range of 5 to 7. The buffer solution preferably comprises an ethanol-acetic acid buffer solution, a tris (hydroxymethyl) aminomethane buffer solution, a barbital buffer solution, a sodium formate buffer solution, a phthalate buffer solution, a citrate buffer solution, a citric acid-disodium hydrogen phosphate buffer solution, an ammonia-ammonium chloride buffer solution, a borax-calcium chloride buffer solution, an acetate buffer solution, an acetic acid-lithium salt buffer solution, an acetic acid-sodium acetate buffer solution, an acetic acid-ammonium acetate buffer solution, a phosphoric acid-triethylamine buffer solution or a phosphate buffer solution.

Preferably, the blank liposome can further comprise and encapsulate within the membrane other excipients. The excipients can be conventional excipients used for preparing liposome in this field except for the antioxidant and the cryoprotectant, such as the excipient comprise a surfactant, a heat-sensitive excipient, a pH-sensitive material or an ion additive.

The surfactant preferably comprises polyethylene glycol (PEG), polysorbate, Tween surfactant, or a brij surfactant. Wherein a number-average molecular weight of the polyethylene glycol is preferably in the range of 200 to 8000 (e g. at about 300, 350, 500, 550, 1000, 2000, 3400 or 5000). The polysorbate preferably comprises polyoxyethylene sorbitan monolaurate, polyoxyethylene sorbitan monopalmitate, polyoxyethylene sorbitan monostearate, polyoxyethylene sorbitan trioleate, PEG-phosphatidylethanolamine, PEG-polylactic acid, polylysine-poly(lactic-co-glycolic) acid, polyetherimide-polylactic acid, PEG-polycaprolactone, PEG-poly(lactic-co-glycolic) acid, poloxamer 188, polyoxyethylene fatty acid ester, polyoxyethylene fatty acid ether or polyoxyethylene methyl castor oil ether.

The heat-sensitive excipient generally comprises a polymer, a drug or a surfactant which can bring heat-sensitivity to the liposome. The polymer preferably comprises polyprene acrylamide, polyprene acrylic acid, polyphosphate, or poly phospholipid-amide copolymer. The drug preferably comprises zedoary turmeric oil, elemene or brucea javanica oil. The surfactant is preferably a Tween surfactant (such as Tween-80) and/or a brij surfactant.

The ion additive preferably comprises a cationic additive (such as octadecylamine) and/or an anion additive (such as phosphatidic acid and/or phosphatidylserine).

A mass percentage of the above excipients can be selected according to the mass percentage of such kind of excipients contained in the ordinary liposome in the art. For example, when the blank liposome includes the surfactant, a mass percentage of the surfactant in the blank liposome is preferably in the range of 0% to 50%, excluding 0%. When the blank liposome includes the ion additive, a mass percentage of the ion additive in the blank liposome is preferably in the range of 0% to 10%, excluding 0%.

The blank liposome can be prepared by conventional methods of preparing a liposome. Commonly, an injection method, a reverse evaporation method, a freezing and thawing method, a double emulsion method, an initiative encapsulation method, a precursor liposome preparation method, a film dispersion method, a freeze-drying method, an ammonium sulfate gradient method or a pH gradient method, as well as any combination of above two methods can be adopted. The present invention preferably adopts the first method or the second method as follows, wherein the first method or the blank liposome prepared thereby does not include a cryoprotectant, and the second method or the blank liposome prepared thereby includes a cryoprotectant.

The first method includes the steps of:

(1) mixing a lipid and a ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and (2) removing the organic solvent of the clear solution obtained in step (1), filming, mixing the film with water optionally containing a hydrophilic antioxidant, a hydrophilic surfactant, a hydrophilic heat-sensitive excipient, a hydrophilic pH sensitive material, and/or a hydrophilic ion additive to obtain an aqueous mixture, filtering the mixture after an operation of ultrasound, high pressure homogenization or pushing through a membrane to obtain an aqueous solution containing a blank liposome, drying to get the blank liposome;

The second method includes the steps of:

(1) mixing a lipid and a ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and (2) removing the organic solvent of the clear solution obtained in step (1), filming, mixing the film with an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, filtering the mixture after an operation of ultrasound, high pressure homogenization or pushing through a membrane to obtain an aqueous solution containing a blank liposome, drying to get the blank liposome.

In the first method or in the second method, wherein the lipid, the ginsenoside of Formula I, the cholesterol, the antioxidant, the soybean oil and/or sodium oleate, the cryoprotectant, the surfactant, the heat-sensitive excipient, the pH sensitive material, and the ion additive are as defined above.

In step (1) of the first or second method, the organic solvent can be a conventional organic solvent used in the preparation of a liposome in the art, which preferably comprises a nitrile solvent, a $C_{1-4}$ alcohol solvent, a ketone solvent, an alkane solvent, an ether solvent, a halogenated hydrocarbon solvent, a sulfoxide solvent, or an aldehyde solvent, more preferably comprises a $C_{1-4}$ alcohol solvent, a nitrile solvent, an ether solvent or a halogenated hydrocarbon solvent. The nitrile solvent preferably comprises acetonitrile. The $C_{1-4}$ alcohol solvent preferably comprises methanol, ethanol, isopropanol or n-butanol. The ether solvent preferably comprises tetrahydrofuran or diethyl ether. The halogenated hydrocarbon solvent preferably comprises chloroform or dichloromethane. The ketone solvent preferably comprises acetone or butanone. The alkane solvent preferably comprises petroleum ether. An amount of the organic solvent can be a conventional amount used in the preparation of a liposome in the art, without particularly limited, a general requirement of which is capable of obtaining a clear solution after the mixing of the organic solvent and all the components. Preferably, a ratio of the organic solvent's volume to the total mass of all the components dissolved in the organic solvent in step (1) of the first or second method is 5 to 20 mL/g.

Step (1) of the first or second method is generally carried out at the temperature of 0 to 80° C., preferably 10 to 80° C., more preferably 10 to 65° C. Based on the common knowledge in this field, in some cases, in order to reach 80° C., heating is required. Or, when the blank liposome prepared thereby includes a heat-sensitive material, such as protein materials, step (1) of the first or second method is generally carried out at the temperature of e 0° C.

In step (2) of the first or second method, the operation of removing the organic solvent of the clear solution obtained in step (1) can be a conventional operation in this field, which is usually conducted with a rotary evaporator or a membrane evaporator. The temperature at which the organic solvent is removed can be selected according to the organic solvent to be removed, generally is 25 to 80° C.

In step (2) of the first or second method, the operation of ultrasound, high pressure homogenization or pushing through a membrane can be a conventional operation in this field. After the operation of ultrasound, high pressure homogenization or pushing through a membrane, a particle size of the liposome is generally ranging from 0.05 to 0.3 microns.

In step (2) of the first or second method, the operation of filtration can be a conventional operation in the preparation of the liposome in this field, the purpose of which is to remove bacteria, solid particles and particularly large liposome (in a method of preparing a liposome loaded with the active substance, an unencapsulated free drug can also be removed) etc. In the present invention, the filtration is preferably microporous membrane filtration. The pore size of the microporous membrane is preferably 0.22 micron.

In step (2) of the second method, the aqueous cryoprotectant solution refers to an aqueous solution formed by mixing the cryoprotectant and water. The aqueous cryoprotectant solution is preferably a 5% to 10% aqueous solution of the cryoprotectant, the percentage refers to the percentage of the mass of the cryoprotectant relative to the total mass of the aqueous solution of the cryoprotectant. An amount of the aqueous cryoprotectant solution is without particular limitation, as long as there is no influence on the formation of the blank liposome, preferably, it is the same as that of the organic solvent used in step (1).

In a preferred embodiment of the present invention, in the second method, when the cryoprotectant is a buffer reagent, after the filming operation in step (2), the cryoprotectant is mixed directly.

In step (2) of the first or second method, the operation of drying can be a conventional operation in this field, preferably is freeze-drying which generally utilizes a freeze dryer. The temperature and time required by the freeze-drying are conventional temperature and time in this field which is without particular limitation.

In the first or second method, for easy storage, the aqueous solution containing the blank liposome obtained in step (2) is split charging into vials, dried, swept with protective gas (argon or nitrogen) and sealed.

The blank liposome can be used to prepare a liposome loaded with and encapsulate within the membrane an active substance, wherein the active substance comprises a drug, a cosmetically active substance or a substance with healthcare function. Therefore, the present invention also provides a loaded liposome which comprises a blank liposome and an active substance loaded to and encapsulating within the liposome's membrane, wherein the active substance comprises a drug, a cosmetically active substance, or a substance with healthcare function.

In the loaded liposome, a mass ratio of the active substance to the ginsenoside of Formula I is 1:0.1 to 1:10, more preferably 1:2 to 1:6 (such as 1:3 or 1:4).

The drug can be a conventional drug in the art, preferably comprises an antitumor drug, an antifungal drug, an antiviral drug, antibiotics, a non-steroidal anti-inflammatory drug, a calcium ion antagonist, an immunosuppressive agent, an anesthetic, a cardiovascular and vasodilation drug, a gastrointestinal drug, an antidepressant drug, a biological agent, a polynucleotide or an oligonucleotide (including a ribonucleotide and a deoxyribonucleotide).

The antitumor drug can be a conventional antitumor drug in the art, preferably comprises paclitaxel, docetaxel, cabazitaxel, irinotecan hydrochloride, hydroxycamptothecin, aminocamptothecin, 7-ethyl-10-hydroxy camptothecin, topotecan hydrochloride, lurtotecan, topotecan, belotecan, cisplatin, carboplatin, oxaliplatin, nedaplatin, lobaplatin, satraplatin, miriplatin, amyl platinum, aroplatin (L-NDDP), carmustine, chlorambucil, melphalan, harringtonine, homoharringtonine, triptolide, tacrolimus, daunorubicin, pingyangmycin, doxorubicin hydrochloride, idarubicin, fluorouracil, cytarabine, methotrexate, etoposide phosphate, desoxy-podophyllotoxin, huperzine-A, vinorelbine tartrate, vincristine sulfate, vinblastine sulfate, vinorelbine, vindesine sulfate, temozolomide, tegafur, cyclophosphamide, ifosfamide, dacarbazine, epothilone A, epothilone B, epothilone C, epothilone D, epothilone E, epothilone F, bortezomib, gemcitabine hydrochloride, fludarabine phosphate, capecitabine, decitabine, pemetrexed disodium, sorafenib, recombinant human interferon a2b, cytosine arabinoside, all trans retinoic acid, interleukin-2, etoposide, thymidylate synthase inhibitor, mitoxantrone, minoxidil, azithromycin, epirubicin hydrochloride, doxorubicin hydrochloride (adriamycin), amrubicin hydrochloride, 5-aminolevulinic acid (5-ALA), gefitinib, imatinib, erlotinib, sunitinib, dasatinib, lapatinib, axitinib, apatinib, nilotinib, bosutinib, vandetanib, telatinib, neratinib, canertinib, saracatinib, octenidine, sorafenib, icotinib, mubritinib, lestaurtinib, tandutinib, dovitinib, 3',5'-dipalmitoyl cyclocytidine or curcumenol.

The antifungal drug preferably comprises amphotericin B, gentamicin, indomethacin, penicillin G, econazole nitrate, flucytosine, fluconazole, itraconazole, voriconazole, posaconazole, ravuconazole, caspofungin, micafungin, anidulafungin, cefpiramide sodium, cefotaxime sodium, ceftriaxone, cefoperazone, cefditoren pivoxil, cefoxitin sodium, cefalexin, cefuroxime sodium, cefixime, cefpodoxime, cefmenoxime, cefodizime, cefsulodin, cefazonam, ceftizoxime, cefetamet pivoxil, cefterampivoxil, ceftibuten, cefdinir, cefamandole, cefotiam, ceforanide, cefonicid, ceftazidime, cefradine, cefprozil, cefazolin sodium, cefadroxil, cephalothin, cefathiamidine, cefaloridine, cephacetrile, ceftezole, cefapirin, cefpirome, cefclidin, cefepime, fusidate sodium, florfenicol or tigecycline.

The antiviral drug preferably comprises ribavirin, acyclovir, cytarabine, idoxuridine, acyclovir laurate, acyclovir palmitate, iododeoxyuridine, cyclocytidine, dipalmitoyl cyclocytidine, phosphoric acid formate, phosphoric acid acetate, cimetidine, dipyridamole, rifampin, isoniazid, praziquantel, doxycycline, saquinavir, indinavir, ritonavir, nelfinavir, amprenavir, tipranavir, BMS232632, lamivudine, zidovudine, didanosine (ddi), zalcitabine (ddc), stavudine (d4t), abacavir, adefovirdipivoail (pmea), tenofovir (pmpa), fluoro lamivudine (ftc), nevirapine, delavirdin, efavirens, interleukin-2 (il-2), tilmicosin or diclazuril.

The antibiotic is preferably comprises penicillin, penicillin V, amoxicillin, ampicillin, oxacillin, cloxacillin, procaine penicillin, benzathine penicillin, piperacillin, mezlocillin, ticarcillin, azlocillin, mezlocillin, carbenicillin, sulbenicillin, furbucillin, nafcillin, dicloxacillin, pivampicillin, apalcillin, aspoxicillin, pivmecillinam, methicillin, lenampicillin, fomidacillin, flucloxacillin, kanamycin, natamycin, mitomycin, amikacin, tylosin, verteporfin, cefpiramide sodium, netilmicin sulfate, azithromycin, ofloxacin, ciprofloxacin, enoxacin, lomefloxacin, pefloxacin, rufloxacin, sparfloxacin, fleroxacin, moxifloxacin, grepafloxacin, trovafloxacin, norfloxacin, gemifloxacin, gatifloxacin, tosufloxacin, pazufloxacin, sparfloxacin, clarithromycin, clindamycin, polymyxin, tobramycin, vancomycin, azithromycin, doxycycline, tetracycline, oxytetracycline, minocycline, aureomycin, guamecycline, demeclocycline, metacycline, etimicin, netilmicin, sisomicin, amikacin, arbekacin, dibekacin, aztreonam, meropenem, imipenem, thienamycin, panipenem, ertapenem, neomycin, paromomycin or spectinomycin.

The calcium ion antagonist preferably comprises nimodipine, nifedipine, nicardipine, nitrendipine, verapamil, amlodipine, diltiazem, flunarizine, prenvlamine, gallopamil or tiapamil.

The non-steroidal anti-inflammatory drug preferably comprises indomethacin, aspirin, paracetamol, naproxen, diclofenac, ibuprofen, nimesulide, rofecoxib or celecoxib.

The immunosuppressive agent preferably comprises cyclosporin, alprostadil (also known as prostate E-1), cyclosporine, tacrolimus, rapamycin, mycophenolate mofetil or mizoribine.

The anesthetic preferably comprises halothane, sevoflurane, isoflurane, enflurane, propofol, fentanyl, urethane, lidocaine, procaine, tetracaine, bupivacaine, pelltobarbitalum natricum, chloral hydrate, ketamine, chloralose or morphine.

The cardiovascular and vasodilation drug preferably comprises dabigatran etexilate, alogliptin, polysaccharide sodium, ginkgolides, gingko flavonoid, *Ginkgo biloba* extract, asarone, olmesartan medoxomi, repaglinide, lipoic acid, breviscapine, urapldil, niacin, captopril, losartan, puerarin, tanshinone IIA, sarpogrelate hydrochloride, fluvastatin, pravastatin, simvastatin, lovastatin, simvastatin, mevastatin, cerivastatin, rosuvastatin, atorvastatin calcium or rosuvastatin calcium.

The gastrointestinal drug preferably comprises omeprazole, lansoprazole, ilaprazole, pantoprazole, rabeprazole, terazosin, esomeprazole, tenatoprazole, leminoprazole, tenatoprazole, disuprazole or lafutidine.

The antidepressant drug preferably comprises agomelatine, fluoxetine, paroxetine, duloxetine, sertraline, fluvoxamine, citalopram, escitalopram, venlafaxine, mirtazapine, imipramine, amitriptyline, clomipramine, doxepin, remeron, venlafaxime, phenelzine, isocarboxazid or tranylcypromine.

The polynucleotide and oligonucleotide preferably comprises a fragment having genetic functions and consisting of the basic groups such as A, T, C, G or U, for example, SiRNA, RNAi sequence of antisense nucleic acid or microglia NLRP3 gene.

The biological agent preferably comprises a conventional mono-antibody drug in this field, insulin, gamma globulin, antitoxic serum, interferon, interleukin, tumor necrosis factor, active factor of skin, epidermal growth factor, influenza vaccine, hepatitis A vaccine, cancer vaccine, recombinant human acidic fibroblast growth factor or vascular endothelial growth factor 2 monoclonal antibody (VEGFR-2 monoclonal antibody).

The cosmetically active substance generally refers to an active substance which has functions of nourishing, improving the condition of skin and preventing skin disease, preferably comprises ursolic acid, superoxide dismutase (SOD), biological protein T4N5, vitamin D2, methyl nicotinate, refined snake oil, hyaluronic acid, essential oil or ceramide.

The substance with healthcare function can be a conventional substance with healthcare function in this filed, preferably comprises glycyrrhizin, glycyrrhizic acid, disodiumglycyrrhizinate, methyl glycyrrhizinate, diammoniumglycyrrhizinate, vitamin E, resveratrol, coenzyme Q10, silymarin, anthocyanins, proanthocyanidins, lutein, folic acid, folinic acid, curcumin, emodin, tea polyphenols, epigallocatechin gallate (EGCG), catechin, blueberry extract, glutathione or oxymatrine.

In a preferred embodiment of the present invention, in the loaded liposome, the drug comprises paclitaxel, docetaxel or irinotecan hydrochloride, the liposome comprises phospholipid and a ginsenoside of Formula I, the ginsenoiside comprises ginsenoside Rg5, the mass ratio of the phospholipid to the ginsenoside Rg5 is in the range of 0.5:1 to 100:1, preferably in the range of 0.5:1 to 20:1, more preferably in the range of 0.5:1 to 4:1 (such as in the range of 0.5:1 to 2:1).

In another preferred embodiment of the present invention, the liposome further comprises a cholesterol, the mass ratio of the phospholipid to the ginsenoside Rg5 is in the range of 1:0.01 to 1:3 (such as in the range of 1:0.03 to 1:1), more preferably in the range of 1:0.05 to 1:0.9 (such as in the range of 1:0.3 to 1:0.75), most preferably in the range of 1:0.1 to 1:0.9 (such as in the range of 1:0.1 to 1:0.5), the mass ratio of the ginsenoside Rg5 to the cholesterol is in the range of 0.1:1 to 100:1, preferably in the range of 0.5:1 to 50:1, more preferably in the range of 0.5:1 to 10:1 (such as in the range of 1.5:1 to 6:1, or 5:1).

In another preferred embodiment of the present invention, the mass percentage of ginsenoside Rg5 in the membrane is in the range of 0.01% to 80%, preferably in the range of 10% to 80%, more preferably in the range of 10% to 40%, most preferably in the range of 20% to 40%, the mass percentage of the phospholipid in the membrane is in the range of 5% to 99.9%, preferably in the range of 10% to 70%, more preferably in the range of 30% to 70%, most preferably in the range of 30% to 60%, the mass percentage of the cholesterol in the membrane is in the range of 0% to 50%, preferably in the range of 0.5% to 50%, more preferably in the range of 5% to 40%, most preferably in the range of 5% to 30% (such as in the range of 10% to 20%).

In another preferred embodiment of the present invention, the liposome can further comprise and encapsulate within the liposome's membrane an antioxidant, a mass percentage of the antioxidant in the blank liposome is no more than 25%, preferably in the range of 0.001% to 15%, more preferably in the range of 0.01% to 10%, most preferably in the range of 0.01% to 5%, In another preferred embodiment of the present invention, the liposome can further comprise and encapsulate within the liposome's membrane a cryoprotectant, a mass percentage of the cryoprotectant in the blank liposome is no more than 80%, preferably in the range of 0.5% to 60%, more preferably in the range of 5% to 60%, most preferably in the range of 30% to 60%.

In another preferred embodiment of the present invention, the liposome can further comprise and encapsulate within the liposome's membrane soybean oil and/or sodium oleate, a mass percentage of the soybean oil and/or sodium oleate in the blank liposome is usually in the range of 1% to 90%, preferably in the range of 15% to 80%, more preferably in the range of 20% to 70% (such as in the range of 25% or 62.5%), most preferably in the range of 20% to 30%, or 60% to 70%, the percentage refers to the mass of the "soybean oil and/or sodium oleate" relative to the total mass of the blank liposome. A mass ratio of the "soybean oil and/or sodium oleate" to the phospholipid in the blank liposome is preferably in the range of 1:0.1 to 1:10, more preferably in the range of 1:0.5 to 1:5, most preferably in the range of 1:0.5 to 1:4 (such as in the range of 1:1 to 1:2).

In another preferred embodiment of the present invention, the liposome can further comprise and encapsulate within the liposome's membrane other excipients. The other excipients and an amount of the other excipients are the same as that in the blank liposome.

In a preferred embodiment of the present invention, the liposome comprises soybean oil and/or sodium oleate, the ginsenoside Rg5 and phospholipid; or soybean oil and/or sodium oleate, the ginsenoside Rg5, phospholipid and a cryoprotectant; or soybean oil and/or sodium oleate, the ginsenoside Rg5, phospholipid, a cryoprotectant and an antioxidant.

In another preferred embodiment of the present invention, the liposome consists of the components mentioned-above.

In another preferred embodiment of the present invention, in the liposome, the phospholipid preferably comprises soybean lecithin, egg lecithin or dimyristoyl phosphatidylcholine, the antioxidant preferably comprises ascorbic acid, vitamin E, vitamin C or threonine, the cryoprotectant preferably comprises glucose, mannitol, xylitol, sucrose, lactose, trehalose or propanediol.

The present invention also provides a process for preparing the loaded liposome. When the liposome includes a cryoprotectant, the process for preparing the loaded liposome comprises any of Methods A, B, C, and D, wherein when the liposome does not contain or include a cryoprotectant, the process for preparing the loaded liposome comprises any one of Methods A1, B1, C1, and D1:

Method A comprises:

(1) mixing the lipid, the ginsenoside of Formula I, and the active substantive, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and (2) removing the organic solvent of the clear solution obtained in step (1), filming, mixing the film with an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, filtering the mixture after an operation of ultrasound, high pressure homogenization of the mixture or pushing the mixture through a membrane to obtain an aqueous solution containing the liposome loaded with the active substance, drying to give the loaded liposome;

Method B comprises:

(1) mixing the lipid and the ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and (2) removing the organic solvent of the clear solution obtained in step (1), filming, mixing the film with an active substance and an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a loaded liposome after an operation of ultrasound, high pressure homogenization of the mixture or pushing the mixture through a membrane, dialyzing and filtering to obtain an aqueous solution containing the liposome loaded with the active substance, drying to give the loaded liposome;

Method C comprises:

(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution in an organic solvent to obtain a clear solution, and (2) removing the organic solvent of the clear solution obtained in step (1), filming, mixing the film with an aqueous solution containing ammonium sulfate and a cryoprotectant, and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a blank liposome after an operation of ultrasound, high pressure homogenization of the mixture or pushing the mixture through a membrane, dialyzing, then mixing with an active substance, filtering to obtain an aqueous solution containing a liposome loaded with the active substance, drying to give the loaded liposome;

Method D comprises:

(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and (2) removing the organic solvent of the clear solution obtained in step (1), filming, mixing the film with citric acid and an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a blank liposome after an operation of ultrasound, high pressure homogenization of the mixture or pushing the mixture through a membrane, mixing the solution with an active substance and an aqueous solution of disodium hydrogen phosphate, filtering to obtain an aqueous solution containing a liposome loaded with the active substance, drying to give the loaded liposome;

Method A1 comprises:

(1) mixing the lipid, the ginsenoside of Formula I and an active substantive, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and (2) removing the organic solvent of the clear solution obtained in step (1), filming, mixing the film with water to obtain an aqueous mixture, optionally adding to the aqueous mixture a hydrophilic antioxidant, a hydrophilic surfactant, a hydrophilic heat-sensitive excipient, a hydrophilic pH sensitive material, and/or a hydrophilic ion additive, filtering the mixture after an operation of ultrasound, high pressure homogenization of the mixture or pushing the mixture through a membrane to obtain an aqueous solution containing a liposome loaded with the active substance, drying to give the loaded liposome;

Method B1 comprises:

(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and (2) removing the organic solvent of the clear solution obtained in step (1), filming, mixing the film with an active substance and optionally an aqueous solution containing a hydrophilic antioxidant, a hydrophilic surfactant, a hydrophilic heat-sensitive excipient, a hydrophilic pH sensitive material, and/or a hydrophilic ion additive, obtaining a solution containing a liposome loaded with an active substance after an operation of ultrasound, high pressure homogenization or pushing through a membrane, dialyzing and filtering to obtain an aqueous solution containing the liposome loaded with the active substance, drying to give the loaded liposome;

Method C1 comprises:

(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and (2) removing the organic solvent of the clear solution obtained in step (1), filming, mixing the film with an aqueous solution containing ammonium sulfate and optionally a hydrophilic antioxidant, a hydrophilic surfactant, a hydrophilic heat-sensitive excipient, a hydrophilic pH sensitive material, and/or a hydrophilic ion additive, obtaining a solution of a blank liposome after an operation of ultrasound, high pressure homogenization or pushing through a membrane, dialyzing, then mixing the solution with an active substance, filtering to obtain an aqueous solution containing a liposome loaded with the active substance, drying to give the loaded liposome;

Method D1 comprises:

(1) mixing the lipid and the ginsenoside of Formula I, and optionally, a cholesterol, a hydrophobic antioxidant, a hydrophobic surfactant, a hydrophobic heat-sensitive excipient, a hydrophobic pH sensitive material, and/or a hydrophobic ion additive in an organic solvent to obtain a clear solution, (2) removing the organic solvent of the clear solution obtained in step (1), filming, mixing the film with an aqueous solution containing citric acid and optionally a hydrophilic antioxidant, soybean oil and/or sodium oleate, a hydrophilic surfactant, a hydrophilic heat-sensitive excipient, a hydrophilic pH sensitive material, and/or a hydrophilic ion additive, obtaining a solution of a blank liposome after an operation of ultrasound, high pressure homogenization or pushing through a membrane, then mixing the blank liposome solution with an active substance and an aqueous solution of disodium hydrogen phosphate, filtering to obtain an aqueous solution containing a liposome loaded with the active substance, drying to give the loaded liposome.

In the Method A, B, C, D, A1, B1, C1 or D1, each condition or parameter is as defined in the first or the second method for preparing the blank liposome. The mass ratio of the active substance to the ginsenoside of Formula I is preferably 1:0.1 to 1:10 or 1:2 to 1:6; and the lipid, the ginsenoside of Formula I, the cholesterol, the antioxidant, the soybean oil and/or sodium oleate, the cryoprotectant, the surfactant, the heat-sensitive excipient, the pH sensitive material, the ion additive and the active substantive are each as defined above.

In step (2) of Method A, B, C or D, the cryoprotectant can be added after an aqueous solution containing the liposome loaded with the active substance is obtained before drying.

In Method B, C, B1 or C1, the operation of dialysis can be a conventional operation in the process for preparing a liposome in this field, preferably comprise putting a blank liposome solution or a loaded liposome solution in an aqueous solution of glucose (such as 0.15 mol/L) or pure water to give a mixed solution. The time cost by dialysis can be conventional in the process for preparing a liposome in this field, preferably is 5 to 20 hours, more preferably 12 hours. In Method B, C, B1 or C1, the operation of dialysis can be carried out before the operation of ultrasound, high pressure homogenization or pushing through a membrane.

In Method C or C1, a mass fraction of the ammonium sulfate in the aqueous solution of ammonium sulfate and the cryoprotectant or the aqueous solution of ammonium sulfate is without particular limitation, which can be a conventional mass fraction used for preparing a liposome through an ammonium sulfate gradient method in this field. The mass fraction of the ammonium sulfate in the aqueous solution of ammonium sulfate and the cryoprotectant or the aqueous solution of ammonium sulfate is preferably in the range of 1% to 15%, more preferably 6.6%, the percentage refers to the mass of the ammonium sulfate relative to the total mass of the aqueous solution above.

In Method C or C1, there preferably comprises an operation of warm-keeping before filtering. The operation of warm-keeping preferably comprises keeping warm at 30° C. to 80° C. (such as 37° C.) for 5 minutes to 1 hour (such as 30 minutes).

In Method D or D1, a concentration and an amount of the aqueous solution of citric acid are without particular limitation, which can be conventional concentration and amount used for preparing a liposome through a pH-gradient method in this field. In the present invention, the mass concentration of citric acid in its aqueous solution is preferably in the range of 1% to 15%, more preferably 5.76%, the percentage refers to the mass of the citric acid relative to the total mass of the aqueous solution of citric acid. A concentration and an amount of the aqueous solution of disodium hydrogen phosphate are without particular limitation, which can be conventional concentration and amount for preparing a liposome through a pH-gradient method in this field. In the present invention, the mass concentration of disodium hydrogen phosphate in its aqueous solution is preferably in the range of 5% to 20%, more preferably 7.1%. An amount of the aqueous solution of disodium hydrogen phosphate is generally capable of keeping the pH of the aqueous solution containing the liposome loaded with the active substance between 6.5 and 7.5 (such as 7.3). In order to reach the desired pH quickly, pure water is added to adjust the pH of the aqueous solution of the liposome loaded with the active substance between 6.5 and 7.5 (such as 7.3) before filtering.

In Method D or D1, there preferably comprises an operation of warm-keeping before filtering. The operation of warm-keeping preferably comprises keeping warm at 30° C. to 80° C. (such as 60° C.) for 5 minutes to 1 hour (such as 30 minutes).

In each method above, the active substance may also preferably be used in the form of an aqueous solution of the active substance or an organic solution of the active substance according to the lipid solubility or water solubility of the active substance. The mass concentration of the aqueous solution of the active substance or the organic solution of the active substance may be without particular limitation, preferably a mass volume percentage of the aqueous solution or the organic solution is in the range of 1% to 20%, the percentage refers to the mass (g) of the active substance relative to the total volume (mL) of the aqueous solution of the active substance or the organic solution of the active substance. The organic solvent contained in the organic solution of the active substance can be a conventional organic solvent in this field, which is capable of dissolving the active substance well. In the present invention, the organic solvent is preferably a sulfoxide solvent, such as dimethyl sulfoxide (DMSO).

A process for preparing the loaded liposome, comprising Method ①, Method ②, Method ③, Method ④, Method ⑤, or Method ⑥, wherein Method ① comprises: adding soybean lecithin, ginsenoside Rg5 and paclitaxel into acetonitrile and stirring to form a clear solution; wherein a mass ratio of the soybean lecithin, ginsenoside Rg5 and paclitaxel is 10:6:3, a ratio of the volume of the acetonitrile to the mass of the ginsenoside Rg5 is 100 mL/3 g; removing the organic solvent in a thermostatic water bath at 50 to 60° C. to form a film, and adding purified water, a ratio of the volume of the purified water to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing protective gas, sealing to give the ginsenoside Rg5 paclitaxel liposome;

Method ② comprises: adding egg lecithin, ginsenoside Rg5, paclitaxel and threonine into methanol and stirring to form a clear solution, wherein a mass ratio of the egg lecithin, ginsenoside Rg5, paclitaxel, cholesterol and threonine is 13:12:4:5:5, a ratio of the volume of the methanol to the mass of the ginsenoside Rg5 is 100 mL/3 g, removing the organic solvent in a thermostatic water bath at 60 to 70° C. to form a film, and adding 5% glucose aqueous solution, a ratio of the volume of the glucose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing a protective gas, sealing to give the ginsenoside Rg5 paclitaxel liposome;

Method ③ comprises: adding egg lecithin, ginsenoside Rg5, paclitaxel, soybean oil and vitamin C into chloroform and stirring to form a clear solution, wherein a mass ratio of the egg lecithin, ginsenoside Rg5, paclitaxel, soybean oil and vitamin C is 8:6:1.5:4:0.5, a ratio of the volume of the chloroform to the mass of the ginsenoside Rg5 is 100 mL/3 g, the organic solvent is removed at 30 to 60° C. to form a film, and adding 10% trehalose aqueous solution, a ratio of the volume of the trehalose aqueous solution to the mass of the ginsenoside Rg5 is 100 mL/3 g, carrying out an operation of homogenization by a high pressure homogenizer until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing a protective gas, and sealing to give the ginsenoside Rg5 paclitaxel liposome;

Method ④ comprises: adding egg lecithin, ginsenoside Rg5, paclitaxel, soybean oil, cholesterol and vitamin E into chloroform and stirred to form a clear solution, wherein a mass ratio of the egg lecithin, ginsenoside Rg5, paclitaxel, soybean oil, cholesterol and vitamin E is 14:12:4:8:0.5:0.1, a ratio of the volume of the chloroform to the mass of the ginsenoside Rg5 is 100 mL/3 g, removing the organic solvent at 30 to 60° C. to form a film, and adding 5% saccharose aqueous solution, a ratio of the volume of the saccharose aqueous solution to the mass of the ginsenoside Rg5 is 100 mL/3 g, carrying out an operation of homogenization by a high pressure homogenizer until the particle size of the liposome is between 0.1 and 0.3 micron, filtering through a 0.22 micron microporous membrane thereby obtaining an aqueous solution containing ginsenoside Rg5 paclitaxel liposome, then freeze drying the aqueous solution containing ginsenoside Rg5 paclitaxel liposome, then introducing protective gas, sealing to give the ginsenoside Rg5 paclitaxel liposome;

Method ⑤ comprises: adding egg lecithin, ginsenoside Rg5, docetaxel, soybean oil, and vitamin C into chloroform and stirred to form a clear solution, wherein a mass ratio of the egg lecithin, ginsenoside Rg5, docetaxel, soybean oil, and vitamin C is 8:6:3:4:5, a ratio of the volume of the chloroform to the mass of the ginsenoside Rg5 is 100 mL/3 g, removing the organic solvent at 30 to 60° C. to form a film, and adding 10% trehalose aqueous solution, a ratio of the volume of the trehalose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 docetaxel liposome, freeze drying the aqueous solution containing ginsenoside Rg5 docetaxel liposome, introducing protective gas, sealing to give the ginsenoside Rg5 docetaxel liposome;

Method ⑥ comprises: adding egg lecithin, ginsenoside Rg5, irinotecan hydrochloride and soybean oil into chloroform and stirring to form a clear solution, wherein a mass ratio of the egg lecithin, ginsenoside Rg5, irinotecan hydrochloride and soybean oil is 8:6:2:4:5, a ratio of the volume of the chloroform to the ginsenoside Rg5 is 100 mL/3 g, removing the organic solvent at 30 to 60° C. to form a film, and adding 10% trehalose aqueous solution, a ratio of the volume of the trehalose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane to obtain an aqueous solution containing ginsenoside Rg5 docetaxel liposome, freeze drying the aqueous solution to contain ginsenoside Rg5 docetaxel liposome, introducing protective gas, and sealing to give the ginsenoside Rg5 docetaxel liposome.

In the process for preparing the loaded liposome, a mass ratio of the active substance can be a conventional mass ratio in this field, preferably, the mass ratio of the active substance to the ginsenoside of Formula I is 1:0.1 to 1:10, more preferably 1:2 to 1:6 (such as 1:3 or 1:4).

A particle size of the blank liposome or the loaded liposome can be a conventional particle size in this field, preferably is in the range of 30 to 2000 nm, more preferably in the range of 30 to 300 nm, most preferably in the range of 50 to 300 nm. The encapsulated efficiency of the loaded liposome is preferably 80% or more, more preferably 90% or more, most preferably 95% or more.

When the active substance of the loaded liposome is a drug or a substance with healthcare function, an administration of the loaded liposome can be a conventional administration in this field, preferably is an injection administration, an oral administration or cutaneous penetration used for the treatment of diseases and/or medical health care. Therefore, the loaded liposome is generally prepared in the form suitable for injection, lyophilized injection, oral administration, or topical administration. The injection administration preferably includes intravenous injection, intramuscular injection, intraperitoneal injection, intradermal injection or subcutaneous injection. Commonly, the loaded liposome is added into normal saline, phosphate buffered solution or 5% glucose aqueous solution to prepare an injection solution for injection.

In the loaded liposome, when the active substance is an antitumor drug, the loaded liposome generally has targeting effect on tumor cells, anti-multi-drug resistance effect, synergism and attenuation effects and synergism of drug.

Shown in the table are the structures of exemplary ginsenosides that are particularly suitable for the prevention invention:

| Name | Structure |
|---|---|
| Ginsenoside Rg4 | 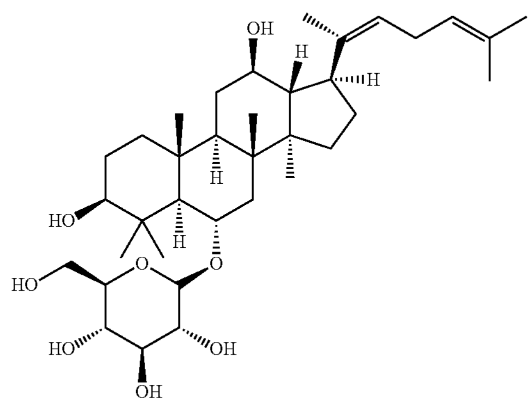 |
| Ginsenoside Rg5 | 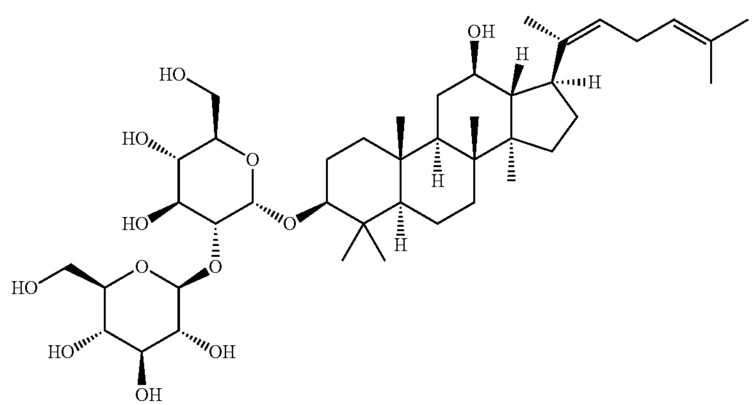 |

| Name | Structure |
|---|---|
| Ginsenoside Rg6 | 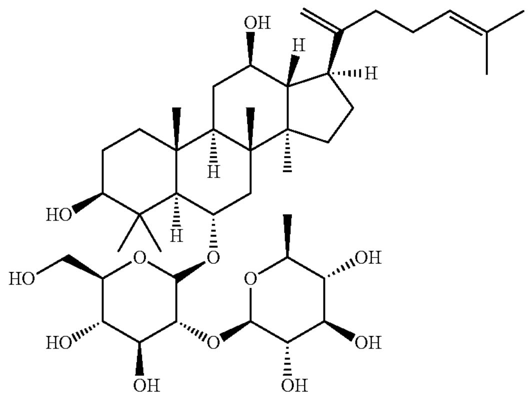 |
| Ginsenoside Rk1 | 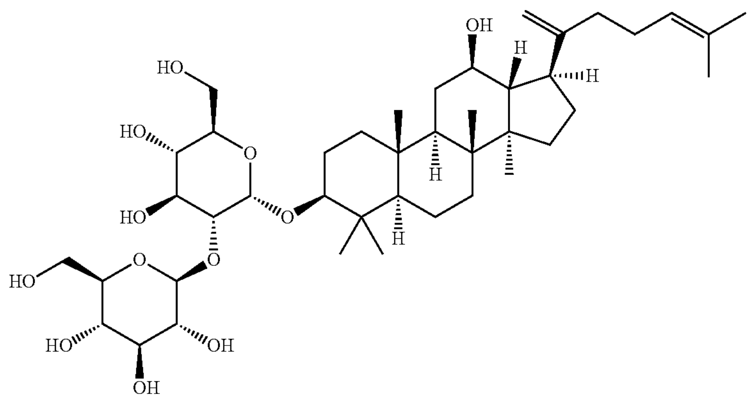 |
| Ginsenoside Rk2 | 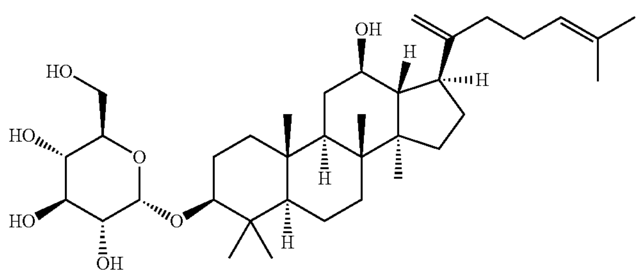 |
| Ginsenoside Rk3 | 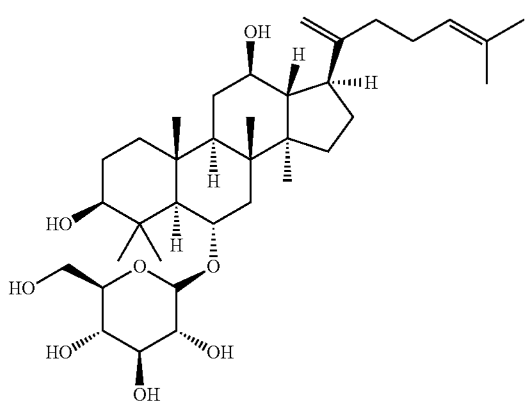 |

| Name | Structure |
|------|-----------|
| Ginsenoside Rk4 | 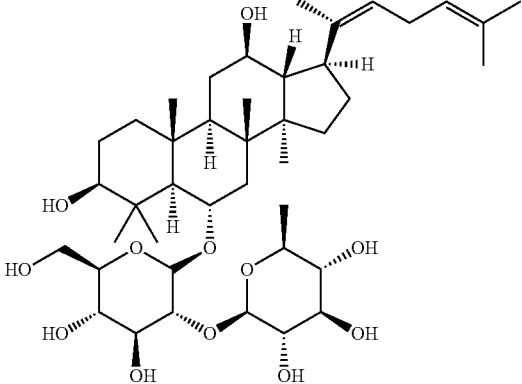 |
| Ginsenoside Rh3 | 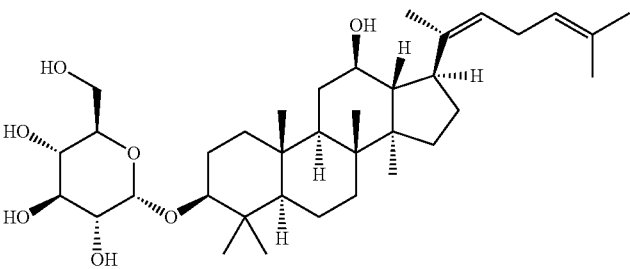 |
| Ginsenoside Rh4 (20E) | 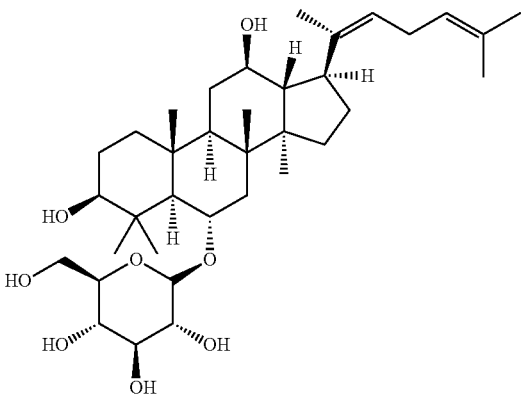 |
| Ginsenoside F4 (20E) | 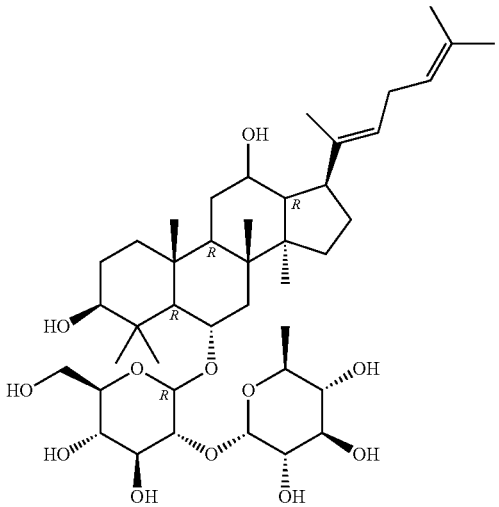 |

-continued

| Name | Structure |
|---|---|
| Ginsenoside Rs5 | 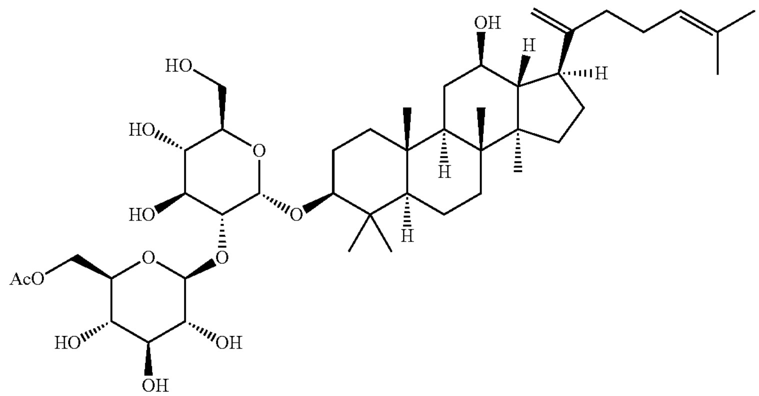 |
| Ginsenoside Rs6 | 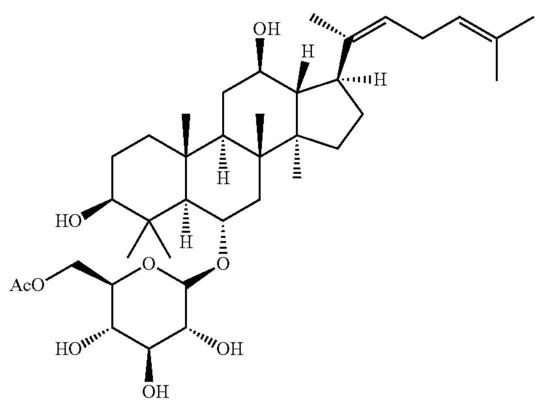 |
| Ginsenoside Rs7 | 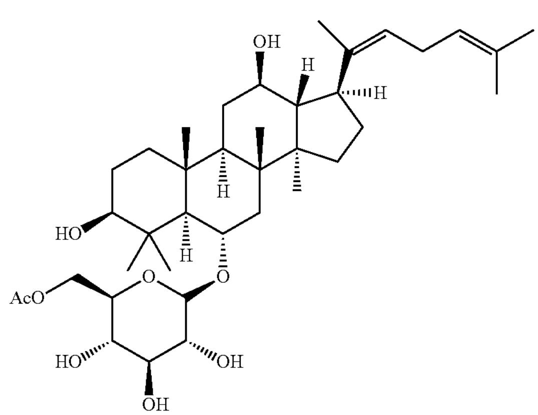 |

-continued

| Name | Structure |
|---|---|
| Notoginsenoside T5 | 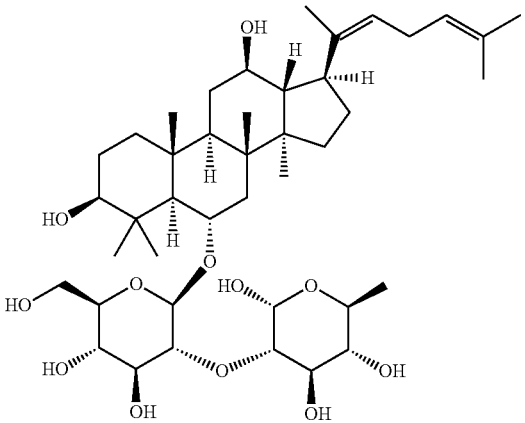 |
| Damulin A | 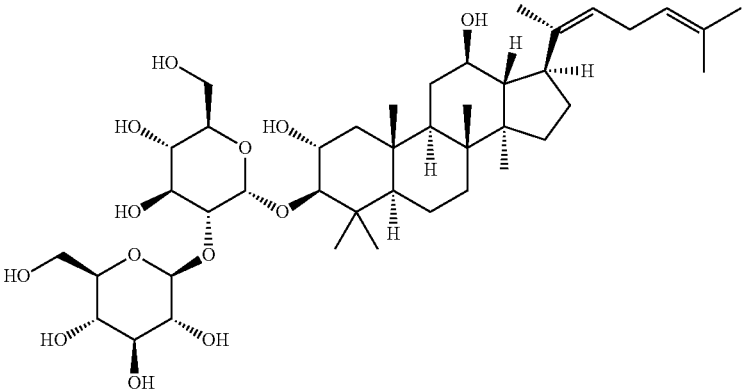 |
| Damulin B | 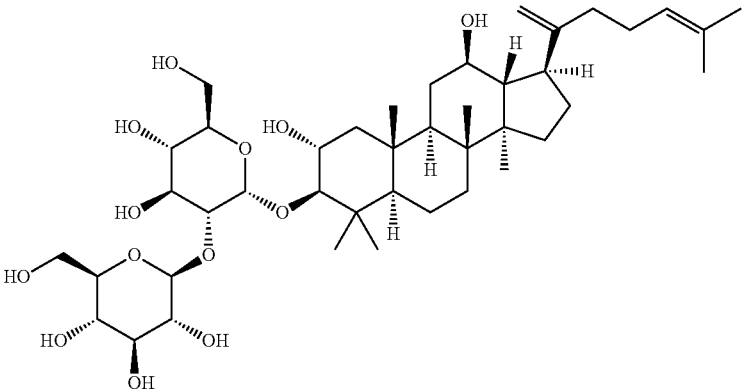 |

In the present invention, the mentioned optimized conditions can be optionally combined based on the common knowledge in this field to obtain preferred embodiments.

In the present invention, room temperature refers to 10 to 30° C.

In the present invention, a density of the aqueous solution of the cryoprotectant or the aqueous solution of the active substance is 1 g/mL (i.e. the density of water), therefore, the total mass of the aqueous solution of the cryoprotectant or the aqueous solution of the active substance is calculated by $m=\rho*V$.

In the present invention, a density of the organic solution of the active substance depends on the kind of the organic solvent, for example, when the organic solvent is DMSO, the density of the organic solution of the active substance is 1.1 g/mL.

In the present invention, the reagents and raw materials are commercially available.

The positive effects of the present invention are:

The blank liposome of the present invention has the advantages of high efficiency, good safety, good stability, enhanced targeting, good uniformity, stable and reliable quality, and convenient preparation process. When the active substance is an antitumor drug, the loaded liposome generally has targeting effect on tumor cells, anti-multi-drug resistance effect, synergism and attenuation effects and synergism of drug.

BRIEF DESCRIPTIONS OF THE DRAWINGS

Figure 31:
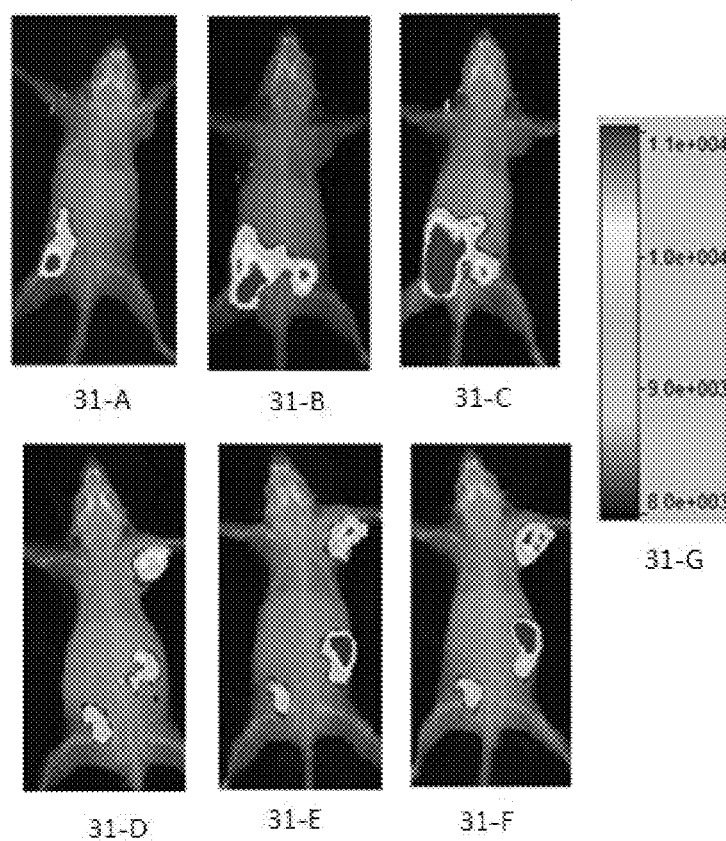

FIG. 31 is a distribution in vivo figure of IR783 fluorescence that recorded by a live imager, wherein FIG. 31-A, FIG. 31-B and FIG. 31-C are respectively the distribution in vivo figure of IR783 fluorescence of the control group at 2nd, 6th and 10th hour that recorded by the live imager, FIG. 31-D, FIG. 31-E and FIG. 31-F are respectively the distribution in vivo figure of IR783 fluorescence of the experimental group at 2nd, 6th and 10th hour that recorded by the live imager, FIG. 31-G is a fluorescence ruler, wherein according to the fluorescence intensity, color is red, yellow, green and blue in sequence, red indicates the strongest fluorescence, blue indicates weak fluorescence.

Figure 32:
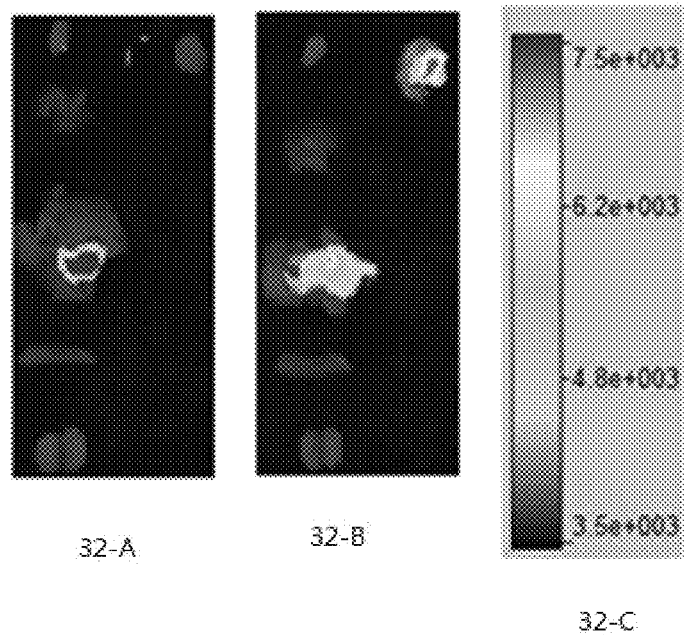

FIG. 32 is a fluorescence figure of the isolated viscera of the control group mice and the experimental group mice, wherein FIG. 32-A and FIG. 32-B are respectively the fluorescence figure of the isolated viscera of the control group mice and the experimental group mice, FIG. 32-C is a fluorescence ruler, wherein according to the fluorescence intensity, color is red, yellow, green and blue, red indicates the strongest fluorescence, blue indicates weak fluorescence.

Figure 33:
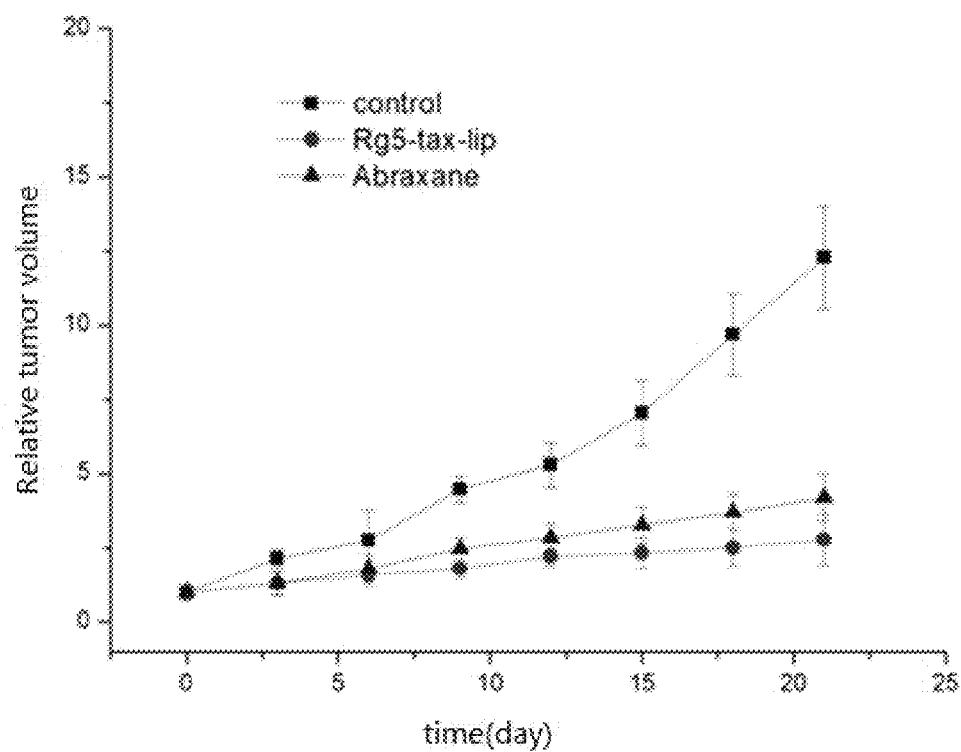

FIG. 33 is an antitumor graph of the control group, Taxol+Rg5 group and Abraxane group against human lung cancer cell line (A549).

Figure 34:
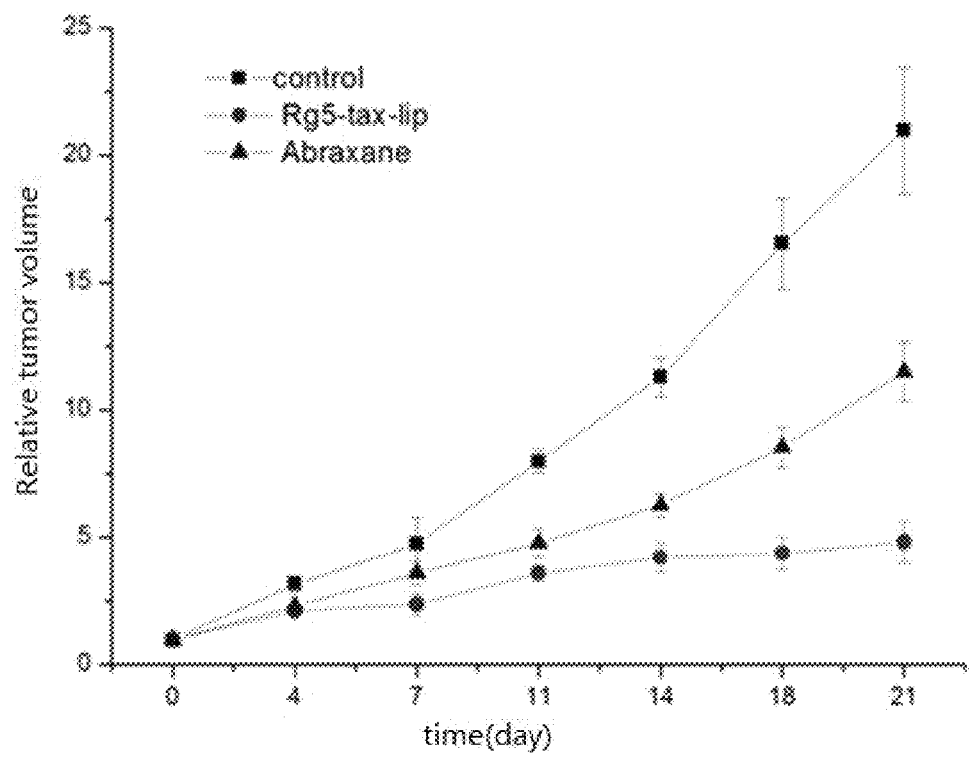

FIG. 34 is an antitumor graph of the control group, Taxol+Rg5 group and Abraxane group against paclitaxel-resistant human lung cancer cell line (A549/T).

Figure 35:
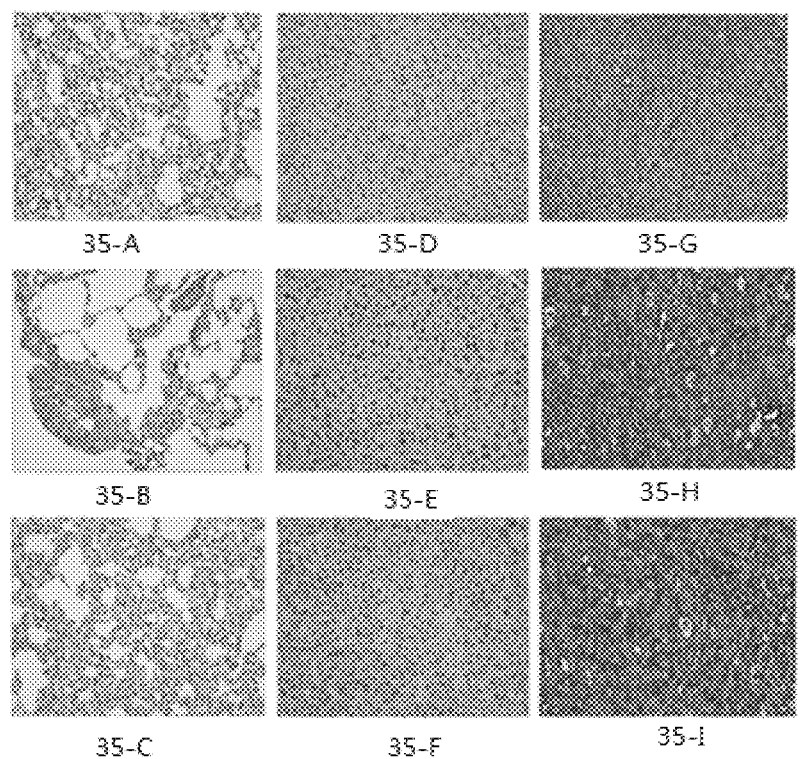

FIG. 35 is a microscope observation figure of the paraffin sections of lung, liver and tumor tissue of normal mice, control group and Taxol+Rg5 group mice after stained by hematoxylin-eosin, wherein FIG. 35-A, FIG. 35-D and FIG. 35-G are respectively the microscope observation figure of the paraffin sections of lung, liver and tumor tissue of normal mice after stained by hematoxylin-eosin, FIG. 35-B, FIG. 35-E and FIG. 35-H are respectively the microscope observation figure of the paraffin sections of lung, liver and tumor tissue of the control group tumor-bearing mice after stained by hematoxylin-eosin, FIG. 35-C, FIG. 35-F and FIG. 35-I are respectively the microscope observation figure of the paraffin sections of lung, liver and tumor tissue of the experimental group mice after stained by hematoxylin-eosin.

Figure 36:
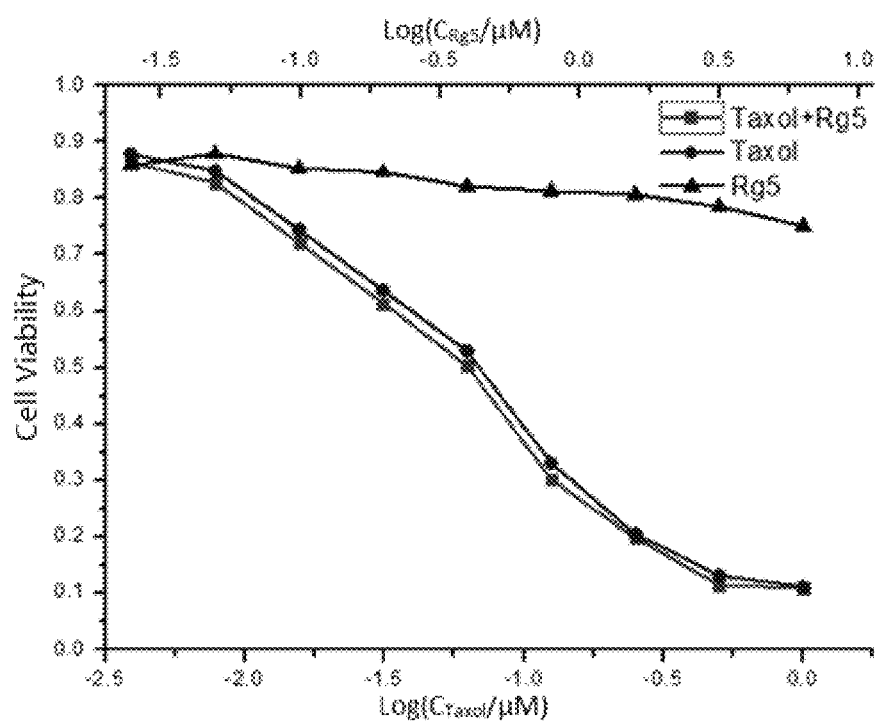

FIG. 36 is a cell survival rate graph of Taxol, blank Rg5 and Taxol+Rg5 against human breast cancer cell line (MCF-7).

Figure 37:
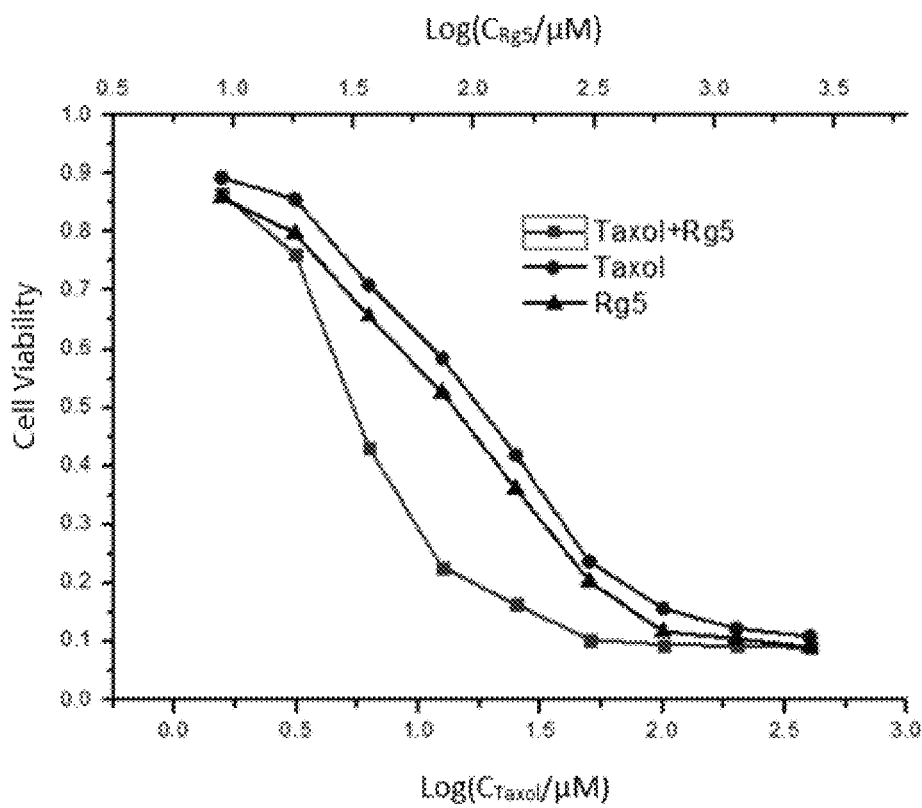

FIG. 37 is a cell survival rate graph of Taxol, blank Rg5 and Taxol+Rg5 against paclitaxel-resistant human breast cancer cell line (MCF-7/T).

Figure 38:
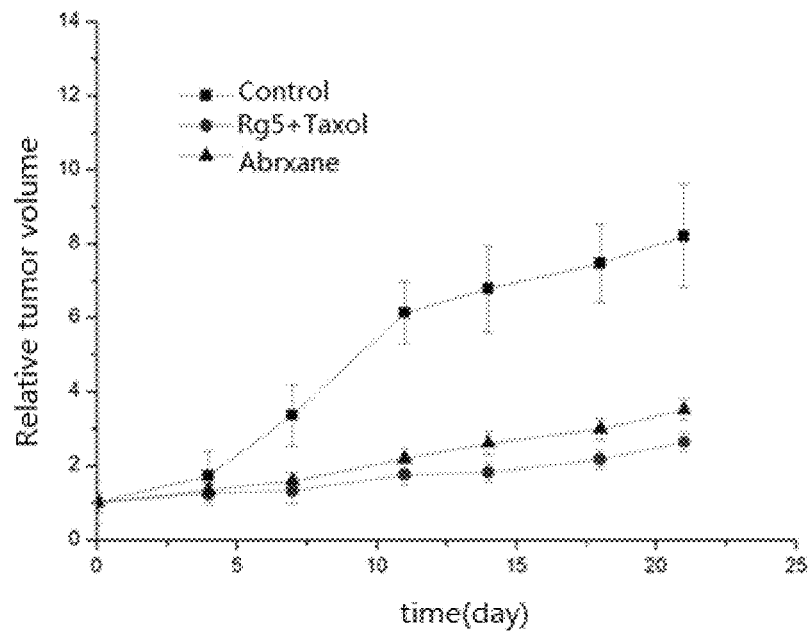

FIG. 38 is an antitumor graph of the control group, Taxol+Rg5 group and Abraxane group against human breast cancer cell line (MCF-7).

Figure 39:
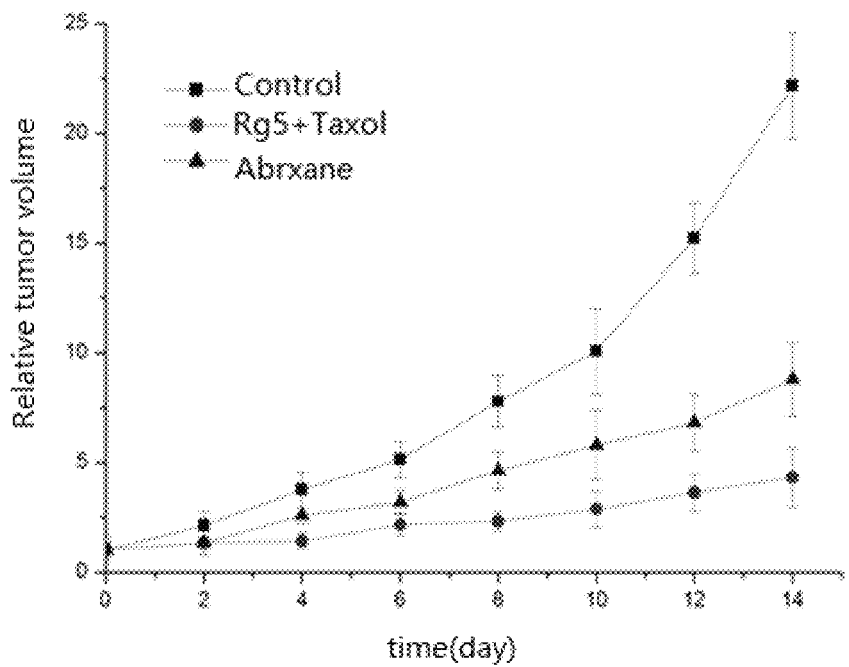

FIG. 39 is an antitumor graph of the control group, Taxol+Rg5 group and Abraxane group against paclitaxel-resistant human breast cancer cell line (MCF-7/T).

Figure 40:
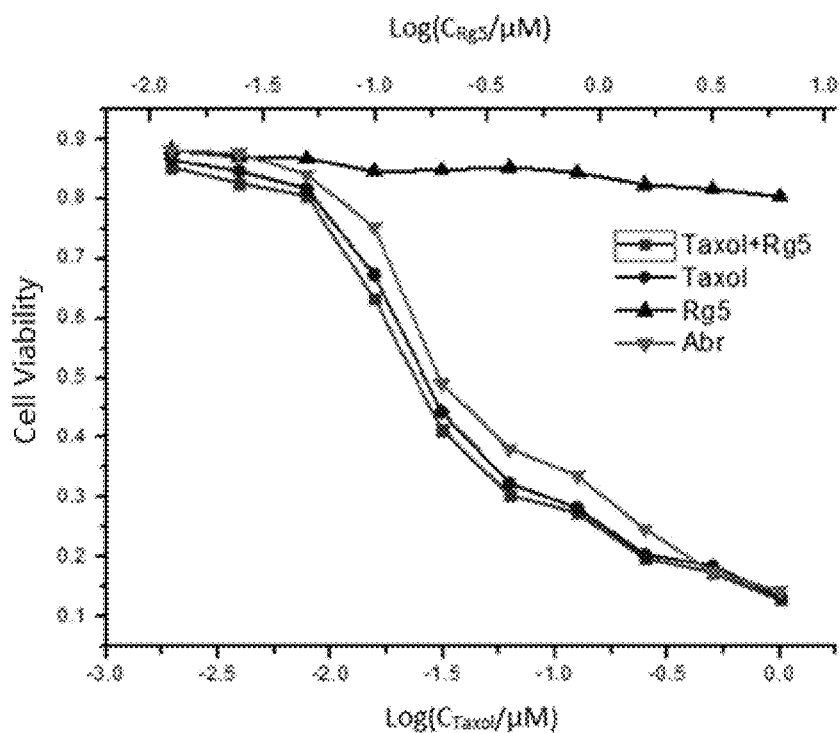

FIG. 40 is a cell survival rate graph of Taxol, blank Rg5, Taxol+Rg5 and Abraxane against human ovarian cancer cell line (A2780).

Figure 41:
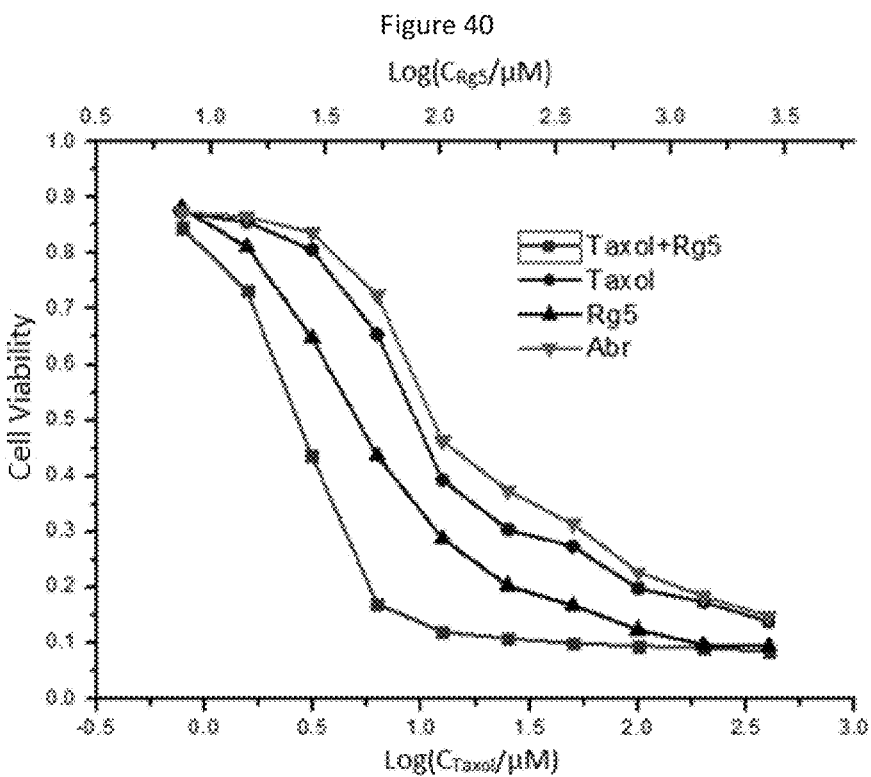

FIG. 41 is a cell survival rate graph of Taxol, blank Rg5, Taxol+Rg5 and Abraxane against paclitaxel-resistant human ovarian cancer cell line (A2780/T).

Figure 42:
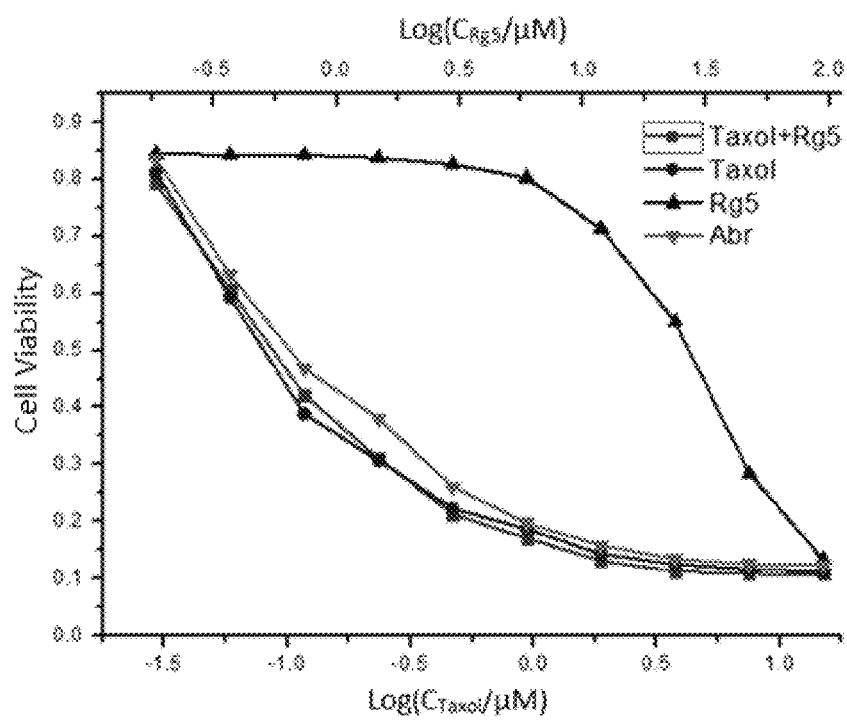

FIG. 42 is a cell survival rate graph of Taxol, blank Rg5, Taxol+Rg5 and Abraxane against human prostate cancer cell line (PC-3).

Figure 43:
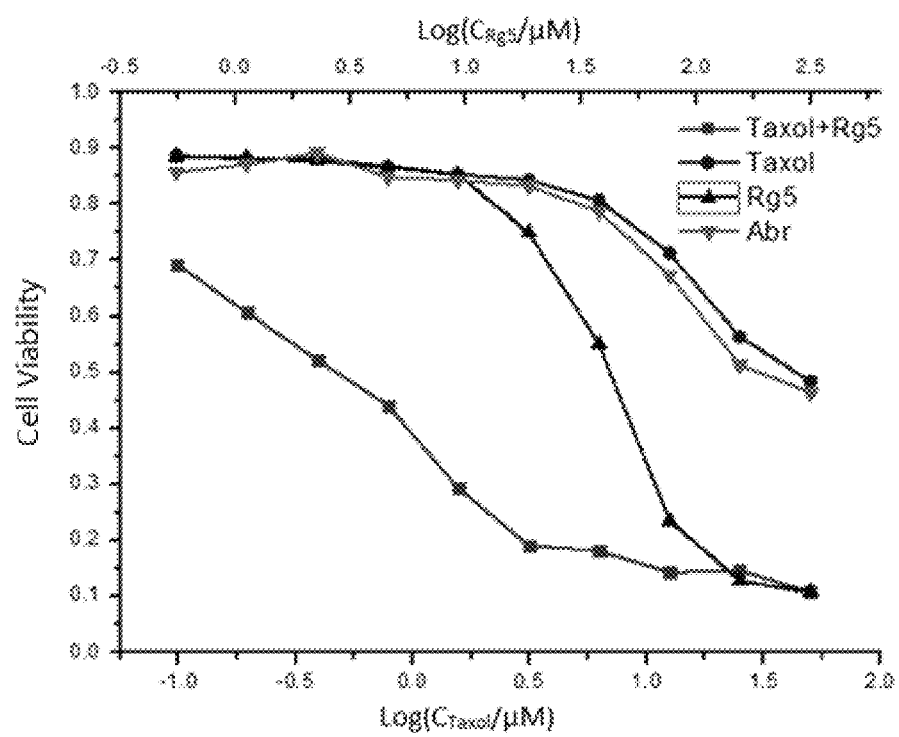

FIG. 43 is a cell survival rate graph of Taxol, blank Rg5, Taxol+Rg5 and Abraxane against paclitaxel-resistant human prostate cancer cell line (PC-3/T).

Figure 44:
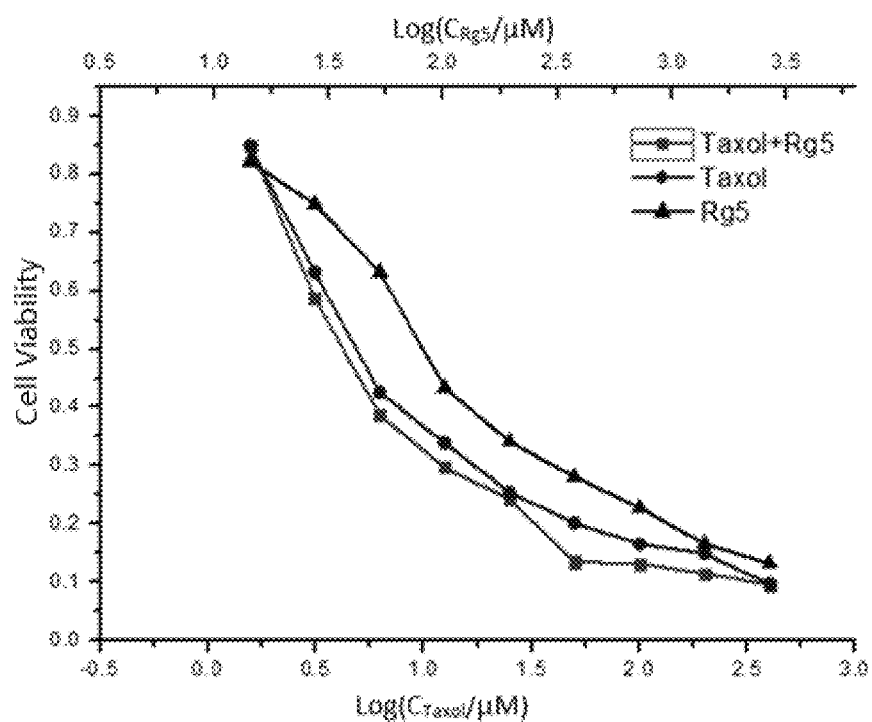

FIG. 44 is a cell survival rate graph of Taxol, blank Rg5 and Taxol+Rg5 against human pancreatic cancer cell line (BxPC-3).

Figure 45:
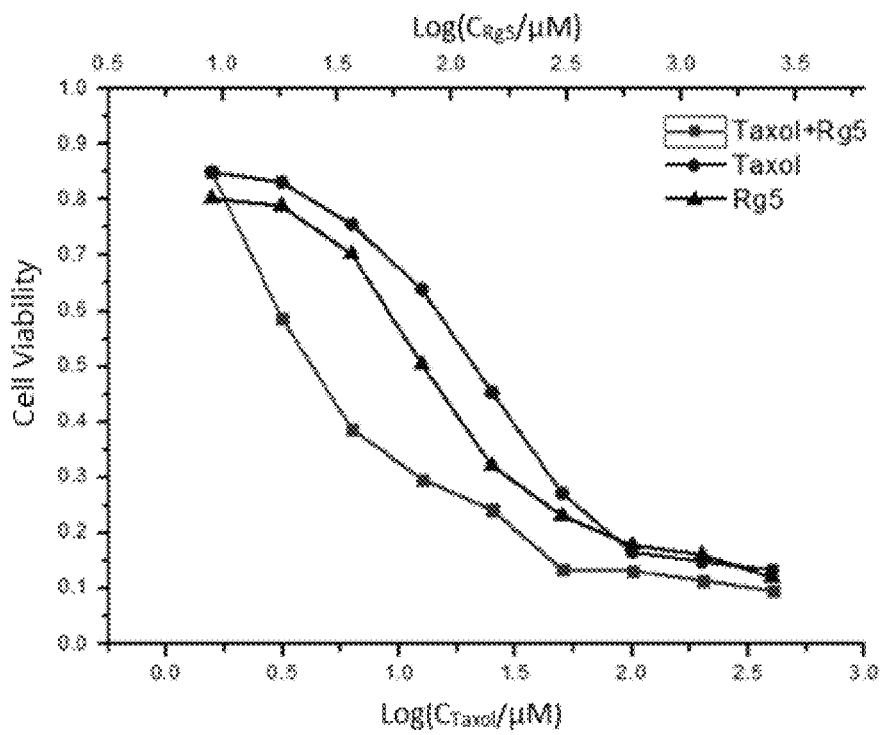

FIG. 45 is a cell survival rate graph of Taxol, blank Rg5 and Taxol+Rg5 against paclitaxel-resistant human pancreatic cancer cell line (BxPC-3/T).

Figure 46:
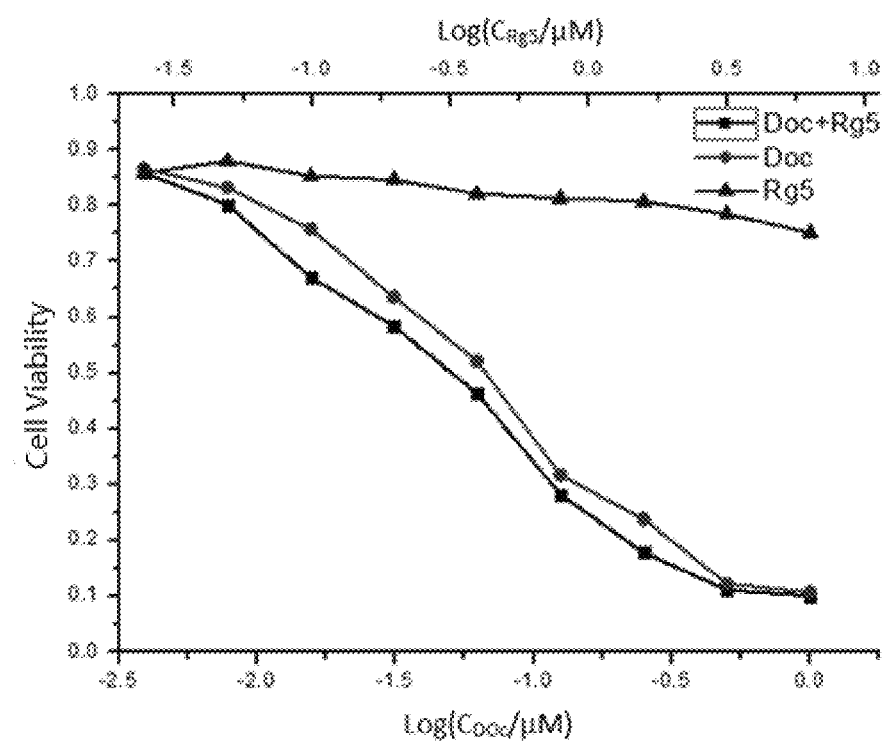

FIG. 46 is a cell survival rate graph of Doc, blank Rg5 and Doc+Rg5 against human breast cancer cell line (MCF-7).

Figure 47:
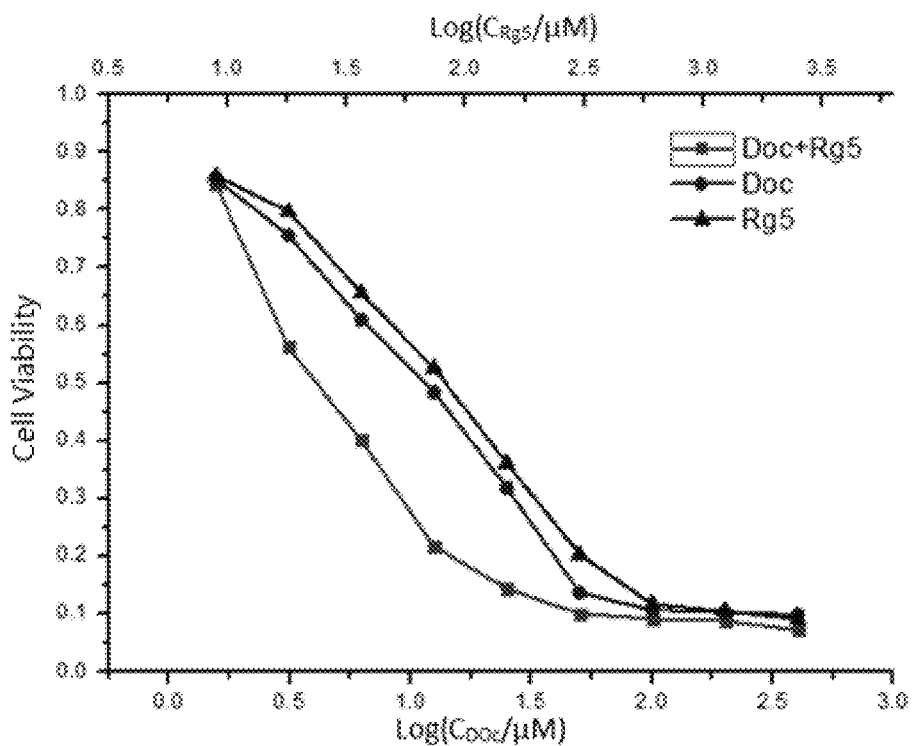

FIG. 47 is a cell survival rate graph of Doc, blank Rg5 and Doc+Rg5 against paclitaxel-resistant human breast cancer cell line (MCF-7/T).

Figure 48:
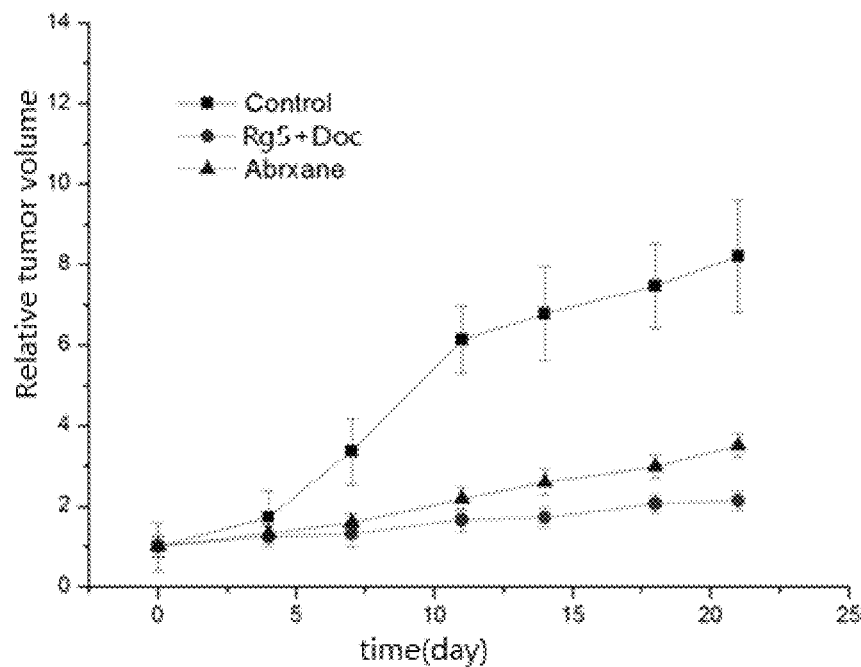

FIG. 48 is an antitumor graph of the control group, Doc+Rg5 group and Abraxane group against breast cancer cell line (MCF-7).

Figure 49:
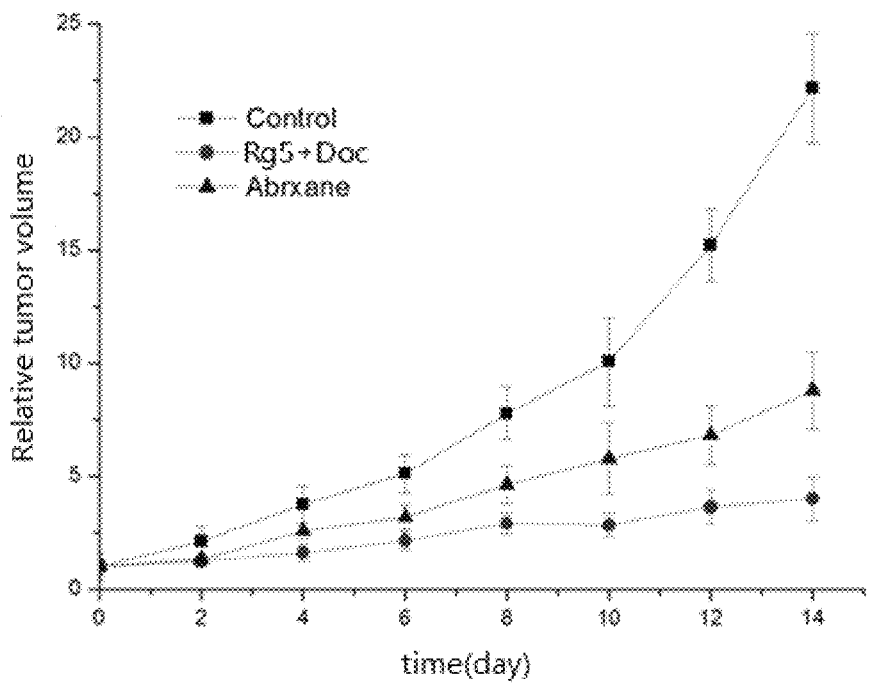

FIG. 49 is an antitumor graph of the control group, Doc+Rg5 group and Abraxane group against paclitaxel-resistant human breast cancer cell line (MCF-7/T).

Figure 50:
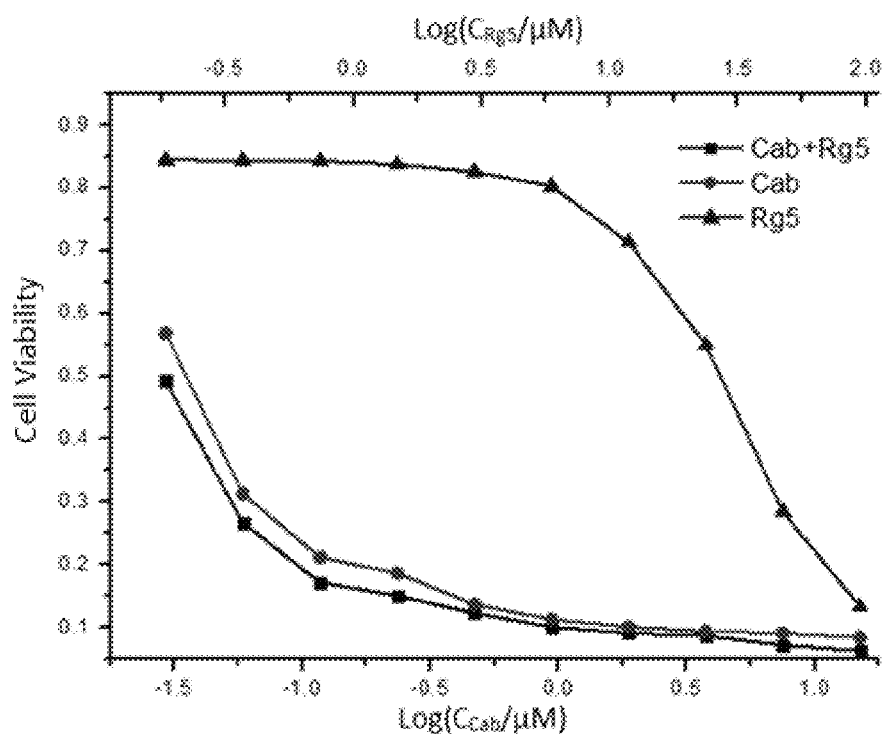

FIG. 50 is a cell survival rate graph of Cab, blank Rg5 and Cab+Rg5 against human prostate cancer cell line (PC-3).

Figure 51:
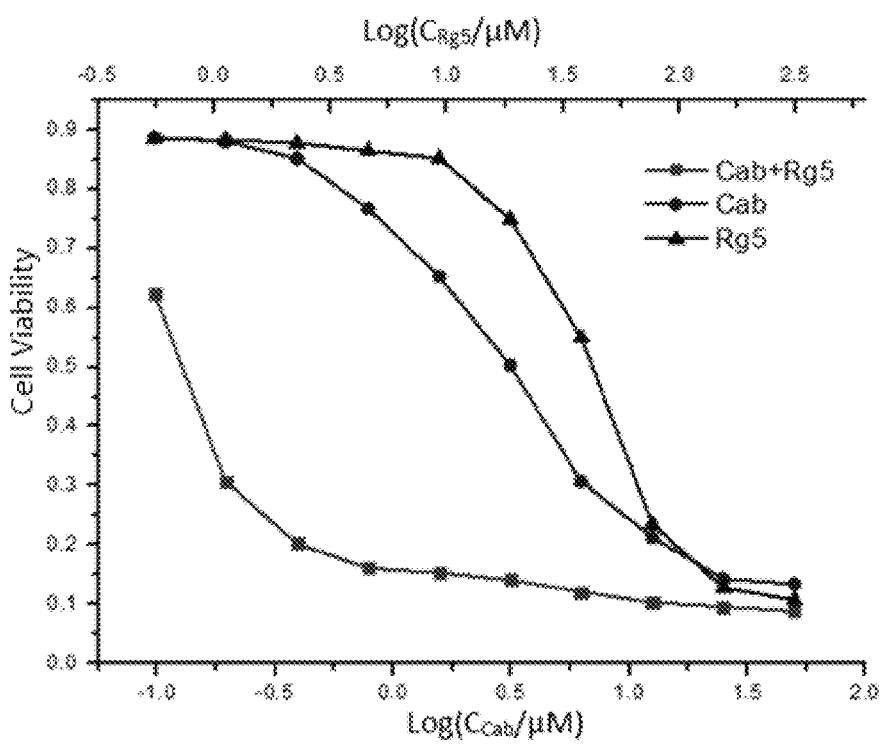

FIG. 51 is a cell survival rate graph of Cab, blank Rg5 and Cab+Rg5 against paclitaxel-resistant human prostate cancer cell line (PC-3/T).

Figure 52:
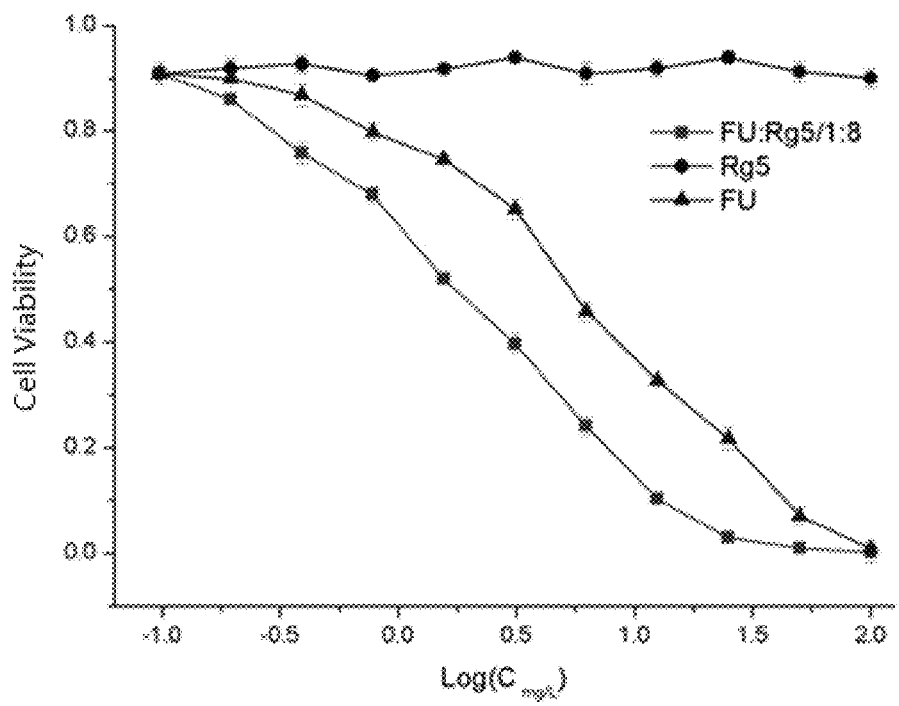

FIG. 52 is a cell survival rate graph of FU+Rg5, blank Rg5 and FU against fluorouracil-resistant human liver cancer cell line (Bel/FU).

Figure 53:
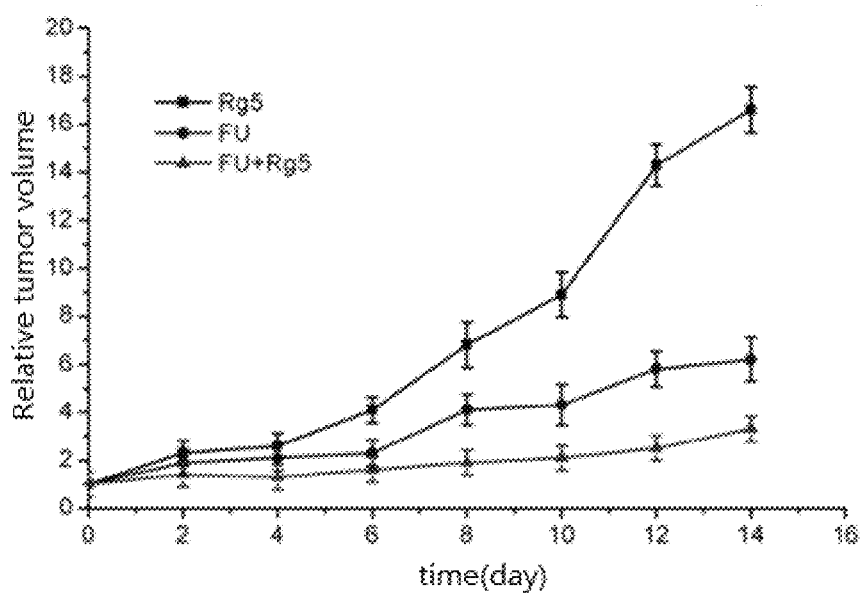

FIG. 53 is an antitumor graph of the blank Rg5, FU and FU+Rg5 against fluorouracil-resistant human liver cancer cell line (Bel/FU).

Figure 54:
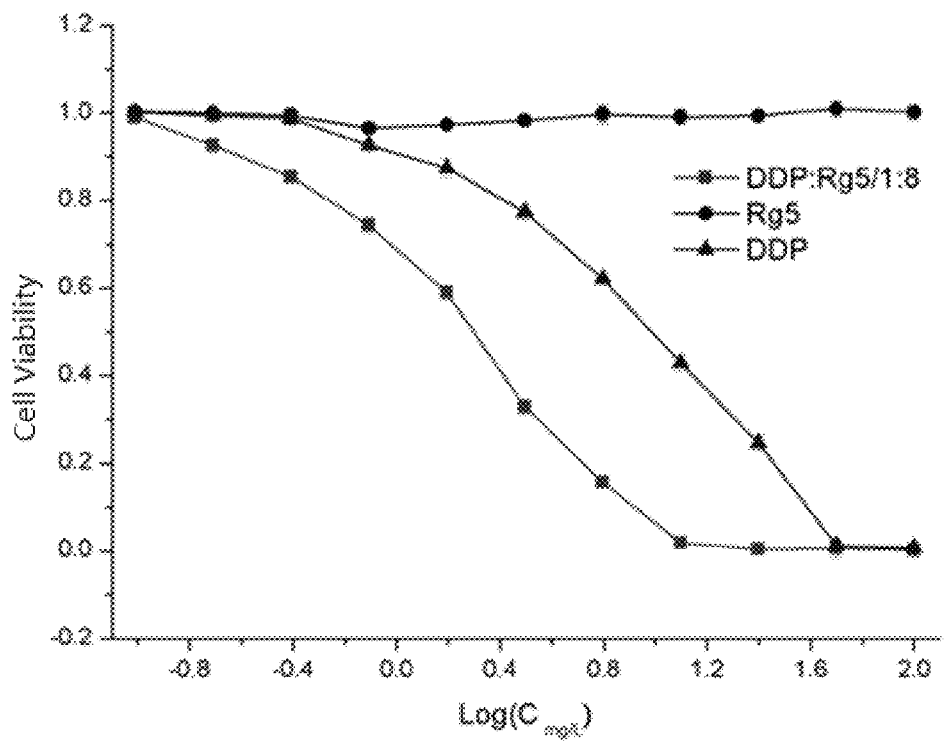

FIG. 54 is a cell survival rate graph of blank Rg5, DDP and DDP+Rg5 against cisplatin-resistant human gastric cancer cell line (SGC-7901/DDP).

Figure 55:
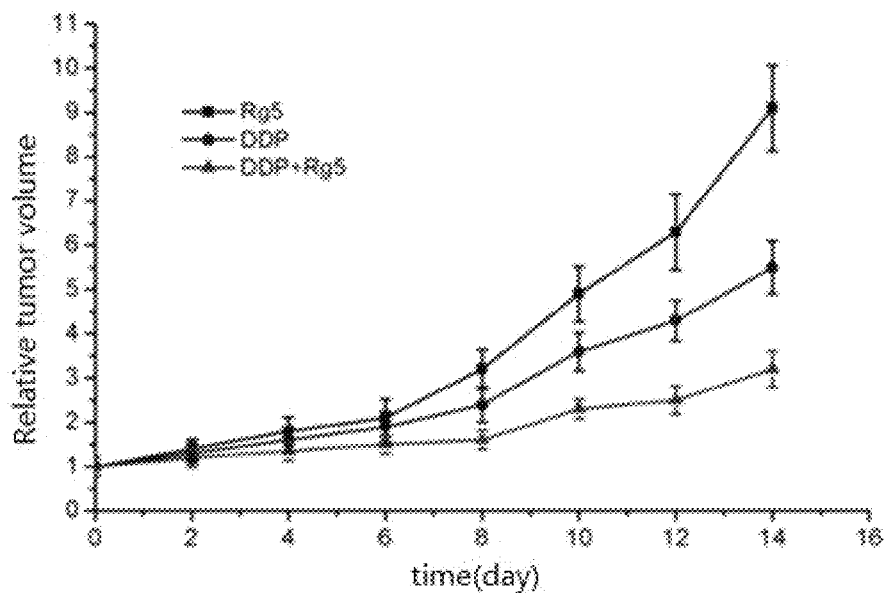

FIG. 55 is an antitumor graph of the blank Rg5, DDP and DDP+Rg5 against cisplatin-resistant human gastric cancer cell line (SGC-7901/DDP).

Figure 56:
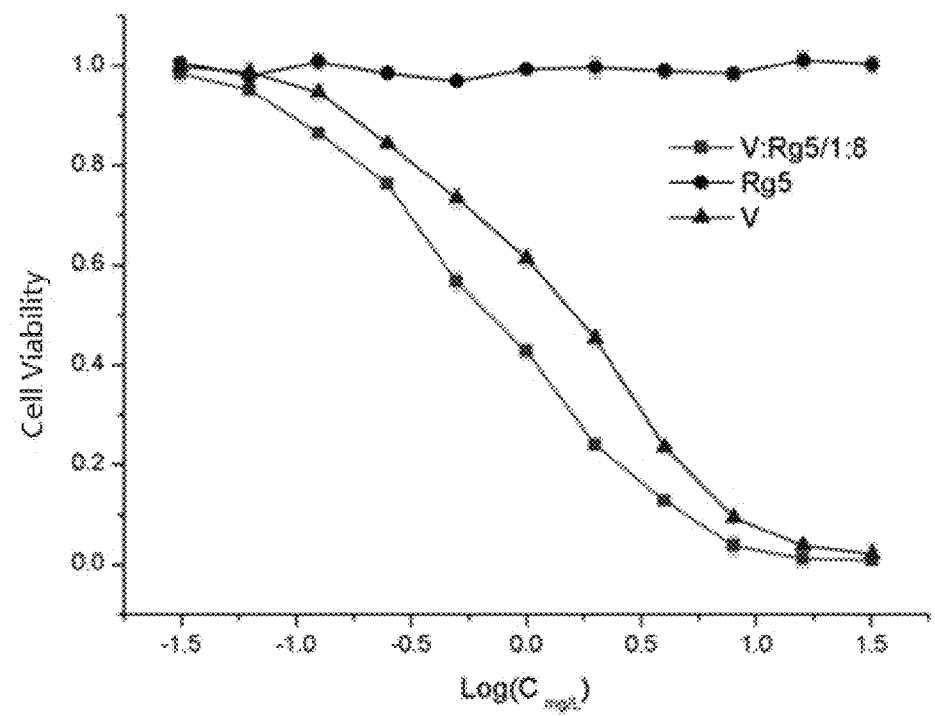

FIG. 56 is a cell survival rate graph of blank Rg5, V and V+Rg5 against vincristine-resistant human colon cancer cell line (HCT-8/V).

Figure 57:
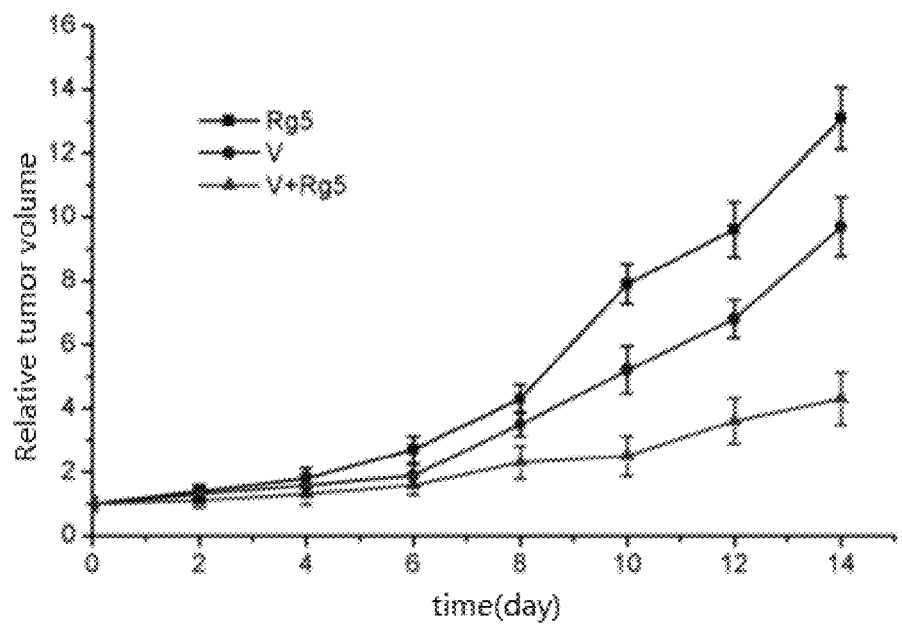

FIG. 57 is an antitumor graph of the blank Rg5, V and V+Rg5 against vincristine-resistant human colon cancer cell line (HCT-8/V).

Figure 58:
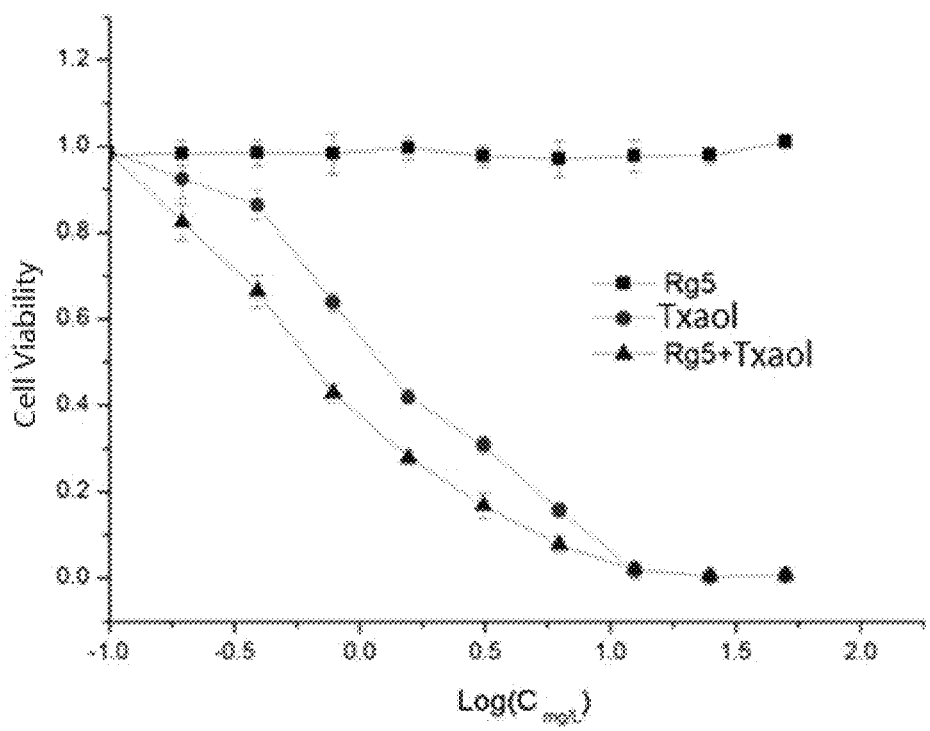

FIG. 58 is a cell survival rate graph of blank Rg5, Taxol and Rg5+Taxol against human gastric cancer cell line (SGC-7901).

Figure 59:
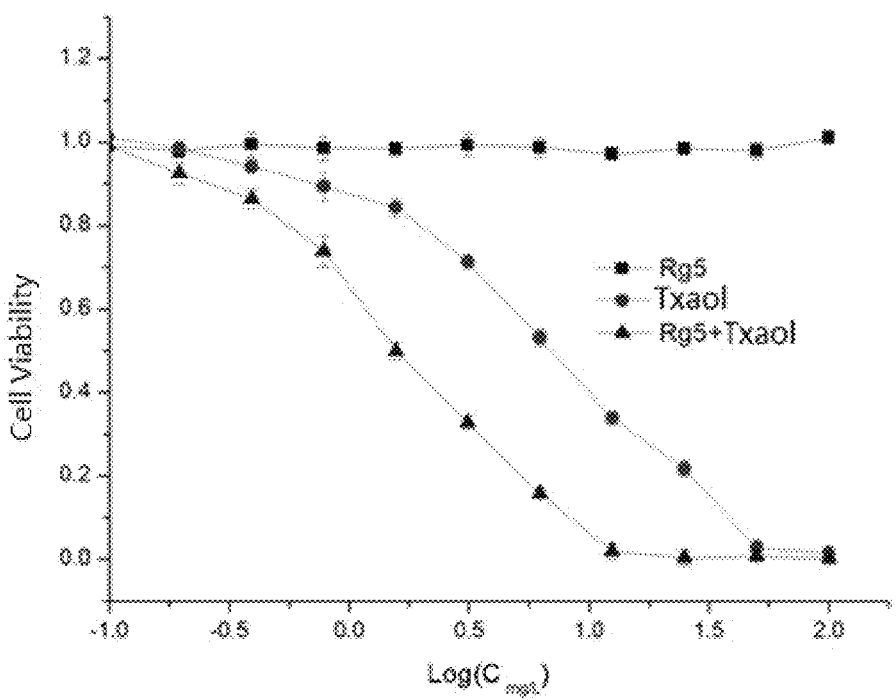

FIG. 59 is a cell survival rate graph of blank Rg5, Taxol and Rg5+Taxol against paclitaxel-resistant human gastric cancer cell line (SGC-7901/T).

Figure 60:
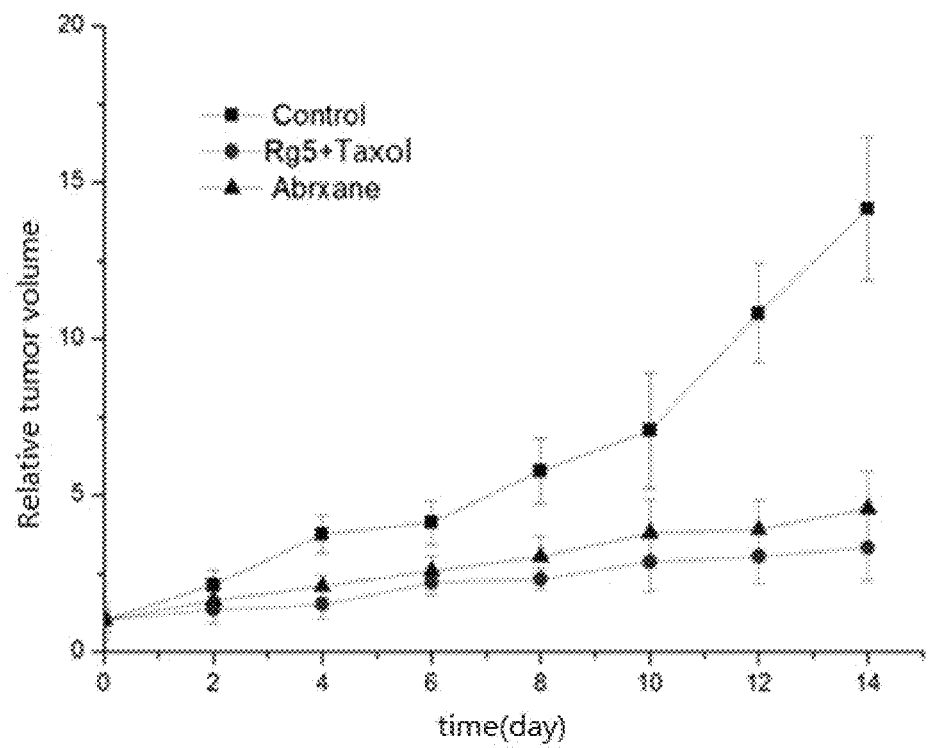

FIG. 60 is an antitumor graph of control group, Abraxane group and Rg5+Taxol group against human gastric cancer cell line (SGC-7901).

Figure 61:
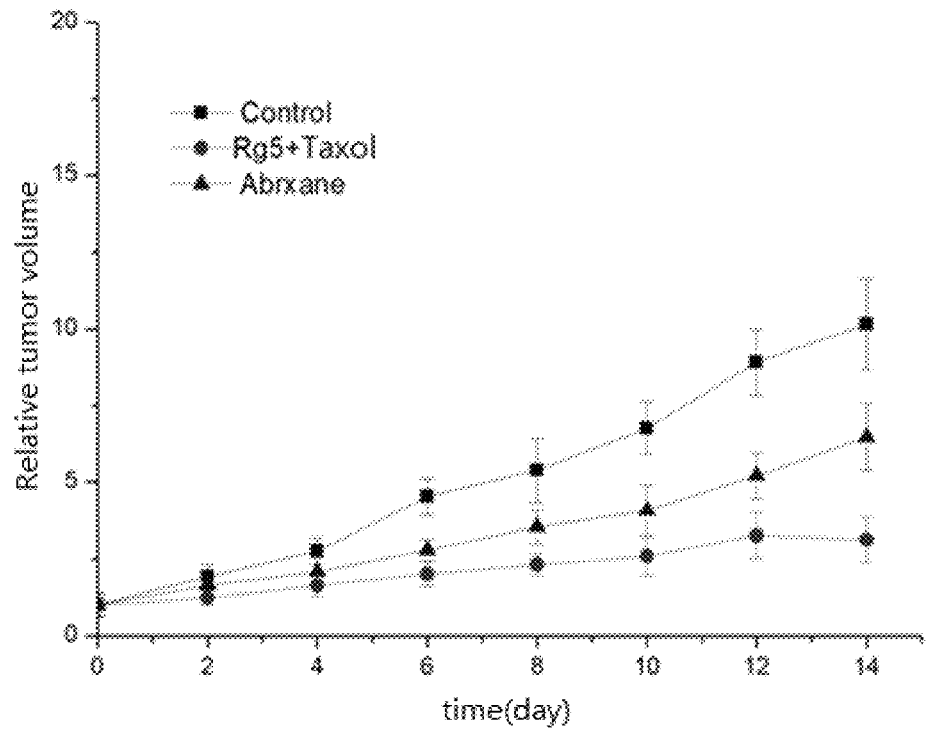

FIG. 61 is an antitumor graph of control group, Abraxane group and Rg5+Taxol group against paclitaxel-resistant human gastric cancer cell line (SGC-7901/T).

DETAILED DESCRIPTION OF THE INVENTION

The present invention is further illustrated by the following embodiments, but not limited by the following embodiments thereby. In the following embodiments, the experimental methods without giving specific condition, are carried out according to conventional ways and conditions or commodity specification.

1. Experimental drugs: ginsenoside Rg5, ginsenoside Rh2, ginsenoside Rg3, ginsenoside Rk1, Paclitaxel, docetaxel, cabazitaxel, cisplatin, oxaliplatin, irinotecan hydrochloride, hydroxycamptothecine, doxorubicin hydrochloride, amphotericin B, epirubicin hydrochloride, vincristine sulfate, fluorouracil are commercially available in this field, for example which are supplied by Shanghai Ginposome Pharma Tech Co., Ltd.

Conventional SiRNA is supplied by RiboBio.

The process for preparing a conventional blank liposome: Soy lecithin 1 g, cholesterol 0.6 g, soybean oil 0.1 g were added into 20 mL chloroform and stirred to form a clear solution at room temperature. The organic solvent was removed by a rotary evaporation in a thermostatic water bath at 40 to 50° C. to form a film, and 20 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron, and filtered through a 0.22 micron microporous membrane to obtain an aqueous solution containing the conventional blank liposome, then split charging into vials and each vial contained 180 mg liposome. The aqueous solution was placed in a freeze-dryer to freeze dry 72 hours, and the protective gas (argon or nitrogen) was introduced, sealed to give the conventional blank liposome.

2. The instruments used in the following embodiments and the application embodiments are self-owned by College of Pharmacy of Southwest University, the model and source information of the instruments are as follows:

High performance liquid chromatography (Agilent 1100),
Electronic balance (TB-215, Denver Instrument, US),
Ultrasonic cleaner (SB3200DT, Ningbo new MacBook Biotechnology Co., Ltd.)
Termovap Sample Concentrator (HGC-12A, Tianjin Hengao Technology Development Co., Ltd.)
Rotary evaporator (RE-2000A, Shanghai Yarong Biochemical Instrument Factory)
Ultra-pure water production system (ULUP-IV-10T, Sichuan U & P Ultra Technology Co., Ltd.)
Thermostatic oscillator (SHA-C, Changzhou Aohua Instrument Co., Ltd.)
Ultrasonic cell crusher (JY92-II, Ningbo new MacBook Biotechnology Co., Ltd.)
High pressure homogenizer (B15, AVESTIN, Canada)
Laser particle size analyzer (Nano ZS, Malvern instruments Ltd. England)
Miniature extruder (Mini-extruder, Avanti Polar Lipids Inc)
Photoelectric Microscope (XDS-1B, Chongqing Optical Instrument Co., Ltd.)
Clean bench (SW-CJ-1FD, Suzhou Aetna air Technology Co., Ltd.)
Cell incubator (CCL-170B-8, ESCO, Singapore)
Fluorescence inverted microscope (IX-73, Olympus, Japan)
Small animal imaging system in vivo (FX PRO, Bruker Corporation, US)

3. Experimental cell lines:

A549 human lung cancer cell line (Nanjing KeyGEN Bio)

A549/T paclitaxel-resistant human lung cancer cell line (Nanjing KeyGEN Bio)

MCF-7 human breast cancer cell line (Nanjing KeyGEN Bio)

A2780 human ovarian cancer cell line (Nanjing KeyGEN Bio)

A2780/T paclitaxel-resistant human ovarian cancer cell line (Nanjing KeyGEN Bio)

PC-3 human prostate cancer cell line (Nanjing KeyGEN Bio)

BxPC-3 human pancreatic cancer cell line (Nanjing KeyGEN Bio)

Bel/FU fluorouracil-resistant human liver cancer cell line (Nanjing KeyGEN Bio)

SGC-7901 human gastric cancer cell line (Nanjing KeyGEN Bio)

SGC-7901/DDP cisplatin-resistant human gastric cancer cell line (Nanjing KeyGEN Bio)

HCT-8/V vincristine-resistant human colon cancer cell line (Nanjing KeyGEN Bio)

The process for establishing SGC-7901/T paclitaxel-resistant human gastric cancer cell line:

A low-concentration amount-increasing continuous inducing method was applied to induce parental SGC-7901 cells to establish drug resistant human gastric cancer cell line SGC-7901/paclitaxel. The new recovery SGC-7901 cells were cultured for two generations or three generations under conventional conditions to make the cells grow stably. When the culture-medium was renewed the next day that the cells subcultured through digestion, paclitaxel was added with an initial concentration of one tenth of $IC_{50}$ to parental SGC-7901. The culture-medium was renewed the next day that the drug had been added, and the concentration of paclitaxel was maintained while conventional subculture was carried out. After the cells could stably grow under each concentration of paclitaxel, the concentration of the drug was increased. Continue to culture until cells could stably grow in a culture-medium containing 2.5 mg/L paclitaxel. The period lasted for 12 months.

The process for establishing MCF-7/T paclitaxel-resistant human breast cancer cell line:

A low-concentration amount-increasing continuous inducing method was applied to induce parental MCF-7 cells to establish drug resistant human breast cancer cell line MCF-7/paclitaxel. The new recovery MCF-7 cells were cultured for two generations or three generations under conventional conditions to make the cells grew stably. When the culture-medium was renewed the next day that the cells subcultured through digestion, paclitaxel was added with an initial concentration of one tenth of $IC_{50}$ to parental MCF-7. The culture-medium was renewed the next day that the drug had been added, and the concentration of paclitaxel was maintained while conventional subculture was carried out. After the cells could stably grow under each concentration of paclitaxel, the concentration of the drug was increased. Continued to culture until cells could stably grow in a culture medium containing 2.5 mg/L paclitaxel. The period lasted for 12 months.

The process for establishing PC-3/T paclitaxel-resistant human prostate cancer cell line:

A low-concentration amount-increasing continuous inducing method was applied to induce parental PC-3 cells to establish drug resistant human prostate cancer cell line PC-3/paclitaxel. The new recovery PC-3 cells were cultured for two generations or three generations under conventional conditions to make the cells grow stably. When the culture-medium was renewed the next day that the cells subcultured through digestion, paclitaxel was added with an initial concentration of one tenth of $IC_{50}$ to parental PC-3. The culture-medium was renewed the next day that the drug had been added, and the concentration of paclitaxel was maintained while conventional subculture was carried out. After the cells could stably grow under each concentration of paclitaxel, the concentration of the drug was increased. Continued to culture until cells could stably grow in a culture-medium containing 0.5 mg/L paclitaxel. The period lasted for 10 months.

The process for establishing BxPC-3/T paclitaxel-resistant human pancreatic cancer cell line:

A low-concentration amount-increasing continuous inducing method was applied to induce parental BxPC-3 cells to establish drug resistant human pancreatic cancer cell line BxPC-3/paclitaxel. The new recovery BxPC-3 cells were cultured for two generations or three generations under conventional conditions to make the cells grow stably. When the culture-medium was renewed the next day that the cells subcultured through digestion, paclitaxel was added with an initial concentration of one tenth of $IC_{50}$ to parental BxPC-3. The culture-medium was renewed the next day that the drug had been added, and the concentration of paclitaxel was maintained while conventional subculture was carried out. After the cells could stably grow under each concentration of paclitaxel, the concentration of the drug was increased. Continued to culture until cells could stably grow in a culture-medium containing 3 mg/L paclitaxel. The period lasted for 12 months.

4. Experimental animals: Kunming mice (or named normal mice), which were purchased from the Animal Center of the Third Military Medical University, BALB/C-nu/nu mice (or named nude mice), which were purchased from Shanghai Slack Laboratory Animal Co., Ltd.

5. Cell Culture method: the related cell line was placed into a 37° C. incubator containing 5% $CO_2$, and cultured by DMEM or RPMI1640 complete culture-medium (containing 10% fetal bovine serum, 100 U/mL penicillin, 100 µg/mL streptomycin), 0.25% trypsin-EDTA was used to digest and subculture 2 to 3 times per week.

6. Administration: a negative control group, a positive control group (e.g. ginsenoside blank liposome control group, paclitaxel control group, conventional liposome-paclitaxel control group, or albumin-paclitaxel control group) and a ginsenoside liposome loading a drug group are set for each experiment. No less than 6 concentration gradients are set, half dilution or 5 times dilution, 3 wells for each concentration.

7. Assay of inhibition concentration $IC_{50}$ of the tumor cell: tumor cells at logarithmic growth phase were digested with trypsin thereby giving cell sap with a certain concentration, then inoculated into a 96-well plate with a density of 5000 cells per well, 100 µl for each well. A fresh culture-medium containing different concentration of sample and corresponding solvent control were added, 100 µl for each well (a final concentration of DMSO <0.5%). Each sample set 10 dose groups, each group set 3 parallel wells, removing the supernatant after cultured for 72 h in an incubator at 37° C. 100 µl PBS and 10 µl CCK-8 were added to each well, shaked by a micro oscillator to become uniform, continued to culture for 3 h. An optical density (OD) is determined by a microplate reader at a reference wavelength of 630 nm and a detection wavelength of 450 nm. Tumor cells treated with a solvent were as a control group, $IC_{50}$ was calculated according to an equation of the median effect.

8. Assay of cell experiment in vitro: tumor cells at logarithmic growth phase were collected, resuspended in a DMEM complete culture-medium (containing 10% fetal bovine serum, 100 U/ml penicillin, 100 μg/ml streptomycin) and a final concentration was $4 \times 10^4$ cells/ml. In a 96-well cell culture plate, 200 μl above cell suspension was added into each well ($8 \times 10^3$ cells/well), and cultured for 48 h in a cell incubator at 37° C. filled with 5% $CO_2$. The DMEM complete culture-medium was respectively replaced with 200 μL antitumor drug with different concentrations. The final concentrations of the drugs were set no less than six groups. The DMEM complete culture-medium was as the negative control group. Each concentration was set 4 wells and the experiment was repeated for 3 times. 20 μl 5 mg/mL MTT solution was added into each well after the cells were cultured for 72 h in a cell incubator at 37° C. filled with 5% $CO_2$. The supernatant was discarded after it was further cultured for 4 h in a cell incubator. 150 μl DMSO was added into each well, shaked for 10 min. An OD was determined at 490 nm by a continuous spectrum multifunctional microplate reader (Tecan infinite M 200 TECAN, Switzerland). The cell survival rate was calculated by the following formula: (the cell survival rate (%)=$OD_{drug}/OD_{control} \times$ 100%).

Cell survival rate (%)=$OD_{490(sample)}/OD_{490(control)} \times$ 100%;

Wherein $OD_{490(sample)}$ is the OD of the experimental group, $OD_{490(control)}$ is the OD of the blank control group.

9. Assay of pharmacological efficacy experiment in vivo: $1 \times 10^7$ to $10 \times 10^7$ cells/mL of tumor cell at logarithmic growth phase was injected subcutaneously in right armpit of an 18 to 20 g nude mouse slowly by a 1 mL syringe, each nude mouse was injected with 100 μl. The growth of the tumor was observed until the volume of the tumor was about 100 $mm^3$. Animals were randomly grouped and administered. The mice were weighed and the volume of the tumor was measured every two days. The longest diameter and the shortest diameter of the tumor were measured with a vernier caliper. The nude mouse was sacrificed and the volume of tumor was measured. The relative tumor volume (RTV), the relative tumor proliferation rate (T/C) and the inhibition percentage of tumor were calculated for statistical analysis.

The calculation formula of the tumor volume: V=abh/2, wherein a is the diameter of the tumor, b is the transverse diameter of the tumor, h is the height of the tumor.

The calculation formula of the relative tumor volume: RTV=Vt/V0, wherein Vt is the volume of the tumor at a certain time, V0 is the volume of the tumor at the time of administration.

The calculation formula of the relative tumor proliferation rate: T/C (%)=TRTV/CRTV×100%, wherein TRTV is the RTV of the treatment group, CRTV is the RTV of the solvent control group.

The calculation formula of the tumor inhibition percentage: the tumor inhibition percentage=(the tumor weight of the solvent control group–the tumor weight of the drug administration group)/the tumor weight of the solvent control group×100%.

The valuation standard of curative effect: T/C (%)>60 indicates no effect; T/C (%)≤60 and compared to the solvent control group, P<0.05 when the tumor volume is processed with statistics indicates having effect.

In the following embodiments, the temperature and the pressure for the operation, unless otherwise specified, generally refer to room temperature and ordinary pressure, wherein room temperature refers to 10 to 30° C.; ordinary pressure refers to a standard atmospheric pressure.

Embodiment 1 The Preparation of Ginsenoside Rg5 Blank Liposome

Figure 1:
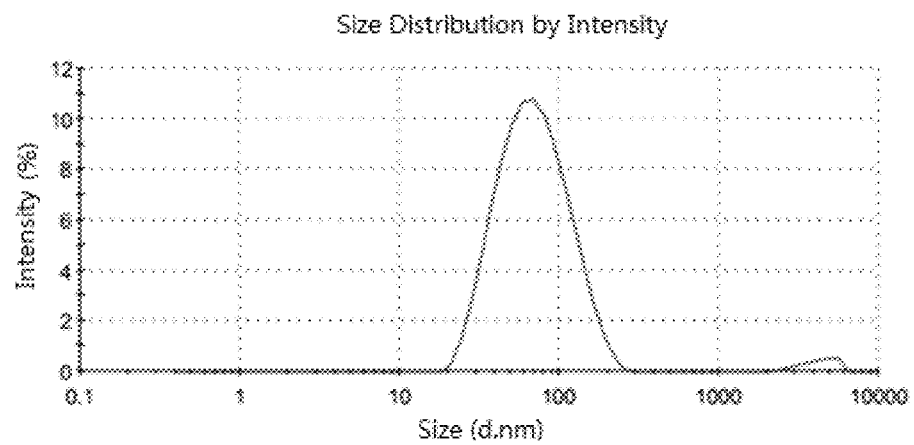
FIG. 1 is a particle size distribution figure of the ginsenoside Rg5 blank liposome prepared by embodiment 1.

Soybean lecithin 1 g, ginsenoside Rg5 0.6 g and soybean oil 0.1 g were added into 20 mL chloroform and stirred to form a clear solution at room temperature. The organic solvent was removed by a rotary evaporation in a thermostatic water bath at 40 to 50° C. to form a film, and 20 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 blank liposome. Then the aqueous solution was split charging into vials and each vial contained 180 mg liposome. The aqueous solution was placed in a freeze-dryer to freeze dry for 72 hours, then protective gas (argon or nitrogen) was introduced, sealed to give the ginsenoside Rg5 blank liposome. By test, the average particle size of the liposome was 57.43 nm (see Table 1 and FIG. 1).

TABLE 1

Particle size, distribution of particle size, intensity and width of the ginsenoside Rg5 blank liposome

| / | Particle size (d · nm) | Intensity (%) | Width (d · nm) |
|---|---|---|---|
| Peak 1 | 76.02 | 97.6 | 38.63 |
| Peak 2 | 4227 | 2.4 | 994.4 |
| Peak 3 | 0.000 | 0.0 | 0.000 |
| Average particle size (Z-Averaged.nm) | | 57.43 | |
| Polydispersity index (Pdl) | | 0.273 | |
| Intercept | | 0.934 | |
| Result quality | | good | |

Embodiment 2 The Preparation of Ginsenoside Rg5 Paclitaxel Liposome

Figure 2:
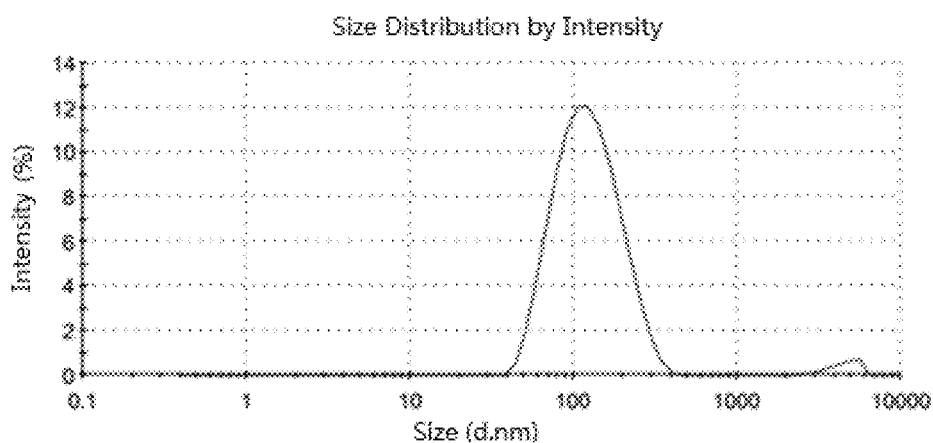
FIG. 2 is a particle size distribution figure of the ginsenoside Rg5 paclitaxel liposome prepared by embodiment 2.

Soybean lecithin 1 g, ginsenoside Rg5 0.6 g and paclitaxel 0.3 g were added into 20 mL acetonitrile and stirred to form a clear solution at room temperature. The organic solvent was removed by a rotary evaporation in a thermostatic water bath at 50 to 60° C. to form a film, and 20 mL purified water was added. An operation of ultrasound was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 113.6 nm (see Table 2 and FIG. 2). The encapsulated efficiency was more than 90%.

TABLE 2

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 131.2 | 97.4 | 58.95 |
| Peak 2 | 4514 | 2.6 | 871.1 |
| Peak 3 | 0.000 | 0.0 | 0.000 |
| Average particle size (Z-Averaged.nm) | | 113.6 | |
| Polydispersity index (Pdl) | | 0.210 | |
| Intercept | | 0.940 | |
| Result quality | | good | |

Embodiment 3 The Preparation of Ginsenoside Rg5 Paclitaxel Liposome

Figure 3:
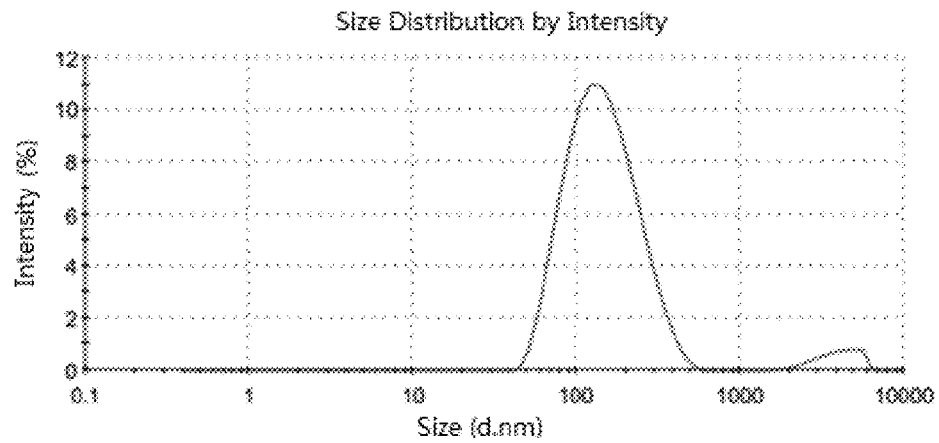
FIG. 3 is a particle size distribution figure of the ginsenoside Rg5 paclitaxel liposome prepared by embodiment 3.

Egg lecithin 0.75 g, ginsenoside Rg5 0.6 g, paclitaxel 0.2 g, cholesterol 0.25 g and threonine 0.25 g were added into 20 mL methanol and stirred to form a clear solution at room temperature. The organic solvent was removed by a rotary evaporation in a thermostatic water bath at 60 to 70° C. to form a film, and 20 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 132.6 nm (see Table 3 and FIG. 3). The encapsulated efficiency was more than 90%.

TABLE 3

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 156.9 | 95.5 | 78.12 |
| Peak 2 | 3983 | 4.5 | 1088 |
| Peak 3 | 0.000 | 0.0 | 0.000 |
| Average particle size (Z-Averaged.nm) | | 132.6 | |
| Polydispersity index (Pdl) | | 0.253 | |
| Intercept | | 0.922 | |
| Result quality | | good | |

Embodiment 4 The Preparation of Ginsenoside Rg5 Paclitaxel Liposome

Figure 4:
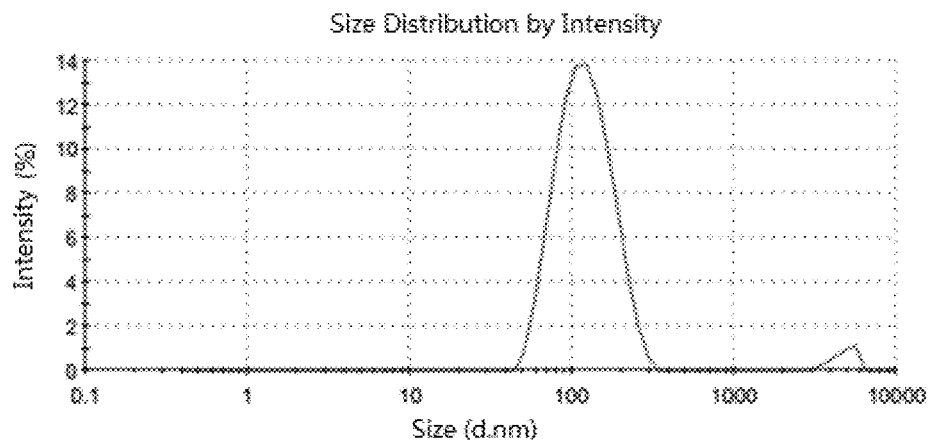
FIG. 4 is a particle size distribution figure of the ginsenoside Rg5 paclitaxel liposome prepared by embodiment 4.

Soybean lecithin 8 g, ginsenoside Rg5 6 g, paclitaxel 1 g, soybean oil 4 g and vitamin C 2.5 g were added into 200 mL ethanol and stirred to form a clear solution at room temperature. The organic solvent was removed by a film evaporator at 60 to 70° C. to form a film, and 200 mL 10% trehalose aqueous solution (the percentage refers to the mass of the trehalose relative to the total mass of the trehalose aqueous solution) was added. An operation of homogenization by a high pressure homogenizer was carried out until the particle size of liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 116.4 nm (see Table 4 and FIG. 4). The encapsulated efficiency was more than 90%.

TABLE 4

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 125.7 | 96.7 | 47.69 |
| Peak 2 | 4749 | 3.3 | 749.0 |
| Peak 3 | 0.000 | 0.0 | 0.000 |
| Average particle size (Z-Averaged.nm) | | 116.4 | |
| Polydispersity index (Pdl) | | 0.212 | |
| Intercept | | 0.943 | |
| Result quality | | good | |

Embodiment 5 The Preparation of Ginsenoside Rg5 Paclitaxel Liposome

Figure 5:
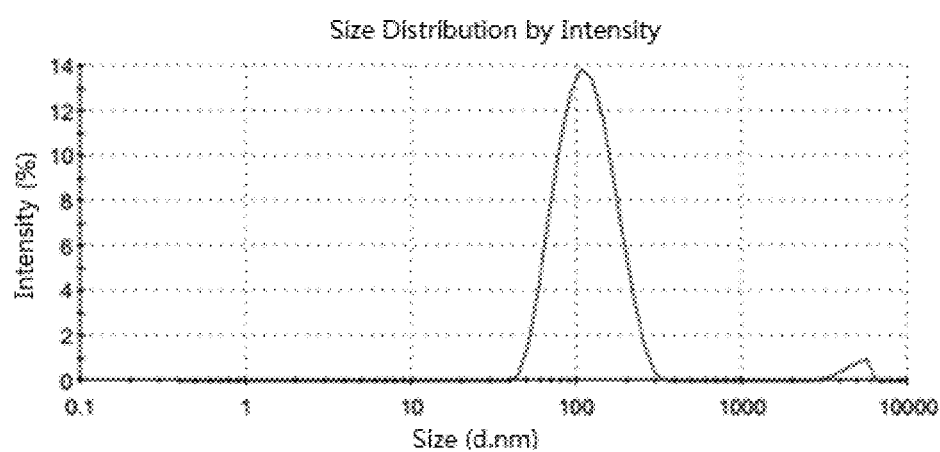
FIG. 5 is a particle size distribution figure of the ginsenoside Rg5 paclitaxel liposome prepared by embodiment 5.

Soybean lecithin 7 g, ginsenoside Rg5 6 g, paclitaxel 2 g, soybean oil 4 g, cholesterol 2.5 g and vitamin E 0.5 g were added into 200 mL diethyl ether and stirred to form a clear solution at room temperature. The organic solvent was removed by a film evaporator at 30 to 40° C. to form a film, and 200 mL 5% saccharose aqueous solution (the percentage refers to the mass of the saccharose relative to the total mass of the saccharose aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 109.8 nm (see Table 5 and FIG. 5). The encapsulated efficiency was more than 90%.

TABLE 5

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 119.9 | 97.3 | 46.33 |
| Peak 2 | 4752 | 2.7 | 747.0 |
| Peak 3 | 0.000 | 0.0 | 0.000 |
| Average particle size (Z-Averaged.nm) | | 109.8 | |
| Polydispersity index (Pdl) | | 0.201 | |
| Intercept | | 0.967 | |
| Result quality | | good | |

Embodiment 6 The Preparation of Ginsenoside Rg5 Paclitaxel Liposome

Figure 6:
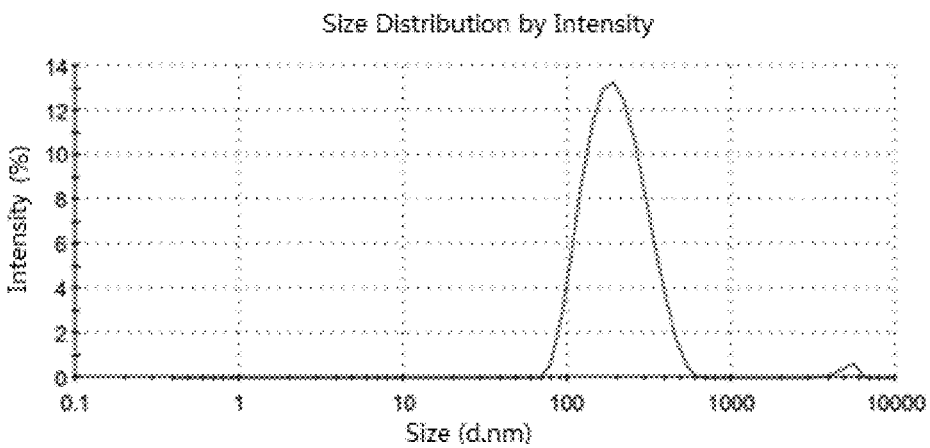
FIG. 6 is a particle size distribution figure of the ginsenoside Rg5 paclitaxel liposome prepared by embodiment 6.

HSPC 8 g, ginsenoside Rg5 6 g, paclitaxel 2 g, soybean oil 4 g and vitamin E 0.5 g were added into 200 mL chloroform and stirred to form a clear solution at room temperature. The organic solvent was removed by a film evaporator at 35 to 45° C. to form a film, and 200 mL 5% mannitol aqueous solution (the percentage refers to the mass of the mannitol relative to the total mass of the mannitol aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 186.7 nm (see Table 6 and FIG. 6). The encapsulated efficiency was more than 90%.

TABLE 6

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 209.8 | 98.6 | 87.28 |
| Peak 2 | 5015 | 1.4 | 600.9 |
| Peak 3 | 0.000 | 0.0 | 0.000 |
| Average particle size (Z-Averaged.nm) | | 186.7 | |
| Polydispersity index (Pdl) | | 0.176 | |
| Intercept | | 0.950 | |
| Result quality | | good | |

Embodiment 7 The Preparation of Ginsenoside Rg5 Paclitaxel Liposome

Figure 7:
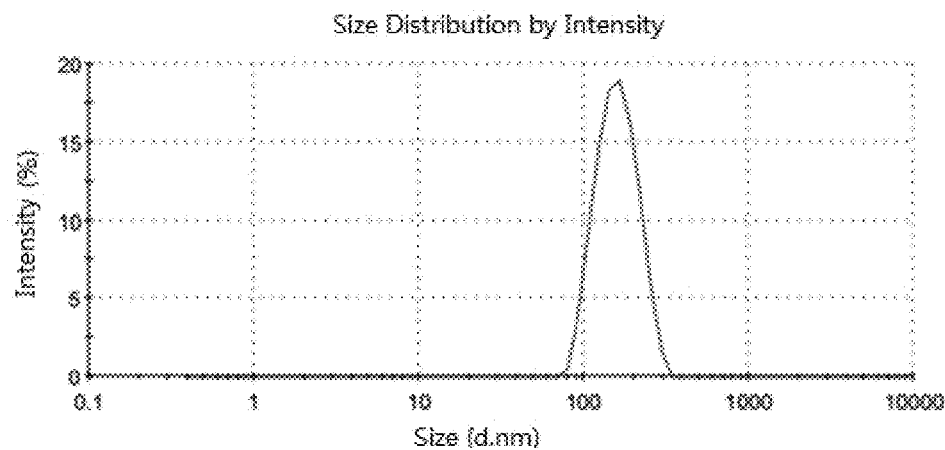
FIG. 7 is a particle size distribution figure of the ginsenoside Rg5 paclitaxel liposome prepared by embodiment 7.

DMPC 8 g, ginsenoside Rg5 6 g, paclitaxel 1 g, soybean oil 4 g and ascorbic acid 0.1 g were added into 200 mL ethanol and stirred to form a clear solution at 55 to 65° C. The organic solvent was removed by a film evaporator at 60 to 70° C. to form a film, and 200 mL 5% xylitol aqueous solution (the percentage refers to the mass of the xylitol relative to the total mass of the xylitol aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 146.7 nm (see Table 7 and FIG. 7). The encapsulated efficiency was more than 90%.

TABLE 7

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 163.3 | 100.0 | 45.93 |
| Peak 2 | 0.000 | 0.0 | 0.000 |
| Peak 3 | 0.000 | 0.0 | 0.000 |
| Average particle size (Z-Averaged.nm) | | 146.7 | |
| Polydispersity index (Pdl) | | 0.101 | |
| Intercept | | 0.947 | |
| Result quality | | good | |

Embodiment 8 The Preparation of Ginsenoside Rg5 Paclitaxel Liposome

Figure 8:
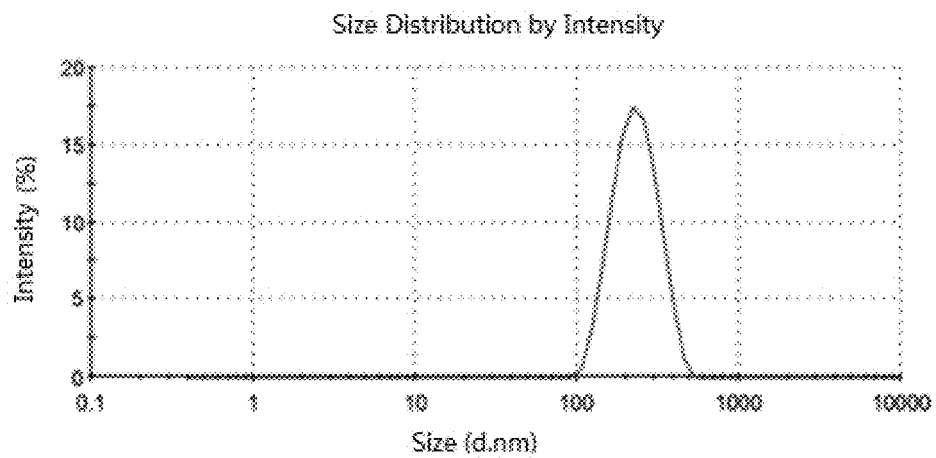
FIG. 8 is a particle size distribution figure of the ginsenoside Rg5 paclitaxel liposome prepared by embodiment 8.

DSPE-PEG(2000) 8 g, ginsenoside Rg5 6 g, paclitaxel 2 g, sodium oleate 4 g and propylene glycol 0.1 g were added into 200 mL chloroform and stirred to form a clear solution at 10 to 20° C. The organic solvent was removed by a film evaporator at 40 to 50° C. to form a film, and 200 mL 5% lactose aqueous solution (the percentage refers to the mass of the lactose relative to the total mass of the lactose aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome. By test, the average particle size of the liposome was 217.2 nm (see Table 8 and FIG. 8). The encapsulated efficiency was more than 90%.

TABLE 8

Particle size, distribution of particle size, intensity and width of the ginsenoside Rg5 paclitaxel liposome

| / | Particle size (d · nm) | Intensity (%) | Width (d · nm) |
|---|---|---|---|
| Peak 1 | 237.4 | 100.0 | 73.02 |
| Peak 2 | 0.000 | 0.0 | 0.000 |
| Peak 3 | 0.000 | 0.0 | 0.000 |
| Average particle size (Z-Averaged.nm) | | 217.2 | |
| Polydispersity index (Pdl) | | 0.219 | |
| Intercept | | 0.975 | |
| Result quality | | good | |

Embodiment 9 The Preparation of Ginsenoside Rg5 Docetaxel Liposome

Figure 9:
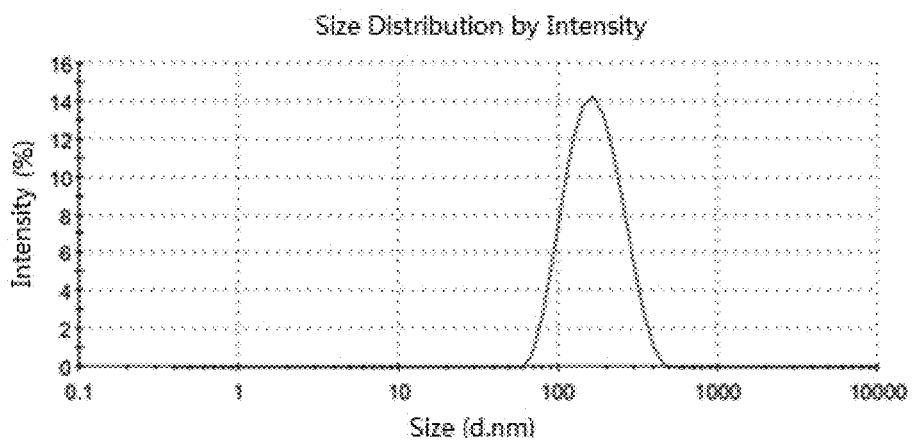
FIG. 9 is a particle size distribution figure of the ginsenoside Rg5 docetaxel liposome prepared by embodiment 9.

Soybean lecithin 0.8 g, ginsenoside Rg5 0.6 g, docetaxel 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution was added. An operation of ultrasound was carried out until the particle size of the liposome was between 0.1 and 0.3 micron. A 0.22 micron microporous membrane was used to filtration thereby obtaining an aqueous solution containing ginsenoside Rg5 docetaxel liposome. Then the aqueous solution was split charging into vials and each vial contained 20 mg docetaxel. The aqueous solution was placed in a freeze-dryer to freeze dry for 72 hours, then protective gas (argon or nitrogen) was introduced, sealed to give the ginsenoside Rg5 docetaxel liposome. By test, the average particle size of the liposome was 158 nm (see Table 9 and FIG. 9). The encapsulated efficiency was more than 90%.

TABLE 9

Particle size, distribution of particle size, intensity and width of the ginsenoside Rg5 docetaxel liposome

| / | Particle size (d · nm) | Intensity (%) | Width (d · nm) |
|---|---|---|---|
| Peak 1 | 176.2 | 100.0 | 67.84 |
| Peak 2 | 0.000 | 0.0 | 0.000 |
| Peak 3 | 0.000 | 0.0 | 0.000 |
| Average particle size (Z-Averaged.nm) | | 158.0 | |
| Polydispersity index (Pdl) | | 0.172 | |
| Intercept | | 0.946 | |
| Result quality | | good | |

Figure 10:
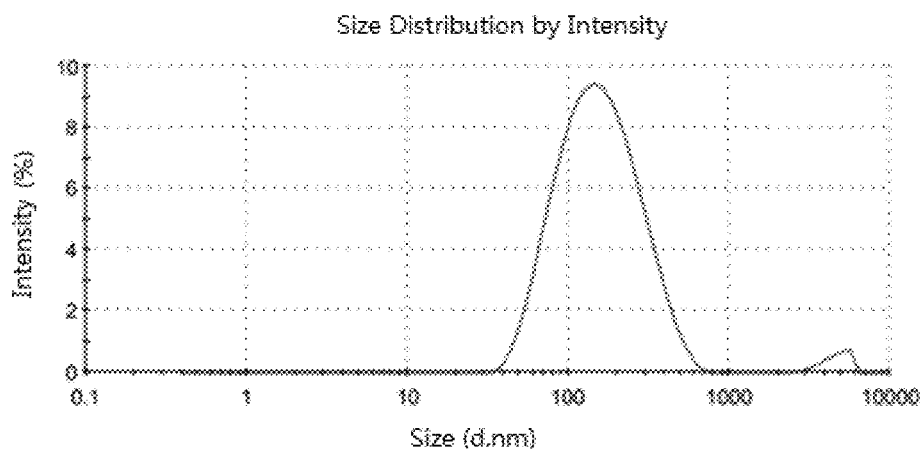
FIG. 10 is a particle size distribution figure of the ginsenoside Rg5 irinotecan hydrochloride liposome prepared by embodiment 10.

Embodiment 10 The Preparation of Ginsenoside Rg5 Irinotecan Hydrochloride Liposome Soybean lecithin 0.8 g, ginsenoside Rg5 0.6 g, irinotecan hydrochloride 0.2 g, soybean oil 0.4 g and vitamin C 0.5 g were added into 20 mL ethanol and stirred to form a clear solution at room temperature. The organic solvent was removed by a rotary evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 irinotecan hydrochloride liposome. Then the aqueous solution was split charging into vials and each vial contained 100 mg irinotecan hydrochloride. The aqueous solution was placed in a freeze-dryer to freeze dry for 72 hours, then protective gas (argon or nitrogen) was introduced, sealed to give the ginsenoside Rg5 irinotecan hydrochloride liposome. By test, the average particle size of the liposome was 121.6 nm (see Table 10 and FIG. 10).

TABLE 10

Particle size, distribution of particle size, intensity and width of the ginsenoside Rg5 irinotecan hydrochloride liposome

| / | Particle size (d · nm) | Intensity (%) | Width (d · nm) |
|---|---|---|---|
| Peak 1 | 175.4 | 97.6 | 102.0 |
| Peak 2 | 4611 | 2.4 | 824.5 |
| Peak 3 | 0.000 | 0.0 | 0.000 |
| Average particle size (Z-Averaged · nm) | | 121.6 | |
| Polydispersity index (Pdi) | | 0.319 | |
| Intercept | | 0.940 | |
| Result quality | | good | |

Embodiment 11 The Preparation of Ginsenoside Rg5 HCPT Liposome

Figure 11:
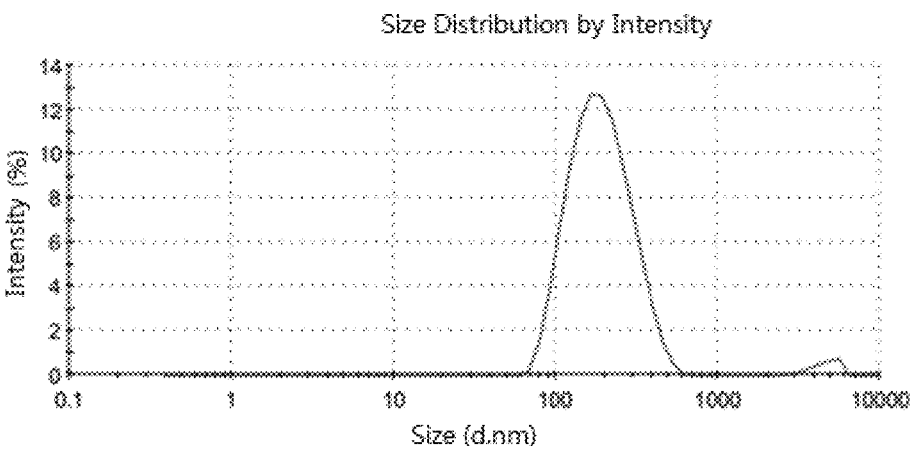
FIG. 11 is a particle size distribution figure of the ginsenoside Rg5 hydroxycamptothecine liposome prepared by embodiment 11.

Soybean lecithin 0.8 g, ginsenoside Rg5 0.6 g, HCPT 0.2 g, soybean oil 0.4 g and vitamin C 0.5 g were added into 20 mL ethanol and stirred to form a clear solution at room temperature. The organic solvent was removed by a rotary evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 HCPT liposome. Then the aqueous solution was split charging into vials and each vial contained 10 mg HCPT. The aqueous solution was placed in a freeze-dryer to freeze dry for 72 hours, then protective gas (argon or nitrogen) was introduced, sealed to give the ginsenoside Rg5 HCPT liposome. By test, the average particle size of the liposome was 177.9 nm (see Table 11 and FIG. 11).

TABLE 11

Particle size, distribution of particle size, intensity and width of the ginsenoside Rg5 HCPT liposome

| / | Particle size (d · nm) | Intensity (%) | Width (d · nm) |
|---|---|---|---|
| Peak 1 | 201.2 | 97.7 | 86.15 |
| Peak 2 | 4630 | 2.3 | 815.1 |
| Peak 3 | 0.000 | 0.0 | 0.000 |
| Average particle size (Z-Averaged · nm) | | 177.9 | |
| Polydispersity index (Pdi) | | 0.195 | |
| Intercept | | 0.966 | |
| Result quality | | good | |

Figure 12:
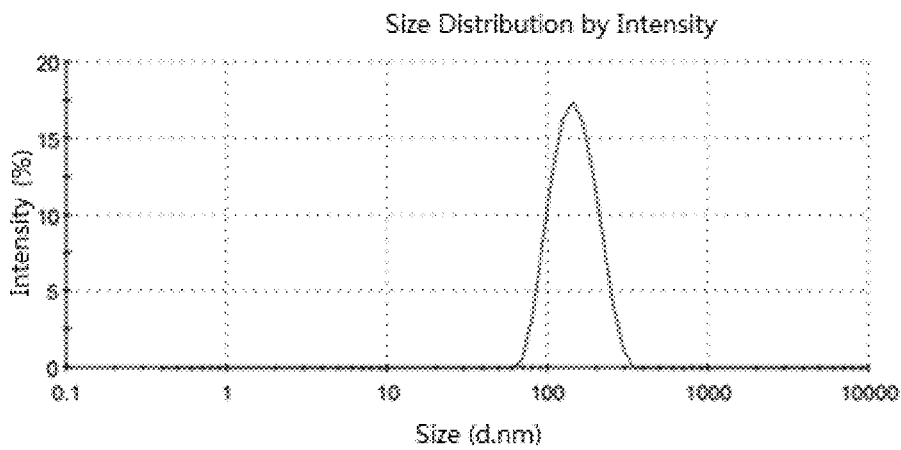
FIG. 12 is a particle size distribution figure of the ginsenoside Rg5 doxorubicin hydrochloride liposome prepared by embodiment 12.

Embodiment 12 The Preparation of Ginsenoside Rg5 Doxorubicin Hydrochloride Liposome Soybean lecithin 0.8 g, ginsenoside Rg5 0.6 g, doxorubicin hydrochloride 0.2 g, soybean oil 0.4 g and vitamin C 0.5 g were added into 20 mL ethanol and stirred to form a clear solution at room temperature. The organic solvent was removed by a rotary evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 doxorubicin hydrochloride liposome. Then the aqueous solution was split charging into vials and each vial contained 10 mg doxorubicin hydrochloride. The aqueous solution was placed in a freeze-dryer to freeze dry for 72 hours, then protective gas (argon or nitrogen) was introduced, sealed to give the ginsenoside Rg5 doxorubicin hydrochloride liposome. By test, the average particle size of the liposome was 144.5 nm (see Table 12 and FIG. 12).

TABLE 12

Particle size, distribution of particle size, intensity and width of the ginsenoside Rg5 doxorubicin hydrochloride liposome

| / | Particle size (d · nm) | Intensity (%) | Width (d · nm) |
|---|---|---|---|
| Peak 1 | 150.4 | 100.0 | 46.83 |
| Peak 2 | 0.000 | 0.0 | 0.000 |

TABLE 12-continued

Particle size, distribution of particle size, intensity and width of the ginsenoside Rg5 doxorubicin hydrochloride liposome

| / | Particle size (d · nm) | Intensity (%) | Width (d · nm) |
|---|---|---|---|
| Peak 3 | 0.000 | 0.0 | 0.000 |
| Average particle size (Z-Averaged · nm) | | 144.5 | |
| Polydispersity index (Pdi) | | 0.194 | |
| Intercept | | 0.970 | |
| Result quality | | good | |

Embodiment 13 The Preparation of Ginsenoside Rg5 Amphotericin B Liposome

Figure 13:
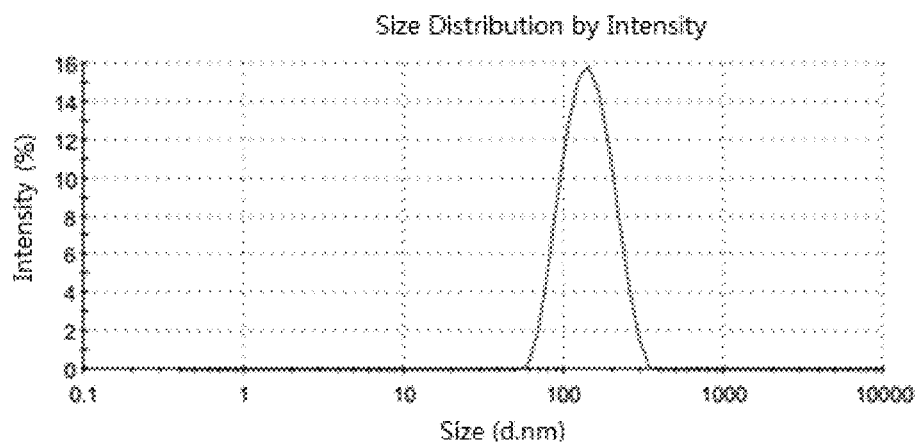
FIG. 13 is a particle size distribution figure of the ginsenoside Rg5 amphotericin B liposome prepared by embodiment 13.

Soybean lecithin 0.8 g, ginsenoside Rg5 0.6 g, amphotericin B 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 amphotericin B liposome. Then the aqueous solution was split charging into vials and each vial contained 10 mg amphotericin B. The aqueous solution was placed in a freeze-dryer to freeze dry for 72 hours, then protective gas (argon or nitrogen) was introduced, sealed to give the ginsenoside Rg5 amphotericin B liposome. By test, the average particle size of the liposome was 119.2 nm (see Table 13 and FIG. 13).

TABLE 13

Particle size, distribution of particle size, intensity and width of the ginsenoside Rg5 amphotericin B liposome

| / | Particle size (d · nm) | Intensity (%) | Width (d · nm) |
|---|---|---|---|
| Peak 1 | 147.4 | 100.0 | 50.35 |
| Peak 2 | 0.000 | 0.0 | 0.000 |
| Peak 3 | 0.000 | 0.0 | 0.000 |
| Average particle size (Z-Averaged · nm) | | 119.2 | |
| Polydispersity index (Pdi) | | 0.199 | |
| Intercept | | 0.947 | |
| Result quality | | good | |

Figure 14:
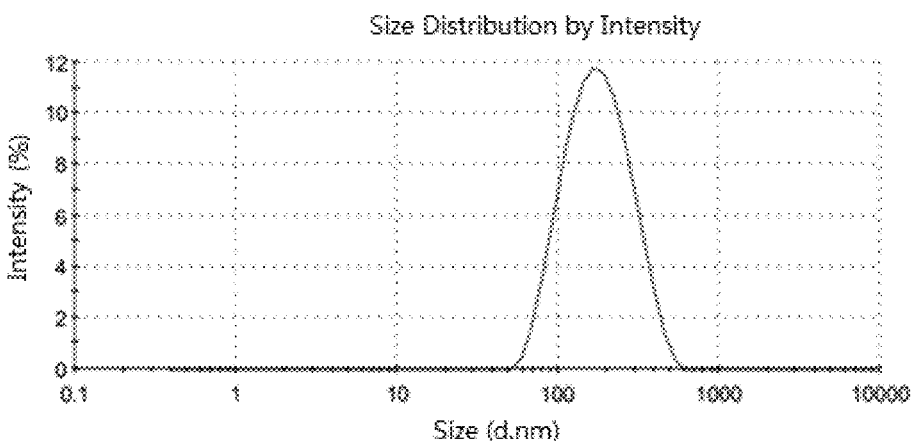
FIG. 14 is a particle size distribution figure of the ginsenoside Rg5 doxorubicin hydrochloride liposome prepared by embodiment 14.

Embodiment 14 The Preparation of Ginsenoside Rg5 Doxorubicin Hydrochloride Liposome Soybean lecithin 0.8 g, ginsenoside Rg5 0.6 g, doxorubicin hydrochloride 0.2 g, soybean oil 0.4 g and vitamin C 0.5 g were added into 20 mL ethanol and stirred to form a clear solution at room temperature. The organic solvent was removed by a rotary evaporation at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 doxorubicin hydrochloride liposome. Then the aqueous solution was split charging into vials and each vial contained 10 mg doxorubicin hydrochloride. The aqueous solution was placed in a freeze-dryer to freeze dry for 72 hours, then protective gas (argon or nitrogen) was introduced, sealed to give the ginsenoside Rg5 doxorubicin hydrochloride liposome. By test, the average particle size of the liposome was 158.2 nm (see Table 14 and FIG. 14).

TABLE 14

Particle size, distribution of particle size, intensity and width of the ginsenoside Rg5 doxorubicin hydrochloride liposome

| / | Particle size (d · nm) | Intensity (%) | Width (d · nm) |
|---|---|---|---|
| Peak 1 | 191.7 | 100.0 | 88.33 |
| Peak 2 | 0.000 | 0.0 | 0.000 |
| Peak 3 | 0.000 | 0.0 | 0.000 |
| Average particle size (Z-Averaged · nm) | | 158.2 | |
| Polydispersity index (Pdi) | | 0.159 | |
| Intercept | | 0.965 | |
| Result quality | | good | |

Figure 15:
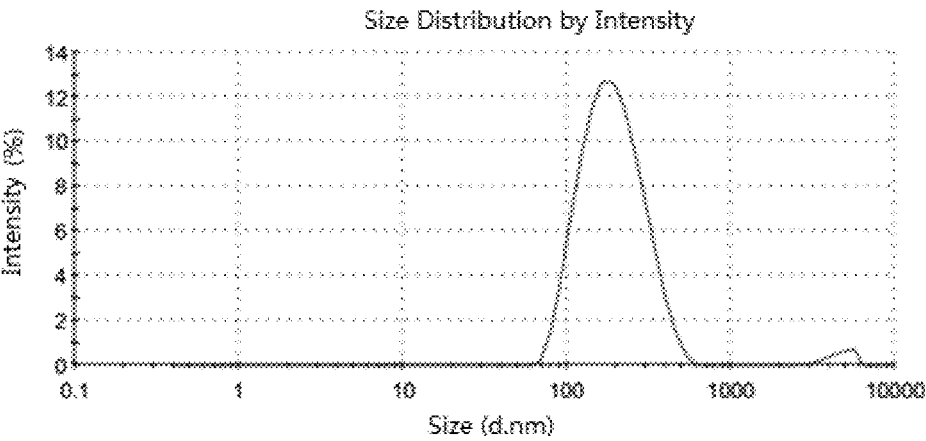
FIG. 15 is a particle size distribution figure of the ginsenoside Rg5 vincristine sulfate liposome prepared by embodiment 15.

Embodiment 15 The Preparation of Ginsenoside Rg5 Vincristine Sulfate Liposome Soybean lecithin 0.8 g, ginsenoside Rg5 0.6 g, vincristine sulfate 0.2 g, soybean oil 0.4 g and vitamin C 0.5 g were added into 20 mL ethanol and stirred to form a clear solution at room temperature. The organic solvent was removed by a rotary evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 vincristine sulfate liposome. Then the aqueous solution was split charging into vials and each vial contained 1 mg vincristine sulfate. The aqueous solution was placed in a freeze-dryer to freeze dry for 72 hours, then protective gas (argon or nitrogen) was introduced, sealed to give the ginsenoside Rg5 vincristine sulfate liposome. By test, the average particle size of the liposome was 177.9 nm (see Table 15 and FIG. 15).

TABLE 15

Particle size, distribution of particle size, intensity and width of the ginsenoside Rg5 vincristine sulfate liposome

| / | Particle size (d · nm) | Intensity (%) | Width (d · nm) |
|---|---|---|---|
| Peak 1 | 201.2 | 97.7 | 86.15 |
| Peak 2 | 4630 | 2.3 | 815.1 |
| Peak 3 | 0.000 | 0.0 | 0.000 |
| Average particle size (Z-Averaged · nm) | | 177.9 | |
| Polydispersity index (Pdi) | | 0.195 | |
| Intercept | | 0.966 | |
| Result quality | | good | |

Embodiment 16 The Preparation of Ginsenoside Rg5 Oxaliplatin Liposome

Figure 16:
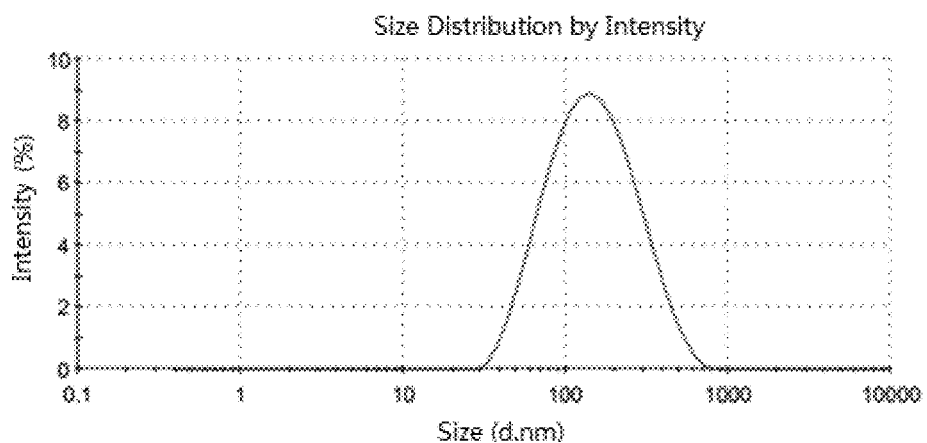
FIG. 16 is a particle size distribution figure of the ginsenoside Rg5 oxaliplatin liposome prepared by embodiment 16.

Soybean lecithin 0.8 g, ginsenoside Rg5 0.6 g, oxaliplatin 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 oxaliplatin liposome. Then the aqueous solution was split charging into vials and each vial contained 50 mg oxaliplatin. The aqueous solution was placed in a freeze-dryer to freeze dry for 72 hours, then protective gas (argon or nitrogen) was introduced, sealed to give the ginsenoside Rg5 oxaliplatin liposome. By test, the average particle size of the liposome was 122.7 nm (see Table 16 and FIG. 16).

TABLE 16

Particle size, distribution of particle size, intensity and width of the ginsenoside Rg5 oxaliplatin liposome

| / | Particle size (d · nm) | Intensity (%) | Width (d · nm) |
|---|---|---|---|
| Peak 1 | 171.3 | 100.0 | 108.6 |
| Peak 2 | 0.000 | 0.0 | 0.000 |
| Peak 3 | 0.000 | 0.0 | 0.000 |
| Average particle size (Z-Averaged · nm) | | 122.7 | |
| Polydispersity index (Pdi) | | 0.261 | |
| Intercept | | 0.923 | |
| Result quality | | good | |

Embodiment 17 The Preparation of Ginsenoside Rg5 Cisplatin Liposome

Figure 17:
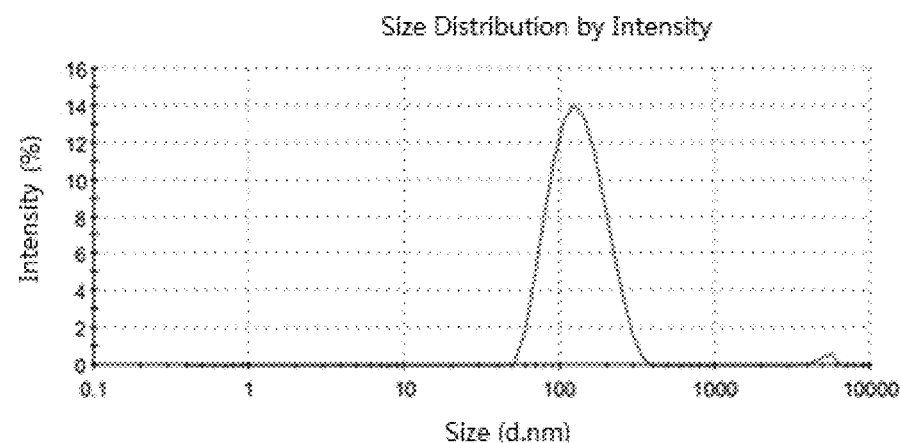
FIG. 17 is a particle size distribution figure of the ginsenoside Rg5 cisplatin liposome prepared by embodiment 17.

Soybean lecithin 0.8 g, ginsenoside Rg5 0.6 g, cisplatin 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 cisplatin liposome. Then the aqueous solution was split charging into vials and each vial contained 30 mg cisplatin. The aqueous solution was placed in a freeze-dryer to freeze dry for 72 hours, then protective gas (argon or nitrogen) was introduced, sealed to give the ginsenoside Rg5 cisplatin liposome. By test, the average particle size of the liposome was 124.3 nm (see Table 17 and FIG. 17).

TABLE 17

Particle size, distribution of particle size, intensity and width of the ginsenoside Rg5 cisplatin liposome

| / | Particle size (d · nm) | Intensity (%) | Width (d · nm) |
|---|---|---|---|
| Peak 1 | 137.8 | 98.7 | 53.70 |
| Peak 2 | 5042 | 1.3 | 585.3 |
| Peak 3 | 0.000 | 0.0 | 0.000 |
| Average particle size (Z-Averaged · nm) | | 124.3 | |
| Polydispersity index (Pdi) | | 0.175 | |
| Intercept | | 0.956 | |
| Result quality | | good | |

Embodiment 18 The Preparation of Ginsenoside Rg5 Fluorouracil Liposome

Figure 18:
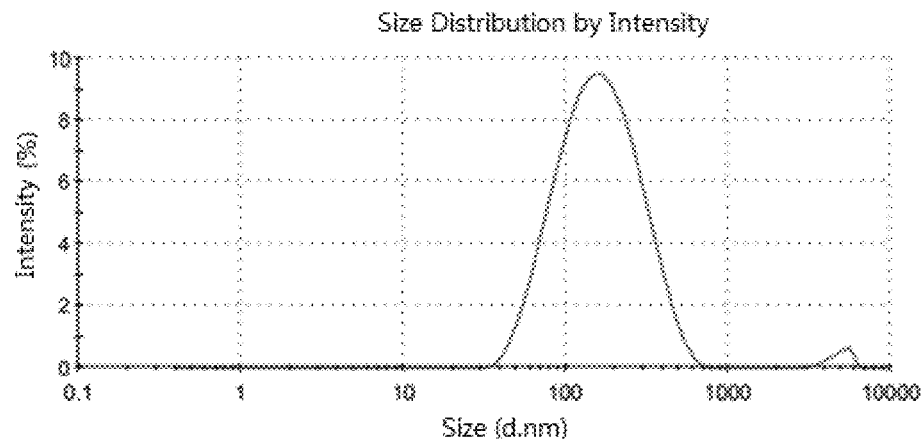
FIG. 18 is a particle size distribution figure of the ginsenoside Rg5 fluorouracil liposome prepared by embodiment 18.

Soybean lecithin 0.8 g, ginsenoside Rg5 0.6 g, fluorouracil 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 fluorouracil liposome. Then the aqueous solution was split charging into vials and each vial contained 250 mg fluorouracil. The aqueous solution was placed in a freeze-dryer to freeze dry for 72 hours, then protective gas (argon or nitrogen) was introduced, sealed to give the ginsenoside Rg5 fluorouracil liposome. By test, the average particle size of the liposome was 140.3 nm (see Table 18 and FIG. 18).

TABLE 18

Particle size, distribution of particle size, intensity and width of the ginsenoside Rg5 fluorouracil liposome

| / | Particle size (d · nm) | Intensity (%) | Width (d · nm) |
|---|---|---|---|
| Peak 1 | 182.1 | 98.3 | 103.6 |
| Peak 2 | 4846 | 1.7 | 703.6 |
| Peak 3 | 0.000 | 0.0 | 0.000 |
| Average particle size (Z-Averaged · nm) | | 140.3 | |
| Polydispersity index (Pdi) | | 0.261 | |
| Intercept | | 0.945 | |
| Result quality | | good | |

Figure 19:
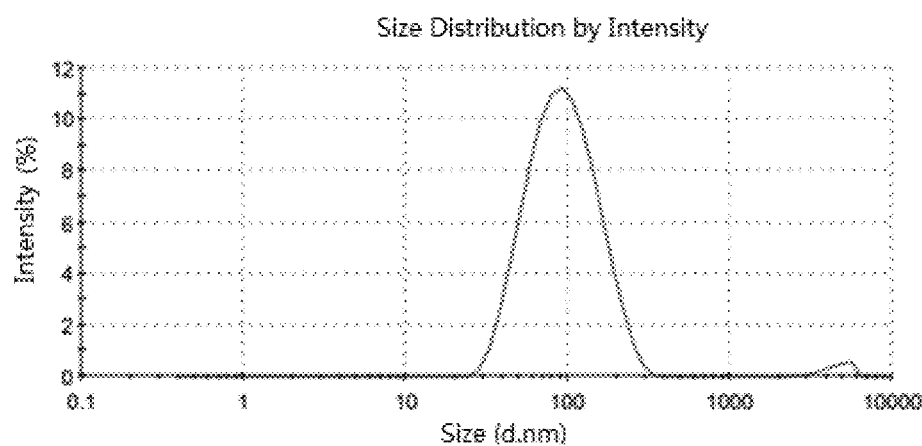
FIG. 19 is a particle size distribution figure of the ginsenoside Rg5 conventional SiRNA liposome prepared by embodiment 19.

Embodiment 19 The Preparation of Ginsenoside Rg5 Conventional SiRNA Liposome Soybean lecithin 0.8 g, ginsenoside Rg5 0.6 g, conventional SiRNA 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 conventional SiRNA liposome. Then the aqueous solution was split charging into vials and each vial contained 20 mg conventional SiRNA. The aqueous solution was placed in a freeze-dryer to freeze dry for 72 hours, then protective gas (argon or nitrogen) was introduced, sealed to give the ginsenoside Rg5 conventional SiRNA liposome. By test, the average particle size of the liposome was 84.58 nm (see Table 19 and FIG. 19).

TABLE 19

Particle size, distribution of particle size, intensity and width of the ginsenoside Rg5 conventional SiRNA liposome

| / | Particle size (d · nm) | Intensity (%) | Width (d · nm) |
|---|---|---|---|
| Peak 1 | 101.7 | 98.1 | 49.29 |
| Peak 2 | 4577 | 1.9 | 836.5 |
| Peak 3 | 0.000 | 0.0 | 0.000 |
| Average particle size (Z-Averaged · nm) | | 84.58 | |
| Polydispersity index (Pdi) | | 0.219 | |
| Intercept | | 0.932 | |
| Result quality | | good | |

Embodiment 20 Ginsenoside Rg5 Cabazitaxel Liposome

Soybean lecithin 0.8 g, ginsenoside Rg5 0.6 g, cabazitaxel 0.2 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 cabazitaxel liposome. Then the aqueous solution was split charging into vials and each vial contained 250 mg cabazitaxel. The aqueous solution was placed in a freeze-dryer to freeze dry for 72 hours, then protective gas (argon or nitrogen) was introduced, sealed to give the ginsenoside Rg5 cabazitaxel liposome.

Figure 20:
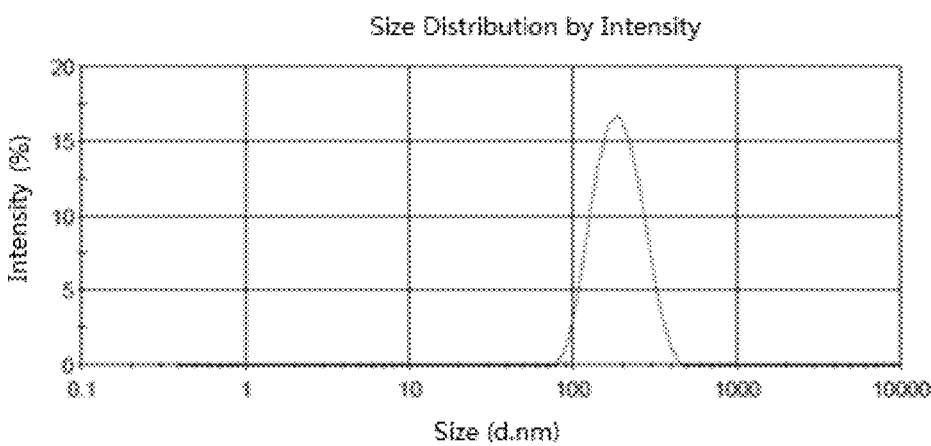
FIG. 20 is a particle size distribution figure of the ginsenoside Rg5 doxorubicin hydrochloride liposome prepared by embodiment 21.

Embodiment 21 The Preparation of Ginsenoside Rg5 Doxorubicin Hydrochloride Liposome Soybean lecithin 0.8 g, ginsenoside Rg5 0.6 g and vitamin C 0.5 g were added into 20 mL ethanol and stirred to form a clear solution at room temperature. The organic solvent was removed by a rotatory evaporator at 35 to 40° C. to form a film, and 20 mL 6.6% ammonium sulfate aqueous solution (the percentage refers to the mass of the ammonium sulfate relative to the total mass of the ammonium sulfate aqueous solution) was added. An operation of ultrasound was carried out until the particle size of the blank liposome was between 0.1 and 0.3 micron, thereby obtaining a solution of the blank liposome. The solution of the blank liposome was dialyzed for 12 hours in a 0.15M (0.15 mol/L) glucose solution, then a corresponding mass of trehalose was added according to a volume of the dialyzed blank liposome solution to make a mass fraction of the trehalose in the blank liposome solution reach 10%, the percentage refers to the mass of the trehalose relative to the total mass of the blank liposome solution. 1 mL doxorubicin hydrochloride aqueous solution with a mass fraction of 20% (doxorubicin hydrochloride 0.2 g) was added, and kept for 30 minutes in a water bath at 37° C. A 0.22 micron microporous membrane was used to filtration thereby obtaining an aqueous solution containing ginsenoside Rg5 doxorubicin hydrochloride liposome. Then the aqueous solution was split charging into vials and each vial contained 10 mg doxorubicin hydrochloride. The aqueous solution was placed in a freeze-dryer to freeze dry for 72 hours, then protective gas (argon or nitrogen) was introduced, sealed to give the ginsenoside Rg5 doxorubicin hydrochloride liposome. By test, the average particle size of the liposome was 180.8 nm (see Table 20 and FIG. 20).

TABLE 20

Particle size, distribution of particle size, intensity and width of the ginsenoside Rg5 doxorubicin hydrochloride liposome

| / | Particle size (d · nm) | Intensity (%) | Width (d · nm) |
|---|---|---|---|
| Peak 1 | 195.4 | 100.0 | 63.16 |
| Peak 2 | 0.000 | 0.0 | 0.000 |
| Peak 3 | 0.000 | 0.0 | 0.000 |
| Average particle size (Z-Averaged · nm) | | 180.8 | |
| Polydispersity index (Pdi) | | 0.180 | |
| Intercept | | 0.879 | |
| Result quality | | good | |

Embodiment 22 The Preparation of Ginsenoside Rg5 Amphotericin B Liposome

Figure 21:
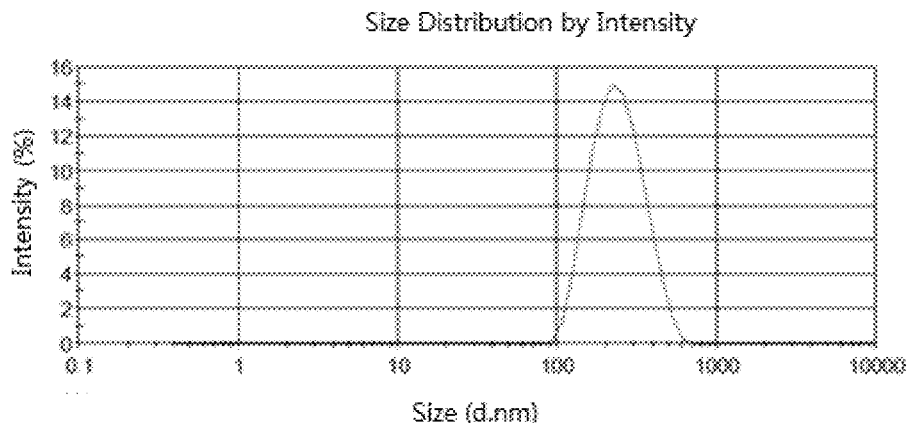
FIG. 21 is a particle size distribution figure of the ginsenoside Rg5 amphotericin B liposome prepared by embodiment 22.

Soybean lecithin 0.8 g, ginsenoside Rg5 0.6 g and vitamin C 0.5 g were added into 20 mL ethanol and stirred to form a clear solution at room temperature. The organic solvent was removed by a rotatory evaporator at 35 to 40° C. to form a film, and 1 mL amphotericin B in DMSO solution with a mass fraction of 20% (the mass of amphotericin B was 0.22 g) and 20 mL trehalose aqueous solution with a mass fraction of 10% (trehalose 2 g) were added. An operation of ultrasound was carried out until the particle size of the liposome was between 0.1 and 0.3 micron, thereby obtaining a solution of the liposome loaded with an active substance. The solution of the liposome loaded with the active substance was poured into a dialysis bag and was dialyzed in pure water whose volume is 100 times that of the solution for 12 hours at room temperature. A 0.22 micron microporous membrane was used to filtration thereby obtaining an aqueous solution containing ginsenoside Rg5 amphotericin B liposome. Then the aqueous solution was split charging into vials and each vial contained 10 mg amphotericin B. The aqueous solution was placed in a freeze-dryer to freeze dry for 72 hours, then protective gas (argon or nitrogen) was introduced, sealed to give the ginsenoside Rg5 amphotericin B liposome. By test, the average particle size of the liposome was 216.4 nm (see Table 21 and FIG. 21).

TABLE 21

Particle size, distribution of particle size, intensity and width of the ginsenoside Rg5 amphotericin B liposome

| / | Particle size (d · nm) | Intensity (%) | Width (d · nm) |
|---|---|---|---|
| Peak 1 | 249.6 | 100.0 | 92.14 |
| Peak 2 | 0.000 | 0.0 | 0.000 |
| Peak 3 | 0.000 | 0.0 | 0.000 |
| Average particle size (Z-Averaged · nm) | | 216.4 | |
| Polydispersity index (Pdi) | | 0.165 | |

TABLE 21-continued

Particle size, distribution of particle size, intensity and width of the ginsenoside Rg5 amphotericin B liposome

| / | Particle size (d · nm) | Intensity (%) | Width (d · nm) |
|---|---|---|---|
| Intercept | | 0.951 | |
| Result quality | | good | |

Embodiment 23 The Preparation of Ginsenoside Rg5 Epirubicin Liposome

Figure 22:
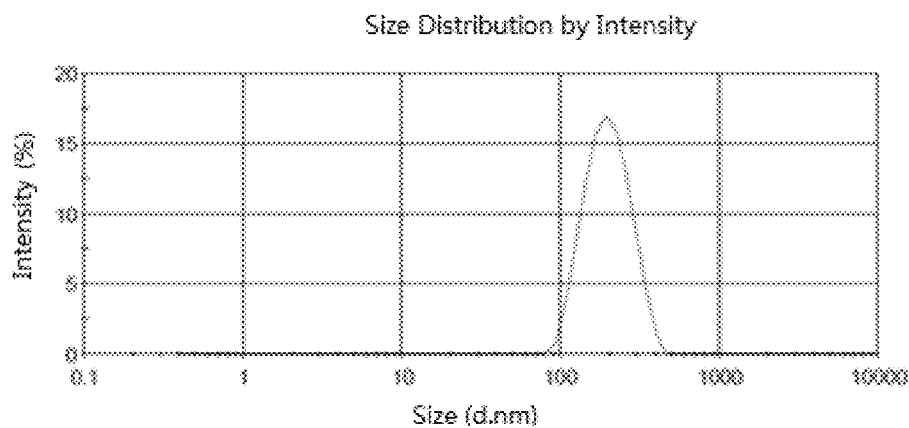
FIG. 22 is a particle size distribution figure of the ginsenoside Rg5 epirubicin hydrochloride liposome prepared by embodiment 23.

Soybean lecithin 0.8 g, ginsenoside Rg5 0.6 g and vitamin C 0.5 g were added into 20 mL ethanol and stirred to form a clear solution at room temperature. The organic solvent was removed by a rotatory evaporator at 35 to 40° C. to form a film, and 20 mL ammonium sulfate aqueous solution with a mass fraction of 6.6% was added. An operation of ultrasound was carried out until the particle size of the blank liposome was between 0.1 and 0.3 micron, thereby obtaining a solution of the blank liposome. The blank liposome solution was dialyzed for 12 hours in a 0.15M glucose solution, then a corresponding mass of trehalose was added according to a volume of the dialyzed blank liposome solution to make a mass fraction of the trehalose in the blank liposome solution reach 10%, the percentage refers to the mass of the trehalose relative to the total mass of the blank liposome solution. 1 mL epirubicin aqueous solution with a mass fraction of 20% (epirubicin 0.2 g) was added, and kept for 30 minutes in a water bath at 37° C. A 0.22 micron microporous membrane was used to filtration thereby obtaining an aqueous solution containing ginsenoside Rg5 epirubicin liposome. Then the aqueous solution was split charging into vials and each vial contained 10 mg epirubicin. The aqueous solution was placed in a freeze-dryer to freeze dry for 72 hours, then protective gas (argon or nitrogen) was introduced, sealed to give the ginsenoside Rg5 epirubicin liposome. By test, the average particle size of the liposome was 187.6 nm (see Table 22 and FIG. 22).

TABLE 22

Particle size, distribution of particle size, intensity and width of the ginsenoside Rg5 epirubicin liposome

| / | Particle size (d · nm) | Intensity (%) | Width (d · nm) |
|---|---|---|---|
| Peak 1 | 203.7 | 100.0 | 64.72 |
| Peak 2 | 0.000 | 0.0 | 0.000 |
| Peak 3 | 0.000 | 0.0 | 0.000 |
| Average particle size (Z-Averaged · nm) | | 187.6 | |
| Polydispersity index (Pdi) | | 0.142 | |
| Intercept | | 0.922 | |
| Result quality | | good | |

Figure 23:
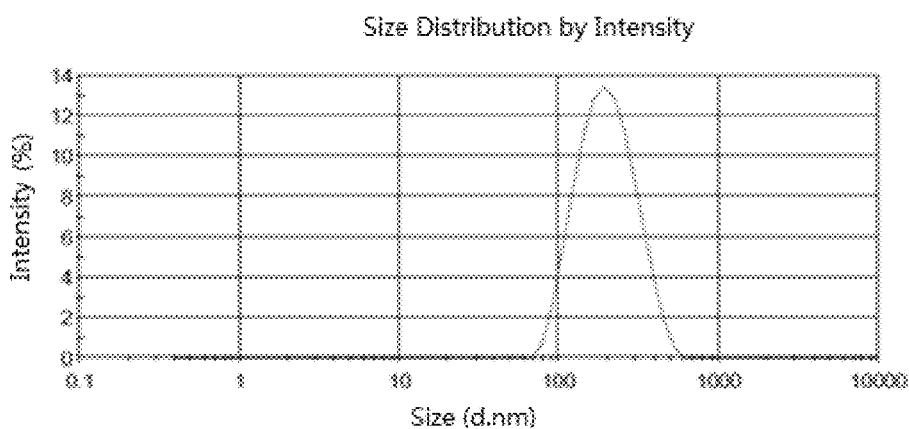
FIG. 23 is a particle size distribution figure of the ginsenoside Rg5 vincristine sulfate liposome prepared by embodiment 24.

Embodiment 23 The Preparation of Ginsenoside Rg5 Vincristine Sulfate Liposome Soybean lecithin 0.8 g, ginsenoside Rg5 0.6 g and vitamin C 0.5 g were added into 20 mL ethanol and stirred to form a clear solution at room temperature. The organic solvent was removed by a rotary evaporator at 60 to 70° C. to form a film, and 20 mL a mixed aqueous solution of trehalose with a mass fraction of 10% and citric acid with a mass fraction of 5.76% was added. An operation of ultrasound was carried out until the particle size of the blank liposome was between 0.1 and 0.3 micron, thereby obtaining a solution of the blank liposome. 1 mL vincristine sulfate aqueous solution with a mass fraction of 20% (vincristine sulfate 0.2 g) and 6 mL disodium hydrogen phosphate aqueous solution with a mass fraction of 7.1% were added, pure water was added to adjust pH of the external aqueous layer reaching 7.30, kept for 30 minutes in a water bath at 60° C. A 0.22 micron microporous membrane was used to filtration thereby obtaining an aqueous solution containing ginsenoside Rg5 vincristine sulfate liposome. Then the aqueous solution was split charging into vials and each vial contained 1 mg vincristine sulfate. The aqueous solution was placed in a freeze-dryer to freeze dry for 72 hours, then protective gas (argon or nitrogen) was introduced, sealed to give the ginsenoside Rg5 vincristine sulfate liposome. By test, the average particle size of the liposome was 188.3 nm (see Table 23 and FIG. 23).

TABLE 23

Particle size, distribution of particle size, intensity and width of the ginsenoside Rg5 vincristine sulfate liposome

| / | Particle size (d · nm) | Intensity (%) | Width (d · nm) |
|---|---|---|---|
| Peak 1 | 211.7 | 100.0 | 86.37 |
| Peak 2 | 0.000 | 0.0 | 0.000 |
| Peak 3 | 0.000 | 0.0 | 0.000 |
| Average particle size (Z-Averaged · nm) | | 188.3 | |
| Polydispersity index (Pdi) | | 0.199 | |
| Intercept | | 0.919 | |
| Result quality | | good | |

Embodiment 25 The Preparation of Ginsenoside Rg5 Oxaliplatin Liposome

Figure 24:
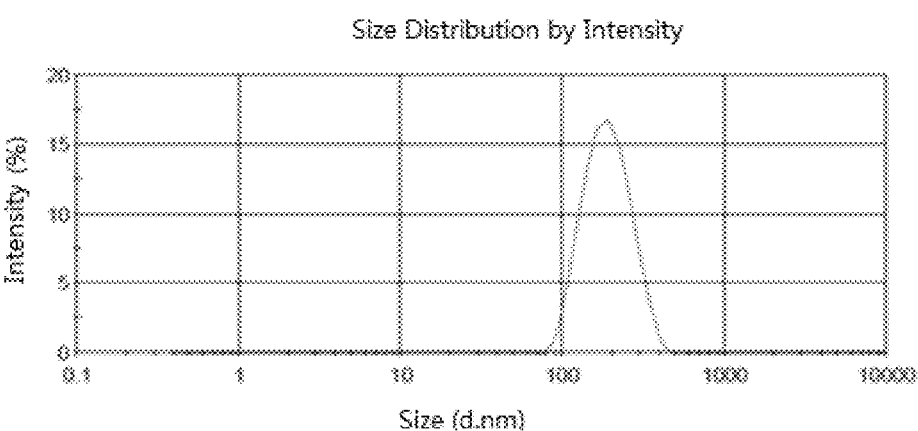
FIG. 24 is a particle size distribution figure of the ginsenoside Rg5 oxaliplatin liposome prepared by embodiment 25.

Soybean lecithin 0.8 g, ginsenoside Rg5 0.6 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL mixed aqueous solution of oxaliplatin with a mass fraction of 1% and trehalose with a mass fraction of 10% (oxaliplatin 0.2 g, trehalose 2 g) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 oxaliplatin liposome. Then the aqueous solution was split charging into vials and each vial contained 50 mg oxaliplatin. The aqueous solution was placed in a freeze-dryer to freeze dry for 72 hours, then protective gas (argon or nitrogen) was introduced, sealed to give the ginsenoside Rg5 oxaliplatin liposome. By test, the average particle size of the liposome was 180.8 nm (see Table 24 and FIG. 24).

TABLE 24

Particle size, distribution of particle size, intensity and width of the ginsenoside Rg5 oxaliplatin liposome

| / | Particle size (d · nm) | Intensity (%) | Width (d · nm) |
|---|---|---|---|
| Peak 1 | 195.4 | 100.0 | 63.16 |
| Peak 2 | 0.000 | 0.0 | 0.000 |
| Peak 3 | 0.000 | 0.0 | 0.000 |

TABLE 24-continued

Particle size, distribution of particle size, intensity and width of the ginsenoside Rg5 oxaliplatin liposome

| / | Particle size (d · nm) | Intensity (%) | Width (d · nm) |
|---|---|---|---|
| Average particle size (Z-Averaged · nm) | | 180.8 | |
| Polydispersity index (Pdi) | | 0.180 | |
| Intercept | | 0.879 | |
| Result quality | | good | |

Embodiment 26 The Preparation of Ginsenoside Rg5 Cisplatin Liposome

Figure 25:
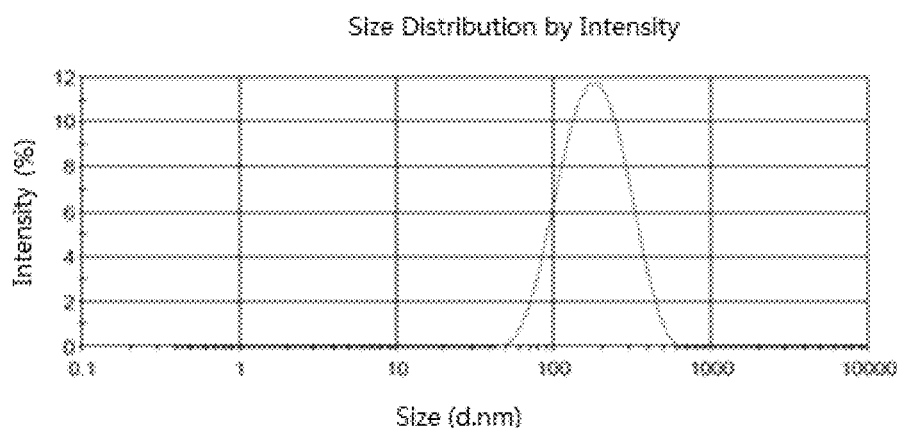
FIG. 25 is a particle size distribution figure of the ginsenoside Rg5 cisplatin liposome prepared by embodiment 26.

Soybean lecithin 0.8 g, ginsenoside Rg5 0.6 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL mixed aqueous solution of cisplatin with a mass fraction of 1% and trehalose with a mass fraction of 10% (cisplatin 0.2 g, trehalose 2 g) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 cisplatin liposome. Then the aqueous solution was split charging into vials and each vial contained 30 mg cisplatin. The aqueous solution was placed in a freeze-dryer to freeze dry for 72 hours, then protective gas (argon or nitrogen) was introduced, sealed to give the ginsenoside Rg5 cisplatin liposome. By test, the average particle size of the liposome was 143.6 nm (see Table 25 and FIG. 25).

TABLE 25

Particle size, distribution of particle size, intensity and width of the ginsenoside Rg5 cisplatin liposome

| / | Particle size (d · nm) | Intensity (%) | Width (d · nm) |
|---|---|---|---|
| Peak 1 | 195.6 | 100 | 89.8 |
| Peak 2 | 0.000 | 0.0 | 0.000 |
| Peak 3 | 0.000 | 0.0 | 0.000 |
| Average particle size (Z-Averaged · nm) | | 143.6 | |
| Polydispersity index (PdI) | | 0.266 | |
| Intercept | | −0.937 | |
| Result quality | | good | |

Embodiment 27 The Preparation of Ginsenoside Rg5 Fluorouracil Liposome

Figure 26:
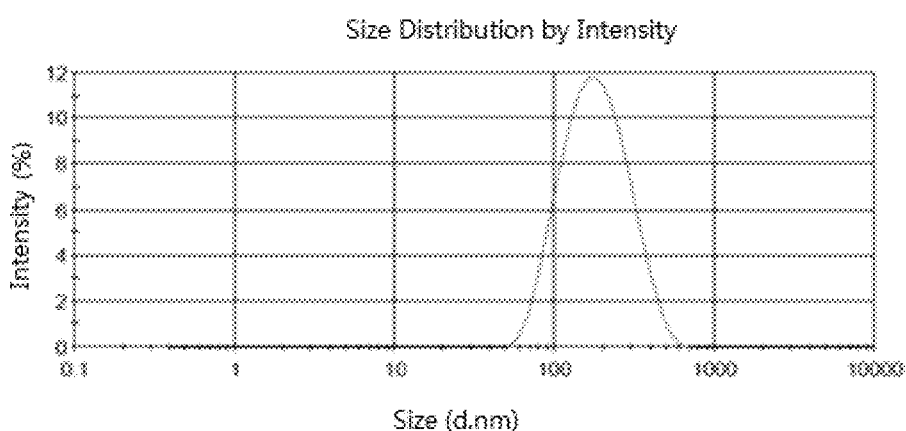
FIG. 26 is a particle size distribution figure of the ginsenoside Rg5 fluorouracil liposome prepared by embodiment 27.

Soybean lecithin 0.8 g, ginsenoside Rg5 0.6 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL mixed aqueous solution of fluorouracil with a mass fraction of 1% and trehalose with a mass fraction of 10% (fluorouracil 0.2 g, trehalose 2 g) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 fluorouracil liposome. Then the aqueous solution was split charging into vials and each vial contained 250 mg fluorouracil. The aqueous solution was placed in a freeze-dryer to freeze dry for 72 hours, then protective gas (argon or nitrogen) was introduced, sealed to give the ginsenoside Rg5 fluorouracil liposome. By test, the average particle size of the liposome was 145.6 nm (see Table 26 and FIG. 26).

TABLE 26

Particle size, distribution of particle size, intensity and width of the ginsenoside Rg5 fluorouracil liposome

| / | Particle size (d · nm) | Intensity (%) | Width (d · nm) |
|---|---|---|---|
| Peak 1 | 195.5 | 100 | 90.68 |
| Peak 2 | 0.000 | 0.0 | 0.000 |
| Peak 3 | 0.000 | 0.0 | 0.000 |
| Average particle size (Z-Averaged · nm) | | 145.6 | |
| Polydispersity index (PdI) | | 0.258 | |
| Intercept | | 0.934 | |
| Result quality | | good | |

Figure 27:
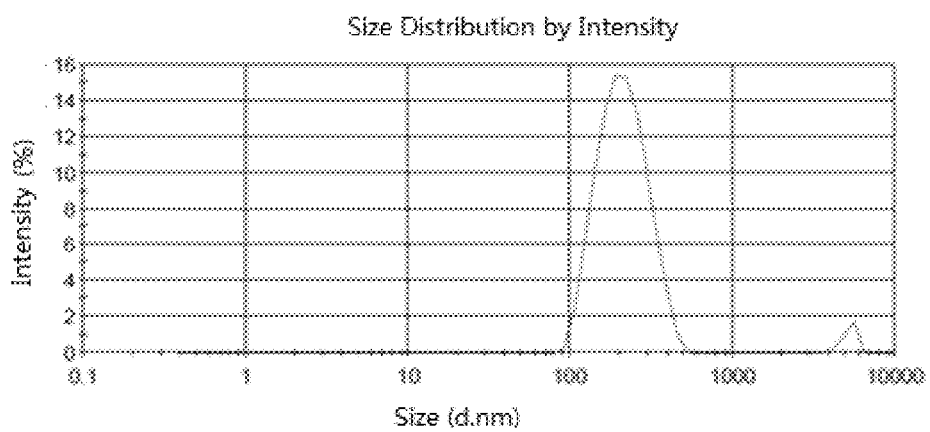
FIG. 27 is a particle size distribution figure of the ginsenoside Rg5 conventional SiRNA liposome prepared by embodiment 28.

Embodiment 28 The Preparation of Ginsenoside Rg5 Conventional SiRNA Liposome DOTAP 0.5 g, Soybean lecithin 0.3 g, ginsenoside Rg5 0.6 g, soybean oil 0.4 g and vitamin C 0.5 g were added into 20 mL ethanol and stirred to form a clear solution at room temperature. The organic solvent was removed by a rotatory evaporator at 60 to 70° C. to form a film, and 20 mL mixed aqueous solution of conventional SiRNA with a mass fraction of 1% and trehalose with a mass fraction of 10% (SiRNA 0.2 g, trehalose 2 g) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 conventional SiRNA liposome. Then the aqueous solution was split charging into vials and each vial contained 20 mg conventional SiRNA. The aqueous solution was placed in a freeze-dryer to freeze dry for 72 hours, then protective gas (argon or nitrogen) was introduced, sealed to give the ginsenoside Rg5 conventional SiRNA liposome. By test, the average particle size of the liposome was 215.0 nm (see Table 27 and FIG. 27).

TABLE 27

Particle size, distribution of particle size, intensity and width of the ginsenoside Rg5 conventional SiRNA liposome

| / | Particle size (d · nm) | Intensity (%) | Width (d · nm) |
|---|---|---|---|
| Peak 1 | 219.3 | 97.1 | 74.35 |
| Peak 2 | 5181 | 2.9 | 485.0 |
| Peak 3 | 0.000 | 0.0 | 0.000 |
| Average particle size (Z-Averaged · nm) | | 215.0 | |
| Polydispersity index (PdI) | | 0.237 | |
| Intercept | | 0.946 | |
| Result quality | | good | |

Embodiment 29 The Preparation of Ginsenoside Rg5 Paclitaxel Liposome

Egg lecithin 8 g, ginsenoside Rg5 6 g, paclitaxel 1.5 g, soybean oil 4 g and vitamin C 0.5 g were added into 200 mL chloroform and stirred to form a clear solution at room temperature. The organic solvent was removed by a film evaporator at 35 to 45° C. to form a film, and 200 mL 10% trehalose aqueous solution (the percentage refers to the mass of the trehalose relative to the total mass of the trehalose aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome.

Embodiment 30 The Preparation of Ginsenoside Rg5 Paclitaxel Liposome

Egg lecithin 14 g, ginsenoside Rg5 12 g, paclitaxel 4 g, soybean oil 8 g, cholesterol 0.5 g and vitamin E 0.5 g were added into 400 mL chloroform and stirred to form a clear solution at room temperature. The organic solvent was removed by a rotatory evaporator at 35 to 45° C. to form a film, and 400 mL 5% saccharose aqueous solution (the percentage refers to the mass of the saccharose relative to the total mass of the saccharose aqueous solution) was added. An operation of homogenization by a high pressure homogenizer was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials and each vial contained 30 mg paclitaxel. The aqueous solution was placed in a freeze-dryer to freeze dry for 72 hours, then protective gas (argon or nitrogen) was introduced, sealed to give the ginsenoside Rg5 paclitaxel liposome.

Embodiment 31 The Preparation of Ginsenoside Rg5 Docetaxel Liposome

Egg lecithin 8 g, ginsenoside Rg5 6 g, docetaxel 3 g, soybean oil 4 g and vitamin C 0.5 g were added into 200 mL chloroform and stirred to form a clear solution at room temperature. The organic solvent was removed by a membrane evaporator at 35 to 45° C. to form a film, and 200 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 docetaxel liposome. Then the aqueous solution was split charging into vials and each vial contained 20 mg docetaxel. The aqueous solution was placed in a freeze-dryer to freeze dry for 72 hours, then protective gas (argon or nitrogen) was introduced, sealed to give the ginsenoside Rg5 docetaxel liposome.

Embodiment 32 The Preparation of Ginsenoside Rg5 Irinotecan Hydrochloride Liposome Egg lecithin 8 g, ginsenoside Rg5 6 g, irinotecan hydrochloride 2 g and soybean oil 4 g were added into 200 mL chloroform and stirred to form a clear solution at room temperature. The organic solvent was removed by a rotatory evaporator at 35 to 45° C. to form a film, and 200 mL 10% trehalose aqueous solution (the percentage refers to the mass of the trehalose relative to the total mass of the trehalose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 irinotecan hydrochloride liposome. Then the aqueous solution was split charging into vials and each vial contained 100 mg irinotecan hydrochloride. The aqueous solution was placed in a freeze-dryer to freeze dry for 72 hours, then protective gas (argon or nitrogen) was introduced, sealed to give the ginsenoside Rg5 irinotecan hydrochloride liposome.

Application Embodiments

In the following application embodiments, C(μM) means concentration, wherein a concentration of Taxol+Rg5 refers to the concentration of paclitaxel and ginsenoside Rg5 in the ginsenoside Rg5 paclitaxel liposome, for example, 5+30 means that in the ginsenoside Rg5 paclitaxel liposome, the concentration of the paclitaxel is 5 1M and the concentration of the ginsenoside Rg5 is 30 μM. Time (d) means time (day).

In the following application embodiments, unless otherwise specified, the ginsenoside Rg5 blank liposome refers to the ginsenoside Rg5 blank liposome (abbreviated as Rg5 blank) prepared according to embodiment 1; unless otherwise specified, the ginsenoside Rg5 paclitaxel liposome refers to the ginsenoside Rg5 paclitaxel liposome prepared according to embodiment 4 (abbreviated as Taxol+Rg5); the conventional paclitaxel injection (Taxol) is commercially available (abbreviated as Taxol).

Application Embodiment 1: Cell Experiment In Vitro and Animal Experiment In Vivo for Ginsenosides Rg5 Paclitaxel Liposome Against Human Lung Cancer Cell Line (A549)/Paclitaxel-Resistant Human Lung Cancer Cell Line (A549/T)

1. Cell Experiment In Vitro

Figure 28:
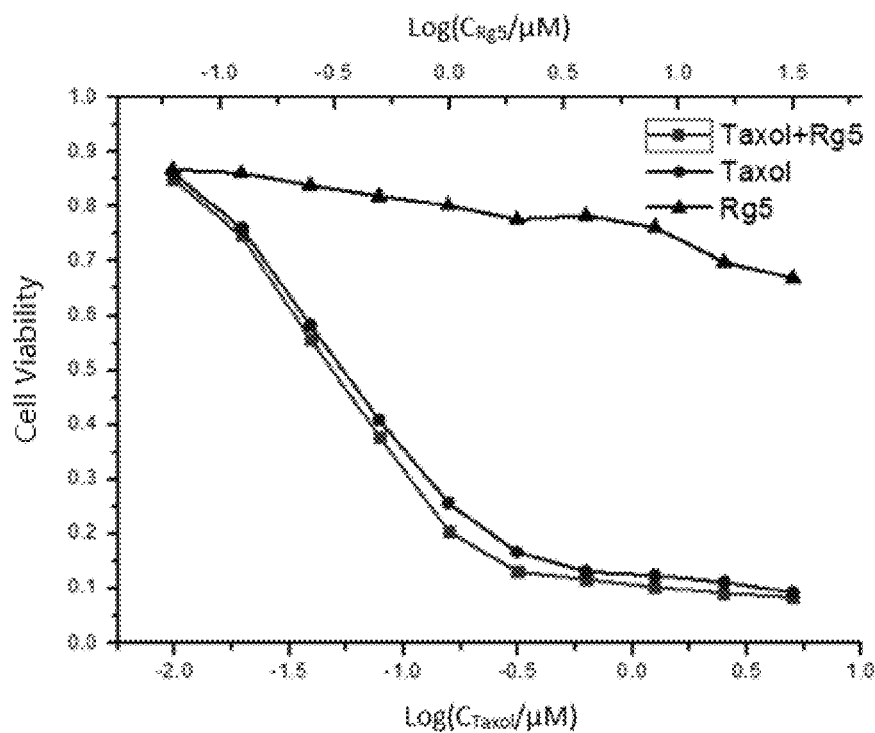
FIG. 28 is a cell survival rate graph of Taxol, blank Rg5 and Taxol+Rg5 against human lung cancer cell line (A549).
Figure 29:
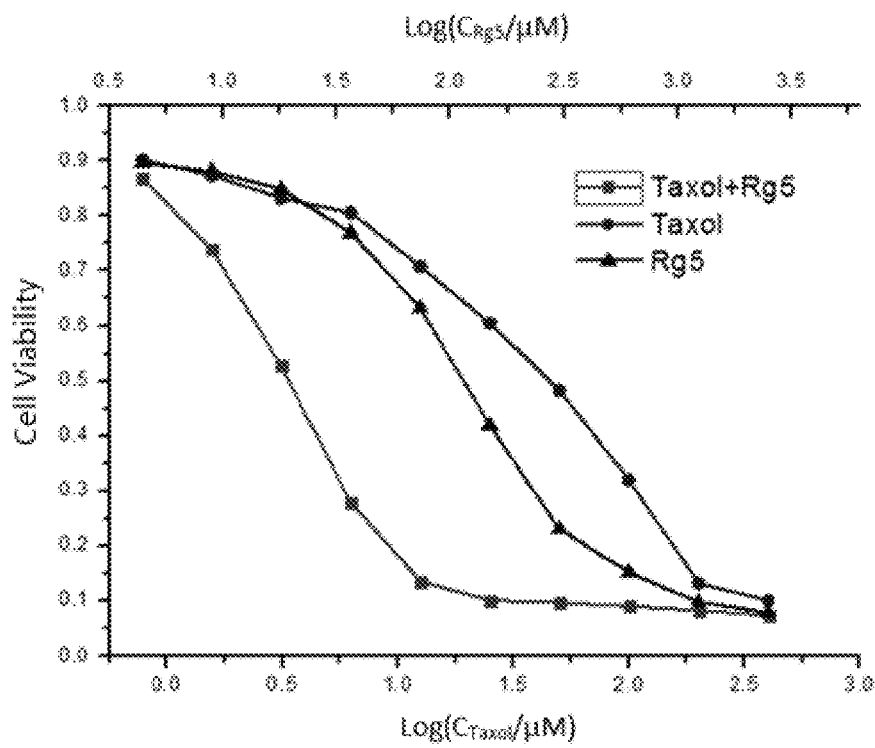
FIG. 29 is a cell survival rate graph of Taxol, blank Rg5 and Taxol+Rg5 against paclitaxel-resistant human lung cancer cell line (A549/T).

According to the assay of cell experiment in vitro, cell survival rates of human lung cancer cell line (A549) or paclitaxel-resistant human lung cancer cell line (A549/T) were determined respectively regarding conventional paclitaxel injection (Taxol), ginsenoside Rg5 blank liposome (blank Rg5) and ginsenoside Rg5 paclitaxel liposome (Taxol+Rg5). 10 Different drug concentrations were set as shown in Table 28 and Table 29. The specific experimental data are shown in Table 28, 29 and FIG. 28, 29. FIG. 28 is the cell survival rate graph of Taxol, blank Rg5 and Taxol+Rg5 against human lung cancer cell line (A549); FIG. 29 is the cell survival rate graph of Taxol, blank Rg5 and Taxol+Rg5 against paclitaxel-resistant human lung cancer cell line (A549/T).

TABLE 28

Cell survival rates of Taxol, blank Rg5 and Taxol + Rg5 against human lung cancer cell line (A 549)

| C (μM) | | | Cell Viability | | |
|---|---|---|---|---|---|
| Taxol + Rg5 | Taxol | Blank Rg5 | Taxol + Rg5 | Taxol | Blank Rg5 |
| 5 + 30 | 5 | 30 | 0.084 | 0.093 | 0.669 |
| 2.5 + 15 | 2.5 | 15 | 0.092 | 0.112 | 0.698 |
| 1.25 + 7.5 | 1.25 | 7.5 | 0.103 | 0.124 | 0.762 |
| 0.625 + 3.75 | 0.625 | 3.75 | 0.117 | 0.131 | 0.783 |
| 0.3125 + 1.875 | 0.3125 | 1.875 | 0.131 | 0.167 | 0.776 |
| 0.15625 + 0.9375 | 0.15625 | 0.9375 | 0.206 | 0.257 | 0.802 |
| 0.078125 + 0.46875 | 0.078125 | 0.46875 | 0.379 | 0.409 | 0.819 |
| 0.039063 + 0.23437 | 0.039063 | 0.234375 | 0.557 | 0.583 | 0.839 |
| 0.019531 + 0.117188 | 0.019531 | 0.117188 | 0.747 | 0.761 | 0.861 |
| 0.009766 + 0.058594 | 0.009766 | 0.058594 | 0.851 | 0.862 | 0.867 |

Table 28 and FIG. 28 show that activity of ginsenoside Rg5 blank liposome was relatively weak against human lung cancer cell line (A549), and the activity of Taxol+Rg5 was slightly improved relative to conventional paclitaxel injection.

TABLE 29

Cell survival rates of Taxol, blank Rg5 and Taxol + Rg5 against paclitaxel-resistant human lung cancer cell line (A549/T)

| C (μM) | | | Cell Viability | | |
|---|---|---|---|---|---|
| Taxol + Rg5 | Taxol | Blank Rg5 | Taxol + Rg5 | Taxol | Blank Rg5 |
| 400 + 2400 | 400 | 2400 | 0.074 | 0.101 | 0.079 |
| 200 + 1200 | 200 | 1200 | 0.083 | 0.132 | 0.098 |
| 100 + 600 | 100 | 600 | 0.09 | 0.32 | 0.152 |
| 50 + 300 | 50 | 300 | 0.097 | 0.483 | 0.231 |
| 25 + 150 | 25 | 150 | 0.101 | 0.605 | 0.419 |
| 12.5 + 75 | 12.5 | 75 | 0.136 | 0.708 | 0.632 |
| 6.25 + 37.5 | 6.25 | 37.5 | 0.279 | 0.806 | 0.769 |
| 3.125 + 18.75 | 3.125 | 18.75 | 0.527 | 0.832 | 0.849 |
| 1.5625 + 9.375 | 1.5625 | 9.375 | 0.739 | 0.874 | 0.881 |
| 0.78125 + 4.6875 | 0.78125 | 4.6875 | 0.868 | 0.901 | 0.896 |

Table 29 and FIG. 29 show that the ginsenoside Rg5 blank liposome had better activity against paclitaxel-resistant human lung cancer cell line (A549/T), Taxol+Rg5 had enhanced activity against paclitaxel-resistant human lung cancer cell line (A549/T) relative to conventional paclitaxel injection which showed a lower cell survival rate, especially in low doses.

2. According to the assay of $IC_{50}$, the $IC_{50}$ of blank Rg5, Taxol and Taxol+Rg5 against human lung cancer cell line (A549) and paclitaxel-resistant human lung cancer cell line (A549/T) were tested respectively. The experimental data are shown in Table 30.

TABLE 30

| Cell line | Blank Rg5 | Taxol | Taxol + Rg5 |
|---|---|---|---|
| A549/T | 106.05 μM | 29.99 μM | 4.357 μM (26.14 μM) |
| A549 | 10.68 μM | 77.46 nM | 65.73 nM (0.3944 μM) |

Notes:
In 4.357 μM (26.14 μM) of the corresponding $IC_{50}$ value of Taxol + Rg5: 4.357 μM means the $IC_{50}$ value of Taxol and 26.14 μM means the $IC_{50}$ value of blank Rg5.

Table 30 showed that the activity of Taxol+Rg5 was enhanced 1.1-1.2 times that of conventional Taxol injection against human lung cancer cell line (A549), and the activity of Taxol+Rg5 was enhanced 6-8 times that of conventional paclitaxel injection against Taxol-resistant human lung cancer cell line (A549/T).

3. Cell Uptake Experiment In Vitro

DAPI is a kind of fluorescent dye which can penetrate cell membrane and bind with double-strand DNA in cell nucleus so that it could have a mark function and produce 20 times the fluorescence of DAPI itself. Compared to EB, the sensitivity of staining double-strand DNA is enhanced for multiple times. Cells with blue fluorescence could be observed through microscope and high efficiency of cell labeling is observed by a fluorescence microscope (almost 100%). DAPI is often used for normal cell nuclear staining and double-strand DNA staining in particular cases. Cells are stained with DAPI for 3 minutes after heat shock treatment, a morphological change of the cell nucleus could be observed through a fluorescence microscope. After being stained with DAPI, cell nucleus with blue fluorescence could be observed through a fluorescence microscope. Under specific condition, when the cells stained by DIPA were put into a Nile red culture-medium, the cells can absorb Nile red. After superposition of red fluorescence and blue fluorescence, blue-violet fluorescence could be generated. An uptake amount of Nile red could be determined according to the strength of the blue-violet fluorescence.

Figure 30:
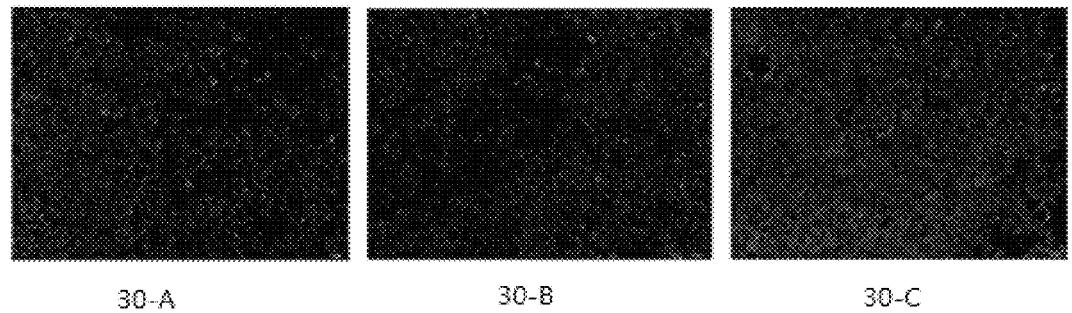
FIG. 30 is a fluorescent inverted microscope observation figure of tumor cell uptake, wherein FIG. 30-A, FIG. 30-B, FIG. 30-C are respectively the fluorescent inverted microscope observation figures of Nil, Nil-lip, Rg5-Nil-lip against paclitaxel-resistant human lung cancer cell line (A549/T).

Paclitaxel-resistant human lung cancer cell line (A549/T) was inoculated in a 24-well plate and cultured overnight. Nil (free Nile red), Nil-Lip and Rg5-Nil-Lip were used to prepare a culture-medium containing equivalent amount of Nil (10 μg·mL$^{-1}$) with serum-free culture medium, and were added into each well while light was avoided. Each group was for 8 wells. The culture medium was discarded after the cells were cultured for 2 hours while light was avoided, then washed for 3 times by PBS. The first 4 wells in each group were fixed for 30 minutes at 37° C. with 4% paraformaldehyde, then washed with PBS for 3 times, stained with DAPI (4,6-diamidino-2-phenylindol), washed with PBS (phosphate buffer) for 3 times and observed with fluorescent inverted microscope, see FIG. 30. FIG. 30-A, FIG. 30-B, FIG. 30-C were respectively the fluorescent inverted microscope observation figures of Nil, Nil-lip, Rg5-Nil-lip. Nil=Free Nile red; Nil-lip=Nil red liposome (i.e. the Nil red encapsulated by a conventional blank liposome); Rg5-Nil-lip=Nil red Rg5 liposome (i.e. the Nil red encapsulated by ginsenoside Rg5 blank liposome, see embodiment 4 in detail wherein paclitaxel was replaced by Nil red).

FIG. 30-A shows blue fluorescence, FIG. 30-B shows a little fuchia fluorescence and FIG. 30-C shows almost fuchia fluorescence. It can be seen that the uptake of ginsenoside Rg5 liposome by paclitaxel-resistant human lung cancer cell line (A549/T) was increased significantly.

4. Small Animal Imaging System In Vivo

BALB/C-nu/nu mice bearing tumors in uniform size of 100 mm$^3$ at left forelimbs without hemorrhagic necrosis, intravenously injected at tail with a ginsenoside Rg5 liposome containing 10% of near-infrared fluorescent probe (IR783) (hereinafter abbreviated as the experimental group, which was obtained by encapsulating near-infrared fluorescent probe (IR783) into the ginsenoside Rg5 blank liposome, see embodiment 4 in detail wherein paclitaxel was replaced by near-infrared fluorescent probe (IR783)) and an conventional liposome containing near-infrared fluorescent probe (IR783) (hereinafter abbreviated as the control group, which was obtained by encapsulating near-infrared fluorescent probe (IR783) into a conventional blank liposome, the process was a conventional process for preparing a liposome loading near-infrared fluorescent probe (IR783) in this field)

respectively. The distributions in vivo of IR783 fluorescence were recorded by a live imager at 2nd, 6th and 10th hour, see FIG. 31 and FIG. 32. FIG. 31-A, FIG. 31-B and FIG. 31-C were respectively the figures of distribution in vivo of IR783 fluorescence of the control group recorded at 2nd, 6th and 10th hour by the live imager. FIG. 31-G is a fluorescence ruler, wherein according to the fluorescence intensity, color is red, yellow, green and blue in sequence, red indicates the strongest fluorescence, blue indicates weak fluorescence. FIG. 31-D, FIG. 31-E and FIG. 31-F were respectively the figures of distribution in vivo of IR783 fluorescence of the experimental group recorded at 2nd, 6th and 10th hour by the live imager. It can be seen from FIG. 31 that the left forelimbs of the mice in the control group had no fluorescence, while the left forelimbs of the mice in the experimental group had strong fluorescence, which showed that ginsenoside Rg5 blank liposome had very strong ability to target tumor cells.

FIG. 32 was the fluorescence figure of the isolated viscera of the control group mice and the experimental group mice. After the imaging experiment in vivo, the main viscera and tumors were taken out from mice of the control and experimental groups to make further fluorescence detection in vitro. FIG. 32-A and FIG. 32-B were respectively the fluorescence figures of the isolated viscera of the control group mice and the experimental group mice. FIG. 32-C is a fluorescence ruler, wherein according to the fluorescence intensity, color is red, yellow, green and blue in sequence, red indicates the strongest fluorescence, blue indicates weak fluorescence. The tumors fluorescence in FIG. 32-B was strong, which suggested ginsenoside Rg5 blank liposome had strong targetability to tumor cells.

FIGS. 31 and 32 showed an enhanced targetability of ginsenoside Rg5 blank liposome to A549 lung cancer.

5. Pharmacological Efficacy Experiment In Vivo

According to the assay of pharmacological efficacy experiment in vivo, 27 subcutaneous tumor-burdened nude mice were randomly divided into 3 groups (9 in each group), a control group (Control group, 0.9% NaCl), a Taxol+Rg5 group (ginsenoside Rg5 paclitaxel liposome) and an Abraxane group (albumin-Taxol group, abbreviated as Abr). Corresponding preparations were injected via tail vein (a dose of 25 mg·kg$^{-1}$). The changes of body weights of mice in each group were recorded every 2 days, and the longest diameter and the shortest diameter of tumors were measured with a vernier caliper. The tumor volume is calculated by the following formula: V=(dmax×dmin$^2$)/2, wherein dmin and dmax are respectively the shortest diameter and the longest diameter (mm) of the tumor; a relative tumor volume (RTV) is calculated according to the measurement results, the calculation formula is: RTV=Vt/V0. Wherein V0 was the tumor volume measured when the mouse started to be administered and Vt was the tumor volume measured every 2 days.

5.1 Compare the antitumor effect (pharmacological efficacy) of the control group, Taxol+Rg5 group and Abraxane group against human lung cancer cell line (A549). The detailed experimental data were shown in Table 31 and FIG. 33. Wherein FIG. 33 was the antitumor graph of the control group, Taxol+Rg5 group and Abraxane group against human lung cancer cell line (A549).

TABLE 31

Antitumor effect of the control group, Taxol + Rg5 group and Abraxane group against human lung cancer cell line (A549)

| A549 Time (d) | Relative tumor volume | | | | | |
|---|---|---|---|---|---|---|
| | Control | SD | Taxol + Rg5 | SD | Abraxane | SD |
| 0 | 1 | 0.171 | 1 | 0.247 | 1 | 0.159 |
| 3 | 2.136 | 0.308 | 1.307 | 0.372 | 1.308 | 0.406 |
| 6 | 2.752 | 1.029 | 1.581 | 0.341 | 1.804 | 0.454 |
| 9 | 4.478 | 0.453 | 1.805 | 0.315 | 2.473 | 0.367 |
| 12 | 5.289 | 0.768 | 2.217 | 0.353 | 2.853 | 0.454 |
| 15 | 7.043 | 1.089 | 2.33 | 0.519 | 3.273 | 0.607 |
| 18 | 9.675 | 1.385 | 2.505 | 0.604 | 3.704 | 0.595 |
| 21 | 12.274 | 1.734 | 2.77 | 0.852 | 4.198 | 0.783 |

Table 31 and FIG. 33 showed that after the same period of time, the volume of tumor in the control group was the maximum while in the Taxol+Rg5 group was the minimum. With time delaying, the volume of tumor in the control group reached 12.274, while the Taxol+Rg5 group only 2.77, and the Abraxane group was 4.198 on 21$^{st}$ day. This suggested that the pharmacological efficacy of Taxol+Rg5 was slightly stronger than Abraxane for human lung cancer A549 tumor-bearing mice.

5.2. Compare antitumor effect (pharmacological efficacy) of the control group, Taxol+Rg5 group and Abraxane group against paclitaxel-resistant human lung cancer cell line (A549/T). The detailed experimental data were shown in Table 32 and FIG. 34. FIG. 34 was the antitumor graph of the control group, Taxol+Rg5 group and Abraxane group against paclitaxel-resistant human lung cancer cell line (A549/T).

TABLE 32 antitumor effect of the control group, Taxol + Rg5 group and Abraxane group against paclitaxel-resistant human lung cancer cell line (A549/T)

| A549/T Time (d) | Relative tumor volume | | | | | |
|---|---|---|---|---|---|---|
| | Control | SD | Taxol + Rg5 | SD | Abraxane | SD |
| 0 | 1 | 0.271 | 1 | 0.247 | 1 | 0.259 |
| 4 | 3.166 | 0.308 | 2.107 | 0.272 | 2.308 | 0.306 |
| 7 | 4.752 | 1.029 | 2.381 | 0.441 | 3.604 | 0.454 |
| 11 | 7.978 | 0.453 | 3.605 | 0.315 | 4.773 | 0.567 |
| 14 | 11.289 | 0.768 | 4.217 | 0.553 | 6.273 | 0.454 |
| 18 | 16.543 | 1.789 | 4.383 | 0.619 | 8.533 | 0.807 |
| 21 | 20.975 | 2.485 | 4.825 | 0.804 | 11.504 | 1.165 |

Table 32 and FIG. 34 showed that after the same period of time, the volume of tumor in the control group was the maximum while in the Taxol+Rg5 group was the minimum. With time delaying, the volume of tumor in the control group reached 20.975, while the Taxol+Rg5 group only 4.825, and the Abraxane group was 11.504 on 21$^{st}$ day. This suggested that the pharmacological efficacy of the Taxol+ Rg5 on paclitaxel-resistant human lung cancer A549/T tumor-bearing mice was significantly improved compared to Abraxane.

6. Anti-Tumor Metastasis Experiment of Ginsenoside Rg5 Paclitaxel Liposome (A549/T)

After the mice bearing paclitaxel-resistant human lung cancer cell line (A549/T) and the normal mice in the control group and Taxol+Rg5 group in the pharmacological experiment in vivo were sacrificed, the corresponding viscera or tumor tissues were taken for paraffin section, stained by hematoxylin-eosin and observed under an optical microscope, see FIG. 35. FIG. 35-A, FIG. 35-D and FIG. 35-G were respectively the microscope observation figures of the paraffin sections of lung, liver and tumor tissue of normal mice after stained by hematoxylin-eosin, FIG. 35-B, FIG. 35-E and FIG. 35-H were respectively the microscope observation figures of the paraffin sections of lung, liver and tumor tissue of tumor-bearing mice in the control group after stained by hematoxylin-eosin, FIG. 35-C, FIG. 35-F and FIG. 35-I were respectively the microscope observation figures of lung, liver and tumor tissue of the paraffin sections of the mice in the experimental group (after the treatment with ginsenoside Rg5 paclitaxel liposome) after stained by hematoxylin-eosin.

FIG. 35-A, FIG. 35-B and FIG. 35-C showed that after the paraffin sections of lung tissue of the mice in the experimental group were stained by hematoxylin-eosin, the color distribution was the same as that of normal mice, which suggested that there was no tumor metastasis in the experimental group mice. However, after the paraffin sections of mice in the control group were stained by hematoxylin-eosin, the color distribution was not uniform, which suggested that there was tumor metastasis in the control group mice.

FIG. 35 showed that the Taxol+Rg5 had a better inhibition effect on lung tumor metastasis of A549/T.

Application Embodiment 2

According to the assay of cell experiment in vitro, the effects of Taxol, blank Rg5 and Taxol+Rg5 against human breast cancer cell line (MCF-7) and paclitaxel-resistant human breast cancer cell line (MCF-7/T) were tested in cell experiment in vitro and in animal experiment in vivo.

1. Pharmacological Efficacy Experimental Assay In Vitro

According to the assay of cell experiment in vitro, 9 different concentrations were set as shown in Table 33 and Table 32. The specific survival rate data and graphs were shown in Table 33-34 and FIG. 36-37. FIG. 36 was the cell survival rate graph of Taxol, blank Rg5 and Taxol+Rg5 against human breast cancer cell line (MCF-7) respectively. FIG. 37 was the cell survival rate graph of Taxol, blank Rg5 and Taxol+Rg5 against paclitaxel-resistant human breast cancer cell line (MCF-7/T) respectively.

TABLE 33

Cell survival rates of Taxol, blank Rg5 and Taxol + Rg5 against human breast cancer cell line (MCF-7)

| C (μM) | | | Cell Viability | | |
|---|---|---|---|---|---|
| Taxol + Rg5 | Taxol | Blank Rg5 | Taxol + Rg5 | Taxol | Blank Rg5 |
| 1 + 6 | 1 | 6 | 0.109 | 0.112 | 0.751 |
| 0.5 + 3 | 0.5 | 3 | 0.115 | 0.132 | 0.785 |
| 0.25 + 1.5 | 0.25 | 1.5 | 0.198 | 0.205 | 0.807 |
| 0.125 + 0.75 | 0.125 | 0.75 | 0.302 | 0.331 | 0.813 |
| 0.0625 + 0.375 | 0.0625 | 0.375 | 0.503 | 0.529 | 0.821 |
| 0.03125 + 0.1875 | 0.03125 | 0.1875 | 0.614 | 0.637 | 0.846 |
| 0.015625 + 0.09375 | 0.015625 | 0.09375 | 0.721 | 0.744 | 0.853 |
| 0.007813 + 0.046875 | 0.007813 | 0.046875 | 0.828 | 0.849 | 0.879 |
| 0.003906 + 0.023438 | 0.003906 | 0.023438 | 0.863 | 0.878 | 0.8583 |

Table 33 and FIG. 36 showed that activity of ginsenoside Rg5 blank liposome was relatively weak against MCF-7, and tumor cells had high survival rate, while the activity of Taxol+Rg5 was slightly stronger than conventional paclitaxel injection against MCF-7 live cells in vitro, and tumor cells had low survival rate.

TABLE 34

Cell survival rates of Taxol, blank Rg5 and Taxol + Rg5 against paclitaxel-resistant human breast cancer cell line (MCF-7/T)

| C (μM) | | | Viability | | |
|---|---|---|---|---|---|
| Taxol + Rg5 | Taxol | Blank Rg5 | Taxol + Rg5 | Taxol | Blank Rg5 |
| 400 + 2400 | 400 | 2400 | 0.09 | 0.109 | 0.091 |
| 200 + 1200 | 200 | 1200 | 0.093 | 0.1222 | 0.105 |
| 100 + 600 | 100 | 600 | 0.095 | 0.157 | 0.117 |
| 50 + 300 | 50 | 300 | 0.104 | 0.237 | 0.203 |
| 25 + 150 | 25 | 150 | 0.164 | 0.419 | 0.361 |
| 12.5 + 75 | 12.5 | 75 | 0.227 | 0.584 | 0.5256 |
| 6.25 + 37.5 | 6.25 | 37.5 | 0.431 | 0.709 | 0.6553 |
| 3.125 + 18.75 | 3.125 | 18.75 | 0.762 | 0.856 | 0.7979 |
| 1.5625 + 9.375 | 1.5625 | 9.375 | 0.865 | 0.893 | 0.8583 |

Table 34 and FIG. 37 showed that ginsenoside Rg5 blank liposome had better activity against Taxol-resistant human breast cancer cell line (MCF-7/T), and Taxol+Rg5 had stronger activity than conventional paclitaxel injection against paclitaxel-resistant human breast cancer cell line (MCF-7/T), cell survival rate of which is lower, especially in low doses.

2. According to the assay of $IC_{50}$, the $IC_{50}$ of blank Rg5, Taxol and Taxol+Rg5 against human breast cancer cell line (MCF-7) and paclitaxel-resistant human breast cancer cell line (MCF-7/T) was tested. The experimental data were shown in Table 35.

TABLE 35

| Cell line | Blank Rg5 | Taxol | Taxol + Rg5 |
|---|---|---|---|
| MCF-7/T | 86.24 μM | 18.77 μM | 7.800 μM (46.80 μM) |
| MCF-7 | 11.29 μM | 58.90 nM | 52.41 nM (0.3145 μM) |

Table 35 showed that activity of Taxol+Rg5 was enhanced 1.1-1.2 times that of conventional paclitaxel injection against human breast cancer cell line (MCF-7), and the activity of Taxol+Rg5 was enhanced 2-3 times that of conventional paclitaxel injection against paclitaxel-resistant human breast cancer cell line (MCF-7/T).

3. Pharmacological Efficacy Experiment In Vivo 27 subcutaneous tumor-bearing mice were randomly divided into 3 groups (9 in each group), the control group (Control group, 0.9% NaCl), the Taxol+Rg5 group (ginsenoside Rg5 paclitaxel liposome) and the Abraxane group (albumin-Taxol group, abbreviated as Abr). Corresponding preparations were injected via tail vein (a dose of 25 mg·kg$^{-1}$). The changes of body weights of mice in each group were recorded every 2 days, and the longest diameter and the shortest diameter of tumors were measured with a vernier caliper. The tumor volume is calculated by the following formula: V=(dmax×dmin$^2$)/2, wherein dmin and dmax are respectively the shortest diameter and the longest diameter (mm) of the tumor; a relative tumor volume (RTV) is calculated according to the measurement results, the calculation formula is: RTV=Vt/V0, wherein, V0 was the tumor volume measured when the mouse started to be administered and Vt was the tumor volume measured every 2 days.

3.1 Compare antitumor effects (pharmacological efficacy) of the control group, Taxol+Rg5 group and Abraxane group against human breast cancer cell line (MCF-7). The detailed experimental data were shown in Table 36 and FIG. 38. FIG. 38 showed the antitumor graph of the control group, Taxol+Rg5 group and Abraxane group against human breast cancer cell line (MCF-7).

TABLE 36

Antitumor effect of the control group, Taxol + Rg5 group and Abraxane group against human breast cancer cell line (MCF-7)

| MCF-7 | Relative tumor volume | | | | | |
|---|---|---|---|---|---|---|
| Time (d) | Control | SD | Taxol + Rg5 | SD | Abraxane | SD |
| 0 | 1 | 0.592 | 1 | 0.247 | 1 | 0.269 |
| 4 | 1.736 | 0.651 | 1.251 | 0.27 | 1.34 | 0.173 |
| 7 | 3.358 | 0.824 | 1.32 | 0.327 | 1.58 | 0.248 |
| 11 | 6.127 | 0.833 | 1.76 | 0.292 | 2.19 | 0.28 |
| 14 | 6.783 | 1.163 | 1.82 | 0.25 | 2.61 | 0.317 |
| 18 | 7.472 | 1.056 | 2.17 | 0.231 | 2.99 | 0.282 |
| 21 | 8.214 | 1.403 | 2.64 | 0.243 | 3.51 | 0.293 |

Table 36 and FIG. 38 showed that after the same period of time, the volume of tumor in the control group was the maximum while in the Taxol+Rg5 group was the minimum. With time delaying, the volume of tumor in the control group reached 8.214, while the Taxol+Rg5 group only 2.64, and the Abraxane group was 3.51 on $21^{st}$ day. This suggested that the pharmacological efficacy of Taxol+Rg5 was slightly stronger than Abraxane for human breast cancer MCF-7 tumor-bearing mice.

3.2 Compare antitumor effect (pharmacological efficacy) of the control group, Taxol+Rg5 group and Abraxane group against paclitaxel-resistant human breast cancer cell line (MCF-7/T). The detailed experimental data were shown in Table 37 and FIG. 39. FIG. 39 was the antitumor graph of the control group, Taxol+Rg5 group and Abraxane group against paclitaxel-resistant human breast cancer cell line (MCF-7/T).

TABLE 37

Antitumor effect of the control group, Taxol + Rg5 group and Abraxane group against Paclitaxel-resistant human breast cancer cell line (MCF-7/T)

| MCF-7/T | Relative tumor volume | | | | | |
|---|---|---|---|---|---|---|
| Time (d) | Control | SD | Taxol + Rg5 | SD | Abraxane | SD |
| 0 | 1 | 0.592 | 1 | 0.336 | 1 | 0.375 |
| 2 | 2.136 | 0.65 | 1.35 | 0.54 | 1.34 | 0.286 |
| 4 | 3.758 | 0.824 | 1.42 | 0.367 | 2.58 | 0.357 |
| 6 | 5.127 | 0.833 | 2.16 | 0.492 | 3.19 | 0.54 |
| 8 | 7.783 | 1.163 | 2.32 | 0.45 | 4.64 | 0.847 |
| 10 | 10.072 | 1.956 | 2.87 | 0.831 | 5.79 | 1.582 |
| 12 | 15.214 | 1.603 | 3.64 | 0.853 | 6.81 | 1.293 |
| 14 | 22.157 | 2.429 | 4.32 | 1.358 | 8.78 | 1.685 |

Table 37 and FIG. 39 showed that after the same period of time, the volume of tumor in the control group was the maximum while in the Taxol+Rg5 group was the minimum. With time delaying, the volume of tumor in the control group reached 22.157, while the Taxol+Rg5 group only 4.32, and the Abraxane group was 8.78 on $14^{th}$ day. This suggested that the pharmacological efficacy of Taxol+Rg5 on paclitaxel-resistant human breast cancer MCF-7/T tumor-bearing mice was significantly improved compared to Abraxane.

Application Embodiment 3: Cell Experiment In Vitro for Ginsenosides Rg5 Paclitaxel Liposome Against Human Ovarian Cancer Cell Line (A2780)/Paclitaxel-Resistant Human Ovarian Cancer Cell Line (A2780/T)

1. Pharmacological Efficacy Experimental Assay In Vitro

According to the assay of cell experiment in vitro, survival rates of Taxol, blank Rg5, Taxol+Rg5 and Abraxane against human ovarian cancer cell line (A2780)/paclitaxel-resistant human ovarian cancer cell line (A2780/T) respectively were tested. 10 Different drug concentrations were set as shown in Table 30 and Table 31. Detailed survival rate data and graphs were shown in Table 38 and Table 39, FIG. 40 and FIG. 41. FIG. 40 was the cell survival rate graph of Taxol, blank Rg5, Taxol+Rg5 and Abraxane against human ovarian cancer cell line (A2780) respectively. FIG. 41 was the cell survival rate graph of Taxol, blank Rg5, Taxol+Rg5 and Abraxane against paclitaxel-resistant human ovarian cancer cell line (A2780/T) respectively.

TABLE 38

Cell survival rates of Taxol, blank Rg5, Taxol + Rg5 and Abraxane against ovarian cancer cell line (A2780)

| C (μM) | | | | Cell Viability | | | |
|---|---|---|---|---|---|---|---|
| Taxol + Rg5 | Taxol | Blank Rg5 | Abraxane | Taxol + Rg5 | Taxol | Blank Rg5 | Abraxane |
| 1 + 6 | 1 | 6 | 1 | 0.128 | 0.133 | 0.834 | 0.148 |
| 0.5 + 3 | 0.5 | 3 | 0.5 | 0.174 | 0.185 | 0.847 | 0.184 |
| 0.25 + 1.5 | 0.25 | 1.5 | 0.25 | 0.198 | 0.204 | 0.824 | 0.228 |
| 0.125 + 0.75 | 0.125 | 0.75 | 0.125 | 0.274 | 0.282 | 0.844 | 0.314 |
| 0.0625 + 0.375 | 0.0625 | 0.375 | 0.0625 | 0.304 | 0.324 | 0.853 | 0.374 |
| 0.03125 + 0.1875 | 0.03125 | 0.1875 | 0.03125 | 0.413 | 0.443 | 0.848 | 0.463 |
| 0.015625 + 0.09375 | 0.015625 | 0.09375 | 0.015625 | 0.634 | 0.673 | 0.846 | 0.724 |
| 0.007813 + 0.046875 | 0.007813 | 0.046875 | 0.007813 | 0.806 | 0.818 | 0.868 | 0.836 |
| 0.003906 + 0.02343 | 0.003906 | 0.023438 | 0.003906 | 0.827 | 0.847 | 0.871 | 0.866 |
| 0.001953 + 0.011719 | 0.001953 | 0.011719 | 0.001953 | 0.853 | 0.866 | 0.882 | 0.874 |

Table 38 and FIG. 40 showed that activity of ginsenoside Rg5 blank liposome was relatively weak against human ovarian cancer cell line (A2780), and the activity of Taxol+Rg5 was slightly stronger than conventional paclitaxel injection and Abraxane against human ovarian cancer cell line (A2780) in vitro.

Table 40 showed that the activity of Taxol+Rg5 was enhanced 1.1-1.5 times that of paclitaxel and Abraxane injection against human ovarian cancer cell line (A2780), and the activity of Taxol+Rg5 was enhanced 3-5 times that of paclitaxel and Abraxane injection against paclitaxel-resistant human ovarian cancer cell line (A2780/T).

TABLE 39

Cell survival rates of Taxol, blank Rg5, Taxol + Rg5 and Abraxane against paclitaxel-resistant human ovarian cancer cell line (A2780/T)

| C (μM) | | | | Cell Viability | | | |
|---|---|---|---|---|---|---|---|
| Taxol + Rg5 | Taxol | Blank Rg5 | Abraxane | Taxol + Rg5 | Taxol | Blank Rg5 | Abraxane |
| 400 + 2400 | 400 | 2400 | 400 | 0.086 | 0.139 | 0.094 | 0.148 |
| 200 + 1200 | 200 | 1200 | 200 | 0.091 | 0.174 | 0.097 | 0.184 |
| 100 + 600 | 100 | 600 | 100 | 0.095 | 0.198 | 0.124 | 0.228 |
| 50 + 300 | 50 | 300 | 50 | 0.099 | 0.274 | 0.168 | 0.314 |
| 25 + 150 | 25 | 150 | 25 | 0.108 | 0.304 | 0.203 | 0.374 |
| 12.5 + 75 | 12.5 | 75 | 12.5 | 0.121 | 0.393 | 0.288 | 0.463 |
| 6.25 + 37.5 | 6.25 | 37.5 | 6.25 | 0.17 | 0.654 | 0.436 | 0.724 |
| 3.125 + 18.75 | 3.125 | 18.75 | 3.125 | 0.436 | 0.806 | 0.648 | 0.836 |
| 1.5625 + 9.375 | 1.5625 | 9.375 | 1.5625 | 0.733 | 0.856 | 0.811 | 0.866 |
| 0.78125 + 4.6875 | 0.78125 | 4.6875 | 0.78125 | 0.846 | 0.874 | 0.882 | 0.874 |

Table 39 and FIG. 41 showed that ginsenoside Rg5 blank liposome had better activity against paclitaxel-resistant human ovarian cancer cell line (A2780/T), and the activity of Taxol+Rg5 was stronger than that of conventional paclitaxel injection and Abraxane against paclitaxel-resistant human ovarian cancer cell line (A2780/T).

2. According to the assay of $IC_{50}$, the $IC_{50}$ of blank Rg5, Taxol, Taxol+Rg5 and Abraxane against human ovarian cancer cell line (A2780) and paclitaxel-resistant human ovarian cancer cell line (A2780/T) was tested. The experimental data were shown in Table 40.

TABLE 40

| Cell line | Blank Rg5 | Taxol | Taxol + Rg5 | Abraxane |
|---|---|---|---|---|
| A2780/T | 44.44 μM | 14.11 μM | 3.764 μM (22.59 μM) | 17.88 μM |
| A2780 | 40.79 μM | 37.81 nM | 33.64 nM (0.2018 μM) | 48.44 nM |

Application Embodiment 4 Cell Experiment In Vitro for Ginsenosides Rg5 Paclitaxel Liposome Against Human Prostate Cancer Cell Line (PC-3)/Paclitaxel-Resistant Human Prostate Cancer Cell Line (PC-3/T)

1. Pharmacological Efficacy Experimental Assay In Vitro

According to the assay of cell experiment in vitro, survival rates of Taxol, blank Rg5, Taxol+Rg5 and Abraxane against human prostate cancer cell line (PC-3)/paclitaxel-resistant human prostate cancer cell line (PC-3/T) respectively were tested. 10 Different drug concentrations were set as shown in Table 41 and Table 42. Detailed survival rate data and graphs were shown in Table 41, 42 and FIG. 42, 43. FIG. 42 was the cell survival rate graph of Taxol, blank Rg5, Taxol+Rg5 and Abraxane against human prostate cancer cell line (PC-3) respectively. FIG. 43 was the cell survival rate graph of Taxol, blank Rg5, Taxol+Rg5 and Abraxane against paclitaxel-resistant human prostate cancer cell line (PC-3/T) respectively.

TABLE 41

Cell survival rates of Taxol, Rg5, Taxol + Rg5 and Abraxane against human prostate cancer cell line (PC-3)

| C (μM) | | | | Cell Viability | | | |
|---|---|---|---|---|---|---|---|
| Taxol + Rg5 | Taxol | Blank Rg5 | Abraxane | Taxol + Rg5 | Taxol | Blank Rg5 | Abraxane |
| 15 + 90 | 15 | 90 | 15 | 0.108 | 0.113 | 0.133 | 0.123 |
| 7.5 + 45 | 7.5 | 45 | 7.5 | 0.109 | 0.116 | 0.284 | 0.125 |
| 3.75 + 22.5 | 3.75 | 22.5 | 3.75 | 0.113 | 0.125 | 0.55 | 0.134 |
| 1.875 + 11.25 | 1.875 | 11.25 | 1.875 | 0.131 | 0.143 | 0.714 | 0.158 |
| 0.9375 + 5.625 | 0.9375 | 5.625 | 0.9375 | 0.171 | 0.187 | 0.803 | 0.197 |
| 0.46875 + 2.8125 | 0.46875 | 2.8125 | 0.46875 | 0.213 | 0.223 | 0.826 | 0.261 |
| 0.234375 + 1.40625 | 0.234375 | 1.40625 | 0.234375 | 0.311 | 0.307 | 0.838 | 0.381 |
| 0.117188 + 0.703125 | 0.117188 | 0.703125 | 0.117188 | 0.422 | 0.389 | 0.843 | 0.469 |
| 0.058594 + 0.351563 | 0.058594 | 0.351563 | 0.058594 | 0.607 | 0.593 | 0.844 | 0.633 |
| 0.029297 + 0.175781 | 0.029297 | 0.175781 | 0.029297 | 0.793 | 0.813 | 0.845 | 0.837 |

Table 41 and FIG. 42 showed that the activity of ginsenoside Rg5 blank liposome was relatively weak against human prostate cancer cell line (PC-3) in low doses, but stronger in high doses. The activity of Taxol+Rg5 had no significant difference with that of conventional paclitaxel injection and Abraxane injection against human prostate cancer cell line (PC-3).

TABLE 42

Cell survival rates of Taxol, blank Rg5, Taxol + Rg5 and Abraxane against paclitaxel-resistant human prostate cancer cell line (PC-3/T)

| C (μM) | | | | Cell Viability | | | |
|---|---|---|---|---|---|---|---|
| Taxol + zRg5 | Taxol | Blank Rg5 | Abraxane | Taxol + Rg5 | Taxol | Blank Rg5 | Abraxane |
| 50 + 300 | 50 | 300 | 50 | 0.108 | 0.484 | 0.107 | 0.464 |
| 25 + 150 | 25 | 150 | 25 | 0.146 | 0.563 | 0.128 | 0.513 |
| 12.5 + 75 | 12.5 | 75 | 12.5 | 0.143 | 0.713 | 0.235 | 0.673 |
| 6.25 + 37.5 | 6.25 | 37.5 | 6.25 | 0.181 | 0.807 | 0.55 | 0.787 |
| 3.125 + 18.75 | 3.125 | 18.75 | 3.125 | 0.191 | 0.843 | 0.749 | 0.833 |
| 1.5625 + 9.375 | 1.5625 | 9.375 | 1.5625 | 0.293 | 0.853 | 0.853 | 0.843 |
| 0.78125 + 4.6875 | 0.78125 | 4.6875 | 0.78125 | 0.441 | 0.868 | 0.865 | 0.848 |
| 0.390625 + 2.34375 | 0.390625 | 2.34375 | 0.390625 | 0.522 | 0.882 | 0.878 | 0.892 |
| 0.195313 + 1.171875 | 0.195313 | 1.171875 | 0.195313 | 0.607 | 0.881 | 0.883 | 0.871 |
| 0.097656 + 0.585938 | 0.097656 | 0.585938 | 0.097656 | 0.693 | 0.887 | 0.884 | 0.857 |

Table 42 and FIG. 43 showed that activity of ginsenoside Rg5 blank liposome was relatively strong against Taxol-resistant human prostate cancer cell line (PC-3/T) in high doses. The activity of Taxol+Rg5 had obvious advantages compared to that of conventional paclitaxel injection and Abraxane injection against paclitaxel-resistant human prostate cancer cell line (PC-3/T).

2. According to the assay of $IC_{50}$, the $IC_{50}$ of blank Rg5, Taxol, Taxol+Rg5 and Abraxane against human prostate cancer cell line (PC-3) and paclitaxel-resistant human prostate cancer cell line (PC-3/T) was tested respectively. The experimental data were shown in Table 43.

TABLE 43

| Cell line | Blank Rg5 | Taxol | Taxol + Rg5 | Abraxane |
|---|---|---|---|---|
| PC-3/T | 29.01 μM | 16.20 μM | 0.6685 μM (4.011 μM) | 13.98 μM |
| PC-3 | 12.70 μM | 164.6 nM | 160.4 nM (0.9627 μM) | 205.2 nM |

Table 43 showed that activity of Taxol+Rg5 was enhanced 1.0-1.5 times that of paclitaxel injection and Abraxane injection against human prostate cancer cell line (PC-3), and the activity of Taxol+Rg5 was enhanced 20-30 times that of paclitaxel injection and Abraxane injection against paclitaxel-resistant human prostate cancer cell line (PC-3/T).

Application Embodiment 5 Cell Experiment In Vitro for Ginsenosides Rg5 Paclitaxel Liposome Against Human In Situ Pancreatic Cancer Cell Line (BxPC-3)/Paclitaxel-Resistant Pancreatic Cancer Cell Line (BxPC-3/T)

1. Pharmacological Efficacy Experimental Assay In Vitro

According to the assay of cell experiment in vitro, survival rates of Taxol, blank Rg5 and Taxol+Rg5 against human pancreatic cancer cell line (BxPC-3)/paclitaxel-resistant human pancreatic cancer cell line (BxPC-3/T) respectively were tested. 9 different drug concentrations were set as shown in Table 44 and Table 45. Detailed survival rate data and graphs were shown in Table 44 and Table 45, FIG. 44 and FIG. 45. FIG. 44 was the cell survival rate graph of Taxol, blank Rg5 and Taxol+Rg5 against human pancreatic cancer cell line (BxPC-3). FIG. 45 was the cell survival rate graph of Taxol, blank Rg5 and Taxol+Rg5 against paclitaxel-resistant human pancreatic cancer cell line (BxPC-3/T).

TABLE 44

Cell survival rates of Taxol, blank Rg5 and Taxol + Rg5 against human pancreatic cancer cell line (BxPC-3)

| C (μM) | | | Cell Viability | | |
|---|---|---|---|---|---|
| Taxol + Rg5 | Taxol | Blank Rg5 | Taxol + Rg5 | Taxol | Blank Rg5 |
| 400 + 2400 | 400 | 2400 | 0.096 | 0.097 | 0.132 |
| 200 + 1200 | 200 | 1200 | 0.115 | 0.149 | 0.166 |
| 100 + 600 | 100 | 600 | 0.132 | 0.166 | 0.228 |
| 50 + 300 | 50 | 300 | 0.135 | 0.202 | 0.281 |
| 25 + 150 | 25 | 150 | 0.242 | 0.254 | 0.341 |
| 12.5 + 75 | 12.5 | 75 | 0.297 | 0.339 | 0.434 |
| 6.25 + 37.5 | 6.25 | 37.5 | 0.387 | 0.426 | 0.632 |
| 3.125 + 18.75 | 3.125 | 18.75 | 0.588 | 0.632 | 0.749 |
| 1.5625 + 9.375 | 1.5625 | 9.375 | 0.85 | 0.85 | 0.822 |

Table 44 and FIG. 44 showed that activity of ginsenoside Rg5 blank liposome was relatively strong against human pancreatic cancer cell line (BxPC-3). The activity of Taxol+Rg5 was stronger than that of conventional paclitaxel injection against human pancreatic cancer cell line (BxPC-3).

TABLE 45

Cell survival rates of Taxol, blank Rg5 and Taxol + Rg5 against paclitaxel-resistant human pancreatic cancer cell line (BxPC-3/T)

| C (μM) | | | Cell Viability | | |
|---|---|---|---|---|---|
| Taxol + Rg5 | Taxol | Blank Rg5 | Taxol + Rg5 | Taxol | Blank Rg5 |
| 400 + 2400 | 400 | 2400 | 0.096 | 0.134 | 0.12 |
| 200 + 1200 | 200 | 1200 | 0.115 | 0.15 | 0.161 |
| 100 + 600 | 100 | 600 | 0.132 | 0.166 | 0.178 |
| 50 + 300 | 50 | 300 | 0.135 | 0.272 | 0.231 |
| 25 + 150 | 25 | 150 | 0.242 | 0.454 | 0.321 |
| 12.5 + 75 | 12.5 | 75 | 0.297 | 0.639 | 0.504 |
| 6.25 + 37.5 | 6.25 | 37.5 | 0.388 | 0.756 | 0.702 |
| 3.125 + 18.75 | 3.125 | 18.75 | 0.588 | 0.832 | 0.789 |
| 1.5625 + 9.375 | 1.5625 | 9.375 | 0.85 | 0.85 | 0.802 |

Table 45 and FIG. 45 showed that activity of ginsenoside Rg5 was relatively strong against paclitaxel-resistant human pancreatic cancer cell line (BxPC-3/T). The activity of ginsenoside Rg5 paclitaxel liposome was stronger than that of conventional Taxol injection against paclitaxel-resistant human pancreatic cancer cell line (BxPC-3/T).

2. According to the assay of $IC_{50}$, the $IC_{50}$ of blank Rg5, Taxol and Taxol+Rg5 against human pancreatic cancer cell line (BxPC-3) and paclitaxel-resistant human pancreatic cancer cell line (BxPC-3/T) was tested respectively. The experimental data were shown in Table 46.

TABLE 46

| Cell line | Blank Rg5 | Taxol | Taxol + Rg5 |
|---|---|---|---|
| BxPC-3/T | 91.60 μM | 20.98 μM | 7.850 μM (47.10 μM) |
| BxPC-3 | 90.66 μM | 9.483 μM | 7.850 μM (47.10 μM) |

Table 46 showed that activity of Taxol+Rg5 was enhanced 1.1-1.5 times that of conventional paclitaxel against human pancreatic cancer cell line (BxPC-3), and activity of Taxol+Rg5 was enhanced 2-3 times that of paclitaxel injection against paclitaxel-resistant human pancreatic cancer cell line (BxPC-3/T).

Application Embodiment 6

Cell Experiment In Vitro and Animal Experiment In Vivo for Ginsenosides Rg5 Docetaxel Liposome Against Breast Cancer Cell Line (MCF-7)/Paclitaxel-Resistant Human Breast Cancer Cell Line (MCF-7/T)

1. Pharmacological Efficacy Experimental Assay In Vitro

According to the assay of cell experiment in vitro, survival rates of conventional docetaxel injection (Doc), ginsenoside Rg5 blank liposome (blank Rg5), ginsenoside Rg5 docetaxel liposome (Doc+Rg5, prepared according to embodiment 9) against human breast cancer cell line (MCF-7)/paclitaxel-resistant human breast cancer cell line (MCF-7/T) were tested. 9 Different drug concentrations were set as shown in Table 47 and Table 48 and detailed cell survival rate data and graph were shown in Table 47 and Table 48, FIG. 46 and FIG. 47. FIG. 46 was the cell survival rate graph of Doc, blank Rg5 and Doc+Rg5 against breast cancer cell line (MCF-7); FIG. 47 was the cell survival rate graph of Doc, blank Rg5 and Doc+Rg5 against paclitaxel-resistant human breast cancer cell line (MCF-7/T).

TABLE 47

Cell survival rates of Doc, blank Rg5 and Doc + Rg5 against human breast cancer cell line (MCF-7)

| C (μM) | | | Cell Viability | | |
|---|---|---|---|---|---|
| Doc + Rg5 | Doc | Blank Rg5 | Doc + Rg5 | Doc | Blank Rg5 |
| 1 + 6 | 1 | 6 | 0.101 | 0.107 | 0.751 |
| 0.5 + 3 | 0.5 | 3 | 0.111 | 0.122 | 0.785 |
| 0.25 + 1.5 | 0.25 | 1.5 | 0.178 | 0.238 | 0.807 |
| 0.125 + 0.75 | 0.125 | 0.75 | 0.282 | 0.317 | 0.813 |
| 0.0625 + 0.375 | 0.0625 | 0.375 | 0.463 | 0.521 | 0.821 |
| 0.03125 + 0.1875 | 0.03125 | 0.1875 | 0.584 | 0.636 | 0.846 |
| 0.015625 + 0.09375 | 0.015625 | 0.09375 | 0.671 | 0.758 | 0.853 |
| 0.007813 + 0.046875 | 0.007813 | 0.046875 | 0.801 | 0.832 | 0.879 |
| 0.003906 + 0.023438 | 0.003906 | 0.023438 | 0.859 | 0.866 | 0.8583 |

Table 47 and FIG. 46 showed that the activity of ginsenoside Rg5 blank liposome was relatively weak against breast cancer cell line (MCF-7), and the activity of Doc+Rg5 was slightly stronger than that of conventional Doc injection against breast cancer cell line (MCF-7).

TABLE 48

Cell survival rates of Doc, blank Rg5 and Doc + Rg5 against paclitaxel-resistant human breast cancer cell line (MCF-7/T)

| C (μM) | | | Cell Viability | | |
|---|---|---|---|---|---|
| Doc + Rg5 | Doc | Blank Rg5 | Doc + Rg5 | Doc | Rg5 |
| 400 + 2400 | 400 | 2400 | 0.072 | 0.099 | 0.091 |
| 200 + 1200 | 200 | 1200 | 0.088 | 0.102 | 0.105 |
| 100 + 600 | 100 | 600 | 0.091 | 0.107 | 0.117 |
| 50 + 300 | 50 | 300 | 0.101 | 0.137 | 0.203 |
| 25 + 150 | 25 | 150 | 0.144 | 0.319 | 0.361 |
| 12.5 + 75 | 12.5 | 75 | 0.217 | 0.484 | 0.5256 |
| 6.25 + 37.5 | 6.25 | 37.5 | 0.401 | 0.609 | 0.6553 |
| 3.125 + 18.75 | 3.125 | 18.75 | 0.562 | 0.756 | 0.7979 |
| 1.5625 + 9.375 | 1.5625 | 9.375 | 0.845 | 0.853 | 0.8583 |

Table 48 and FIG. 47 showed that the activity of ginsenoside Rg5 blank liposome was relatively strong against paclitaxel-resistant human breast cancer cell line (MCF-7/T), and the activity of Doc+Rg5 is stronger than that of conventional Doc injection against paclitaxel-resistant human breast cancer cell line (MCF-7/T).

2. According to the assay of $IC_{50}$, the $IC_{50}$ of Doc, blank Rg5 and Doc+Rg5 against human breast cancer cell line (MCF-7) and paclitaxel-resistant human breast cancer cell line (MCF-7/T) was tested. The experimental data were shown in Table 49.

TABLE 49

| Cell line | Blank Rg5 | Doc | Doc + Rg5 |
|---|---|---|---|
| MCF-7/T | 86.24 μM | 12.11 μM | 6.251 μM (37.51 μM) |
| MCF-7 | 11.29 μM | 57.92 nM | 45.44 nM (0.2726 μM) |

Table 49 showed that the activity of Doc+Rg5 was enhanced 1.2-1.5 times that of conventional docetaxel against human breast cancer cell line (MCF-7), and the activity of Doc+Rg5 was enhanced 1.5-2 times that of docetaxel against paclitaxel-resistant human breast cancer cell line (MCF-7/T).

3. Pharmacological Efficacy Experiment In Vivo

27 Subcutaneous tumor-bearing mice were randomly divided into 3 groups (9 in each group), a control group (Control group, 0.9% NaCl), a Doc+Rg5 group and an Abraxane group. Corresponding preparations were injected via tail vein (a dose of 25 mg·kg$^{-1}$). The change of body weights of mice in each group was recorded every 2 days, and the longest diameter and the shortest diameter of tumors were measured with a vernier caliper. The tumor volumes is calculated by the following formula: V=(dmax×dmin$^2$)/2, wherein dmin and dmax are respectively the shortest diameter and the longest diameter (mm) of the tumor; relative tumor volume (RTV) is calculated according to the measurement results, the calculation formula is: RTV=Vt/V0, wherein V0 was the volume measured when the mouse started to be administered and Vt w the tumor volume measured every 2 days.

3.1 Compare antitumor effect (pharmacological efficacy) of the control group, Doc+Rg5 group and Abraxane group against human breast cancer cell line (MCF-7). The detailed experimental data were shown in Table 50 and FIG. 48.

Wherein FIG. 48 is the antitumor graph of the control group, Doc+Rg5 group and Abraxane group against human breast cancer cell line (MCF-7).

TABLE 50

Antitumor effect of the control, Doc + Rg5 and Abraxane group against human breast cancer cell line (MCF-7)

| MCF-7 Time (d) | Relative tumor volume | | | | | |
|---|---|---|---|---|---|---|
| | Control | SD | Taxol + Rg5 | SD | Abraxane | SD |
| 0 | 1 | 0.592 | 1 | 0.247 | 1 | 0.269 |
| 4 | 1.736 | 0.65 | 1.251 | 0.27 | 1.34 | 0.173 |
| 7 | 3.358 | 0.824 | 1.32 | 0.327 | 1.58 | 0.248 |
| 11 | 6.127 | 0.833 | 1.66 | 0.292 | 2.19 | 0.28 |
| 14 | 6.783 | 1.163 | 1.72 | 0.25 | 2.6 | 0.317 |
| 18 | 7.472 | 1.056 | 2.07 | 0.231 | 2.99 | 0.282 |
| 21 | 8.214 | 1.403 | 2.14 | 0.243 | 3.51 | 0.293 |

Table 50 and FIG. 48 showed that the pharmacological efficacy of Doc+Rg5 was slightly stronger than that of Abraxane injection in treating tumor-bearing mice of human breast cancer cell line (MCF-7).

3.2 Compare antitumor effect (pharmacological efficacy) of the control group, Doc+Rg5 group and Abraxane group against Taxol-resistant human breast cancer cell line (MCF-7/T). The detailed experimental data were shown in Table 51 and FIG. 49. FIG. 49 was the antitumor graph of the control group, Doc+Rg5 group and Abraxane group against paclitaxel-resistant human breast cancer cell line (MCF-7/T).

TABLE 51

Antitumor effect of the control group, Doc + Rg5 group and Abraxane group against paclitaxel-resistant human breast cancer cell line (MCF-7/T)

| MCF-7/T Time (d) | Relative tumor volume | | | | | |
|---|---|---|---|---|---|---|
| | Control | SD | Taxol + Rg5 | SD | Abraxane | SD |
| 0 | 1 | 0.592 | 1 | 0.336 | 1 | 0.375 |
| 2 | 2.136 | 0.65 | 1.251 | 0.24 | 1.34 | 0.286 |
| 4 | 3.758 | 0.824 | 1.62 | 0.367 | 2.58 | 0.357 |
| 6 | 5.127 | 0.833 | 2.16 | 0.392 | 3.19 | 0.54 |
| 8 | 7.783 | 1.163 | 2.92 | 0.45 | 4.64 | 0.847 |
| 10 | 10.072 | 1.956 | 2.85 | 0.531 | 5.79 | 1.582 |
| 12 | 15.214 | 1.603 | 3.64 | 0.753 | 6.81 | 1.293 |

Table 51 and FIG. 49 showed that the pharmacological efficacy of Doc+Rg5 had obvious advantages compared to Abraxane injection in treating tumor-bearing mice of Paclitaxel-resistant human breast cancer cell line (MCF-7/T).

Application Embodiment 7

Cell Experiment In Vitro for Ginsenosides Rg5 Cabazitaxel Liposome Against Human Prostate Cancer Cell Line (PC-3)/Paclitaxel-Resistant Human Prostate Cancer Cell Line (PC-3/T)

1. Pharmacological Efficacy Experimental Assay In Vitro

According to the assay of cell experiment in vitro, survival rates of conventional cabazitaxel injection (Cab), ginsenoside Rg5 blank liposome (blank Rg5) and ginsenoside Rg5 cabazitaxel liposome (Cab+Rg5, prepared according to embodiment 20) against human prostate cancer cell line (PC-3)/paclitaxel-resistant human prostate cancer cell line (PC-3/T) were tested respectively. 10 Different drug concentrations were set as shown in Table 44 and Table 45. Detailed survival rate data and graphs were shown in Table 52, 53 and FIG. 50, 51. FIG. 50 was the cell survival rate graph of Cab, blank Rg5 and Cab+Rg5 against human prostate cancer cell line (PC-3). FIG. 51 was the cell survival rate graph of Cab, blank Rg5 and Cab+Rg5 against paclitaxel-resistant human prostate cancer cell line (PC-3/T).

TABLE 52

Cell survival rates of Cab, blank Rg5 and Cab + Rg5 against human prostate cancer cell line (PC-3)

| C (µM) | | | Cell Viability | | |
|---|---|---|---|---|---|
| Cab + Rg5 | Cab | Blank Rg5 | Cab + Rg5 | Cab | Blank Rg5 |
| 15 + 90 | 15 | 90 | 0.063 | 0.084 | 0.133 |
| 7.5 + 45 | 7.5 | 45 | 0.072 | 0.091 | 0.284 |
| 3.75 + 22.5 | 3.75 | 22.5 | 0.087 | 0.094 | 0.55 |
| 1.875 + 11.25 | 1.875 | 11.25 | 0.091 | 0.101 | 0.714 |
| 0.9375 + 5.625 | 0.9375 | 5.625 | 0.101 | 0.113 | 0.803 |
| 0.46875 + 2.8125 | 0.46875 | 2.8125 | 0.123 | 0.137 | 0.826 |
| 0.234375 + 1.40625 | 0.234375 | 1.40625 | 0.151 | 0.187 | 0.838 |
| 0.117188 + 0.703125 | 0.117188 | 0.703125 | 0.172 | 0.212 | 0.843 |
| 0.058594 + 0.351563 | 0.058594 | 0.351563 | 0.267 | 0.313 | 0.844 |
| 0.029297 + 0.175781 | 0.029297 | 0.175781 | 0.493 | 0.569 | 0.845 |

Table 52 and FIG. 50 showed that the activity of ginsenoside Rg5 blank liposome was relatively weak against human prostate cancer cell line (PC-3) in low doses, but strong in high doses. The activity of Cab+Rg5 was slightly stronger than that of conventional cabazitaxel injection against human prostate cancer cell line (PC-3).

TABLE 53

Cell survival rates of Cab, blank Rg5 and Cab + Rg5 against paclitaxel-resistant human prostate cancer cell line (PC-3/T)

| C (µM) | | | Cell Viability | | |
|---|---|---|---|---|---|
| Cab + Rg5 | Cab | Rg5 | Cab + Rg5 | Cab | Rg5 |
| 50 + 300 | 50 | 300 | 0.088 | 0.134 | 0.107 |
| 25 + 150 | 25 | 150 | 0.096 | 0.143 | 0.128 |
| 12.5 + 75 | 12.5 | 75 | 0.103 | 0.213 | 0.235 |
| 6.25 + 37.5 | 6.25 | 37.5 | 0.121 | 0.307 | 0.55 |
| 3.125 + 18.75 | 3.125 | 18.75 | 0.141 | 0.503 | 0.749 |
| 1.5625 + 9.375 | 1.5625 | 9.375 | 0.153 | 0.653 | 0.853 |
| 0.78125 + 4.6875 | 0.78125 | 4.6875 | 0.161 | 0.768 | 0.865 |
| 0.390625 + 2.34375 | 0.390625 | 2.34375 | 0.202 | 0.852 | 0.878 |
| 0.195313 + 1.171875 | 0.195313 | 1.171875 | 0.307 | 0.881 | 0.883 |
| 0.097656 + 0.585938 | 0.097656 | 0.585938 | 0.623 | 0.887 | 0.884 |

Table 53 and FIG. 51 showed that activity of ginsenoside Rg5 blank liposome was relatively weak against paclitaxel-resistant human prostate cancer cell line (PC-3/T) in low doses, but strong in high doses. The activity of Cab+Rg5 was slightly stronger than that of conventional cabazitaxel injection against paclitaxel-resistant human prostate cancer cell line (PC-3/T).

2. According to the assay of $IC_{50}$, the $IC_{50}$ of Cab, blank Rg5 and Taxol+Rg5 against human prostate cancer cell line (PC-3) and paclitaxel-resistant human prostate cancer cell line (PC-3/T) was tested respectively. The experimental data were shown in Table 54.

TABLE 54

| Cell line | Blank Rg5 | Cab | Cab + Rg5 |
|---|---|---|---|
| PC-3/T | 29.01 μM | 2.809 μM | 0.2618 μM (1.571 μM) |
| PC-3 | 12.70 μM | 72.85 nM | 58.96 nM (0.3538 μM) |

Table 54 showed that the activity of Cab+Rg5 was enhanced 1.1-1.5 times that of conventional cabazitaxel injection against human prostate cancer cell line (PC-3), and the activity of Cab+Rg5 was enhanced 10-20 times that of conventional cabazitaxel injection against paclitaxel-resistant human prostate cancer cell line (PC-3/T).

Application Embodiment 8

Cell Experiment In Vitro and Animal Experiment In Vivo for Ginsenosides Rg5 Fluorouracil Liposome Against Fluorouracil-Resistant Human Liver Cancer Cell Line (Bel/FU)

1. Pharmacological Efficacy Experimental Assay In Vitro

According to the assay of cell experiment in vitro, cell survival rates and inhibition rates of ginsenoside Rg5 blank liposome (blank Rg5), conventional fluorouracil liposome (FU) and ginsenoside Rg5 fluorouracil liposome (FU+Rg5, prepared according to embodiment 18) against fluorouracil-resistant human liver cancer cell line (Bel/FU) were tested. 10 Different drug concentrations were set as shown in Table 55 and detailed cell survival rate data and cell inhibition data were shown in Table 55 and FIG. 52. FIG. 52 was the cell survival rate graph of FU+Rg5, blank Rg5 and FU against fluorouracil-resistant human liver cancer cell line (Bel/FU).

Table 55, Table 56 and FIG. 52 showed that the activity of ginsenoside Rg5 blank liposome was relatively weak against fluorouracil-resistant human liver cancer cell line (Bel/FU), and the activity of FU+Rg5 had obvious advantages compared to that of conventional fluorouracil liposome against fluorouracil-resistant human liver cancer cell line (Bel/FU). The activity of FU+Rg5 was enhanced 3 times that of conventional fluorouracil liposome against fluorouracil-resistant human liver cancer cell line (Bel/FU).

3. Pharmacological efficacy experiment in vivo: Diameters of tumors transplanted subcutaneously in nude mice were measured with a vernier caliper. When tumors grew to an average volume of about 100 mm$^3$, the animals were divided into groups randomly. The dose for conventional fluorouracil liposome (FU) single-use group was 5 mg/kg, and the mice were injected once per week intravenously for three weeks. The dose for ginsenoside Rg5 blank liposome (blank Rg5) single-use group was 150 mg/kg, and the mice were injected once per week intravenously for three weeks. The dose of ginsenoside Rg5 fluorouracil liposome (FU+Rg5) group was 5+150 mg/kg, also injected once per week intravenously for three weeks. The solvent control group was injected with equivalent amount of normal saline. Throughout this experiment, transplanted tumor diameters were measured every 2 days. The formula for calculating tumor volume (TV) is: TV=½×a×b$^2$, wherein "a" and "b" represent length and width respectively. Relative tumor volume (RTV) is calculated according to the measurement results, the calculation formula is: RTV=Vt/V0, wherein V0

TABLE 55

Cell survival rates and inhibition rates of FU + Rg5, blank Rg5 and FU against fluorouracil-resistant human liver cancer cell line (Bel/FU)

FU
Fluorouracil-resistant human liver cancer cell line (Bel/FU)

| | | Cell survival rate | | | Cell inhibition rate | | |
|---|---|---|---|---|---|---|---|
| C | LogC | FU + Rg5 | Blank Rg5 | FU | FU + RG5 | Blank Rg5 | FU |
| 100 | 2 | 0.002 | 0.90091 | 0.009 | 0.998 | 0.09909 | 0.991 |
| 50 | 1.69897 | 0.0092 | 0.91284 | 0.0708 | 0.9908 | 0.08716 | 0.9292 |
| 25 | 1.39794 | 0.03 | 0.9395 | 0.217 | 0.97 | 0.0605 | 0.783 |
| 12.5 | 1.09691 | 0.1026 | 0.9193 | 0.327 | 0.8974 | 0.0807 | 0.673 |
| 6.25 | 0.79588 | 0.241 | 0.9092 | 0.458 | 0.759 | 0.0908 | 0.542 |
| 3.125 | 0.49485 | 0.397 | 0.9387 | 0.652 | 0.603 | 0.0613 | 0.348 |
| 1.5625 | 0.19382 | 0.5198 | 0.9179 | 0.74673 | 0.4802 | 0.0821 | 0.25327 |
| 0.78125 | −0.10721 | 0.679 | 0.9061 | 0.7981 | 0.321 | 0.0939 | 0.2019 |
| 0.39063 | −0.40824 | 0.75866 | 0.9273 | 0.8684 | 0.24134 | 0.0727 | 0.1316 |
| 0.19531 | −0.70927 | 0.8596 | 0.9193 | 0.899 | 0.1404 | 0.0807 | 0.101 |
| 0.09766 | −1.0103 | 0.9093 | 0.9093 | 0.9096 | 0.0907 | 0.0907 | 0.0904 |

2. According to the assay of IC$_{50}$, the IC$_{50}$ of FU+Rg5, blank Rg5 and FU against Fluorouracil-resistant human liver cancer cell line (Bel/FU) was tested respectively. The experimental data were shown in Table 56.

TABLE 56

| Cell line | Blank Rg5 | FU | FU + Rg5 |
|---|---|---|---|
| Bel/FU | 114.3 μM | 32.49 μM | 11.89 μM (2.017 μM) | is the tumor volume measured when the mice were divided into groups (i.e. d0) and Vt is the tumor volume measured each time.

Compare antitumor effect (pharmacological efficacy) of blank Rg5, FU and FU+Rg5 against fluorouracil-resistant human liver cancer cell line (Bel/FU). The detailed experimental data were shown in Table 57 and FIG. 53. Wherein FIG. 53 was the antitumor graph of blank Rg5, FU and FU+Rg5 against fluorouracil-resistant human liver cancer cell line (Bel/FU).

TABLE 57

Antitumor effects of blank Rg5, FU + Rg5 and FU against fluorouracil-resistant human liver cancer cell line (Bel/FU)

| Bel-FU Time/d | Blank Rg5 | SD | FU | SD | FU + Rg5 | SD |
|---|---|---|---|---|---|---|
| 0 | 1 | 0.5212 | 1 | 0.5212 | 1 | 0.512 |
| 2 | 2.3 | 0.5215 | 1.9 | 0.522 | 1.4 | 0.513 |
| 4 | 2.6 | 0.5321 | 2.1 | 0.529 | 1.3 | 0.512 |
| 6 | 4.1 | 0.542 | 2.3 | 0.534 | 1.6 | 0.515 |
| 8 | 6.8 | 0.945 | 4.1 | 0.639 | 1.9 | 0.516 |
| 10 | 8.9 | 0.93 | 4.3 | 0.843 | 2.1 | 0.518 |
| 12 | 14.3 | 0.86 | 5.8 | 0.746 | 2.5 | 0.514 |
| 14 | 16.6 | 0.967 | 6.2 | 0.9237 | 3.3 | 0.519 |

Table 57 and FIG. 53 showed that the pharmacological efficacy of FU+Rg5 had obvious advantages compared to that of conventional fluorouracil in treating tumor-bearing mice of fluorouracil-resistant human liver cancer cell line (Bel/FU).

Application Embodiment 9

Cell Experiment In Vitro and Animal Experiment In Vivo for Ginsenosides Rg5 Cisplatin Liposome Against Cisplatin-Resistant Human Gastric Cancer Cell Line (SGC-7901/DDP)

1. Pharmacological Efficacy Experimental Assay In Vitro

According to the assay of cell experiment in vitro, cell survival rates and inhibition rates of ginsenoside Rg5 blank liposome (blank Rg5), conventional cisplatin liposome (DDP) and ginsenoside Rg5 cisplatin liposome (DDP+Rg5, prepared according to embodiment 17) against cisplatin-resistant human gastric cancer cell line (SGC-7901/DDP) were tested. 11 Different drug concentrations were set as shown in Table 58 and detailed cell survival rate data and cell inhibition rate data were shown in Table 58 and FIG. 54. FIG. 54 was the cell survival rate graph of blank Rg5, DDP and DDP+Rg5 against cisplatin-resistant human gastric cancer cell line (SGC-7901/DDP).

TABLE 58

Cell survival rates and cell inhibition rates of blank Rg5, DDP and DDP + Rg5 against cisplatin-resistant human gastric cancer cell line (SGC-7901/DDP)

DDP Cisplatin-resistant human gastric cancer cell line (SGC-7901/DDP)

| | | Cell survival rate | | | Cell inhibition rate | | |
|---|---|---|---|---|---|---|---|
| LogC | C | DDP + Rg5 | Rg5 | DDP | DDP + Rg5 | Rg5 | DDP |
| 2 | 100 | 0.002 | 1.001 | 0.008 | 0.998 | −0.001 | 0.992 |
| 1.69897 | 50 | 0.006 | 1.009 | 0.012 | 0.994 | −0.009 | 0.988 |
| 1.39794 | 25 | 0.004 | 0.993 | 0.247 | 0.996 | 0.007 | 0.753 |
| 1.09691 | 12.5 | 0.019 | 0.991 | 0.429 | 0.981 | 0.009 | 0.571 |
| 0.79588 | 6.25 | 0.157 | 0.997 | 0.621 | 0.843 | 0.003 | 0.379 |
| 0.49485 | 3.125 | 0.328 | 0.982 | 0.773 | 0.672 | 0.018 | 0.227 |
| 0.19382 | 1.5625 | 0.589 | 0.973 | 0.874 | 0.411 | 0.027 | 0.126 |
| −0.10721 | 0.78125 | 0.793 | 0.965 | 0.926 | 0.207 | 0.035 | 0.074 |
| −0.40823 | 0.39063 | 0.854 | 0.994 | 0.987 | 0.146 | 0.006 | 0.013 |
| −0.70928 | 0.19531 | 0.925 | 0.999 | 0.994 | 0.075 | 0.001 | 0.006 |
| −1.01028 | 0.09766 | 0.991 | 1.003 | 1.002 | 0.009 | −0.003 | −0.002 |

2. According to the assay of $IC_{50}$, the $IC_{50}$ of blank Rg5, DDP and DDP+Rg5 against cisplatin-resistant human gastric cancer cell line (SGC-7901/DDP) was tested. The experimental data were shown in Table 59.

TABLE 59

| Cell line | Blank Rg5 | DDP | DDP + Rg5 |
|---|---|---|---|
| SGC-7901/DDP | 204.7 μM | 27.02 μM | 5.839 μM (2.285 μM) |

Table 58, Table 59 and FIG. 54 showed that the pharmacological activity of ginsenoside Rg5 was relatively weak against cisplatin-resistant human gastric cancer cell line (SGC-7901/DDP), and the activity of DDP+Rg5 had obvious advantages compared to that of conventional cisplatin liposome against cisplatin-resistant human gastric cancer cell line (SGC-7901/DDP). The activity of DDP+Rg5 was enhanced 5 times that of conventional cisplatin liposome against cisplatin-resistant human gastric cancer cell line (SGC-7901/DDP).

3. Pharmacological efficacy experiment in vivo: Diameters of tumors transplanted subcutaneously in nude mice were measured with a vernier caliper. When tumors grew to an average volume of about 100 mm$^3$, the animals were divided into groups randomly. A dose for conventional cisplatin liposome (DDP) single-use group was 6 mg/kg, and the mice were injected once per week intravenously for three weeks. A dose for ginsenoside Rg5 blank liposome (blank Rg5) single-use group was 150 mg/kg, and the mice were injected once per week intravenously for three weeks. A dose of ginsenoside Rg5 cisplatin liposome (DDP+Rg5) group was 6+150 mg/kg, the mice were also injected once per week intravenously for three weeks. The solvent control group was injected with equivalent amount of normal saline. Throughout this experiment, tumor diameters were measured every 2 days. The formula for calculating tumor volume (TV) is: TV=½×a×b$^2$, wherein "a" and "b" represent length and width respectively. Relative tumor volume (RTV) is calculated according to the measurement results, the calculation formula is: RTV=Vt/V0, wherein V0 was the tumor volume measured when the mice were divided into groups and Vt was the tumor volume measured each time.

Compare antitumor effect (pharmacological efficacy) of blank Rg5, DDP and DDP+Rg5 against cisplatin-resistant human gastric cancer cell line (SGC-7901/DDP). The detailed experimental data were shown in Table 60 and FIG. 55. FIG. 55 was the antitumor graph of blank Rg5, DDP and DDP+Rg5 against cisplatin-resistant human gastric cancer cell line (SGC-7901/DDP).

shown in Table 61 and detailed cell survival rate data and cell inhibition rate data were shown in Table 61 and FIG. 56. FIG. 56 was the cell survival rate graph of blank Rg5, V and V+Rg5 against vincristine-resistant human colon cancer cell line (HCT-8/V).

TABLE 61

Cell survival rates and cell inhibition rates of blank Rg5, V and V + Rg5 against vincristine-resistant human colon cancer cell line (HCT-8/V)

V
Vincristine-resistant human colon cancer cell line (HCT-8/V)

| | | Cell survival rate | | | Cell inhibition rate | | |
|---|---|---|---|---|---|---|---|
| C | LogC | V + Rg5 | Blank Rg5 | V | V + Rg5 | Blank Rg5 | V |
| 32 | 1.50515 | 0.009 | 1.002 | 0.021 | 0.991 | −0.002 | 0.979 |
| 16 | 1.20412 | 0.012 | 1.01 | 0.037 | 0.988 | −0.01 | 0.963 |
| 8 | 0.90309 | 0.037 | 0.983 | 0.094 | 0.963 | 0.017 | 0.906 |
| 4 | 0.60206 | 0.127 | 0.989 | 0.236 | 0.873 | 0.011 | 0.764 |
| 2 | 0.30103 | 0.239 | 0.996 | 0.45283 | 0.761 | 0.004 | 0.54717 |
| 1 | 0 | 0.427 | 0.992 | 0.6135 | 0.573 | 0.008 | 0.3865 |
| 0.5 | −0.30103 | 0.5672 | 0.969 | 0.734 | 0.4328 | 0.031 | 0.266 |
| 0.25 | −0.60206 | 0.763 | 0.984 | 0.843 | 0.237 | 0.016 | 0.157 |
| 0.125 | −0.90309 | 0.864 | 1.007 | 0.946 | 0.136 | −0.007 | 0.054 |
| 0.0625 | −1.20412 | 0.951 | 0.979 | 0.986 | 0.049 | 0.021 | 0.014 |
| 0.03125 | −1.50515 | 0.984 | 1.005 | 0.997 | 0.016 | −0.005 | 0.003 |

TABLE 60

Antitumor effects of blank Rg5, DDP and DDP + Rg5 against cisplatin-resistant human gastric cancer cell line (SGC-7901/DDP)

Relative tumor volume

| SGC-7901/DDP Time/d | Rg5 | SD | DDP | SD | DDP + Rg5 | SD |
|---|---|---|---|---|---|---|
| 0 | 1 | 0.212 | 1 | 0.212 | 1 | 0.212 |
| 2 | 1.4 | 0.215 | 1.3 | 0.22 | 1.2 | 0.213 |
| 4 | 1.8 | 0.321 | 1.6 | 0.29 | 1.35 | 0.212 |
| 6 | 2.1 | 0.42 | 1.9 | 0.34 | 1.5 | 0.215 |
| 8 | 3.2 | 0.45 | 2.4 | 0.39 | 1.6 | 0.216 |
| 10 | 4.9 | 0.63 | 3.6 | 0.43 | 2.3 | 0.218 |
| 12 | 6.3 | 0.86 | 4.3 | 0.46 | 2.5 | 0.314 |
| 14 | 9.1 | 0.967 | 5.5 | 0.59237 | 3.2 | 0.419 |

Table 60 and FIG. 55 showed that the pharmacological efficacy of DDP+Rg5 had obvious advantages compared to that of conventional cisplatin in treating tumor-bearing mice of cisplatin-resistant human gastric cancer cell line (SGC-7901/DDP).

Application Embodiment 10

Cell Experiment In Vitro and Animal Experiment In Vivo for Ginsenosides Rg5 Vincristine Sulfate Liposome Against Vincristine-Resistant Human Colon Cancer Cell Line (HCT-8/V)

1. Pharmacological Efficacy Experimental Assay In Vitro

According to the assay of cell experiment in vitro, cell survival rates and inhibition rates of ginsenoside Rg5 blank liposome (blank Rg5), conventional vincristine liposome (V) and ginsenoside Rg5 vincristine sulphate liposome (V+Rg5, prepared according to embodiment 15) against vincristine-resistant human colon cancer cell line (HCT-8/V) were tested. 11 Different drug concentrations were set as 2. According to the assay of $IC_{50}$, the $IC_{50}$ values of blank Rg5, V and V+Rg5 against vincristine-resistant human colon cancer cell line (HCT-8/V) were tested. The experimental data were shown in Table 62.

TABLE 62

| Cell line | Blank Rg5 | V | V + Rg5 |
|---|---|---|---|
| HCT-8/V | 65.94 μM | 1.673 μM | 0.8444 μM (0.9082 μM) |

Table 61, Table 62 and FIG. 56 showed that the activity of ginsenoside Rg5 blank liposome was relatively weak against vincristine-resistant human colon cancer cell line (HCT-8/V), and the activity of V+Rg5 had obvious advantages compared to that of conventional vincristine against vincristine-resistant human colon cancer cell line (HCT-8/V). The activity of V+Rg5 was enhanced 2 times that of conventional vincristine liposome against vincristine-resistant human colon cancer cell line (HCT-8/V).

3. Pharmacological Efficacy Experiment In Vivo

Diameters of tumors transplanted subcutaneously in nude mice were measured with a vernier caliper. When tumors grew to an average volume of about 100 mm³, the animals were divided into groups randomly. A dose of conventional vincristine liposome (V) single-use group was 0.5 mg/kg, and the mice were injected once per week intravenously for three weeks. A dose of ginsenoside Rg5 blank liposome (blank Rg5) single-use group was 150 mg/kg, and the mice were injected once per week intravenously for three weeks. A dose of ginsenoside Rg5 vincristine liposome (V+Rg5) was 0.5+150 mg/kg, the mice were also injected once per week intravenously for three weeks. The solvent control group was injected with equivalent amount of normal saline. Throughout this experiment, tumor diameters were measured every 2 days. The formula for calculating tumor volume (TV) is: TV=½×a×b², wherein "a" and "b" represent length and width respectively. Relative tumor volume (RTV) is calculated according to the measurement results, the calculation formula is: RTV=Vt/V0, wherein V0 is the tumor volume measured when the mice were divided into groups (i.e. d0) and Vt is the tumor volume measured each time.

Compare antitumor effects (pharmacological efficacy) of blank Rg5, V and V+Rg5 against vincristine-resistant human colon cancer cell line (HCT-8/V). The detailed experimental data were shown in Table 63 and FIG. 57. FIG. 57 was the antitumor graph of blank Rg5, V and V+Rg5 against vincristine-resistant human colon cancer cell line (HCT-8/V).

TABLE 63

Antitumor effects of blank Rg5, V and V + Rg5 against vincristine-resistant human colon cancer cell line (HCT-8/V)

| HCT-8/V Time/d | Blank Rg5 | SD | V | SD | V + Rg5 | SD |
|---|---|---|---|---|---|---|
| 0 | 1 | 0.212 | 1 | 0.212 | 1 | 0.212 |
| 2 | 1.4 | 0.215 | 1.3 | 0.22 | 1.1 | 0.213 |
| 4 | 1.8 | 0.321 | 1.6 | 0.29 | 1.3 | 0.32 |
| 6 | 2.7 | 0.42 | 1.9 | 0.34 | 1.6 | 0.315 |
| 8 | 4.3 | 0.45 | 3.5 | 0.39 | 2.3 | 0.516 |
| 10 | 7.9 | 0.63 | 5.2 | 0.743 | 2.5 | 0.618 |
| 12 | 9.6 | 0.86 | 6.8 | 0.6 | 3.6 | 0.714 |
| 14 | 13.1 | 0.967 | 9.7 | 0.9237 | 4.3 | 0.819 |

Table 63 and FIG. 57 showed that the pharmacological efficacy of V+Rg5 had obvious advantages compared to that of conventional vincristine liposome in treating tumor-bearing mice of vincristine-resistant human colon cancer cell line (HCT-8/V).

Application Embodiment 11

Cell Experiment In Vitro and Animal Experiment In Vivo (Oral Administration) for Ginsenosides Rg5 Paclitaxel Liposome Against Gastric Cancer Cell Line (SGC-7901)/Paclitaxel-Resistant Human Gastric Cancer Cell Line (SGC-7901/T)

1. Pharmacological Efficacy Experiment In Vitro

According to the assay of cell experiment in vitro, cell survival rates of ginsenoside Rg5 blank liposome (blank Rg5), conventional paclitaxel injection (Taxol) and ginsenoside Rg5 paclitaxel liposome (Taxol+Rg5) against human gastric cancer (SGC-7901) cell line and paclitaxel-resistant human gastric cancer cell line (SGC-7901/T) were tested respectively. 10 Different drug concentrations were set as shown in Table 64 and 66, and detailed cell survival rate data and graph were shown in Table 64 and Table 66, FIG. 58 and FIG. 59.

TABLE 64

Cell survival rates of blank Rg5, Taxol, and Rg5 + Taxol against human gastric cancer cell line (SGC-7901)

Human gastric cancer cell line (SGC-7901)

| | | Cell survival rate | | | | | |
|---|---|---|---|---|---|---|---|
| C | LOGC (ug/ml) | Rg5 | SD | Taxol | SD | Rg5 + Taxol | SD |
| 50 | 1.69897 | 1.011 | 0.016 | 0.006 | 0.017 | 0.006 | 0.002 |
| 25 | 1.39794 | 0.979 | 0.021 | 0.004 | 0.019 | 0.004 | 0.004 |
| 12.5 | 1.09691 | 0.978 | 0.037 | 0.019 | 0.019 | 0.019 | 0.017 |
| 6.25 | 0.79588 | 0.971 | 0.042 | 0.157 | 0.016 | 0.077 | 0.019 |
| 3.125 | 0.49485 | 0.977 | 0.024 | 0.308 | 0.021 | 0.168 | 0.029 |
| 1.5625 | 0.19382 | 0.996 | 0.027 | 0.419 | 0.017 | 0.279 | 0.016 |
| 0.78125 | −0.10721 | 0.983 | 0.047 | 0.638 | 0.022 | 0.428 | 0.021 |
| 0.39063 | −0.40823 | 0.985 | 0.029 | 0.864 | 0.034 | 0.664 | 0.037 |
| 0.19531 | −0.70928 | 0.984 | 0.029 | 0.925 | 0.047 | 0.825 | 0.043 |
| 0.09766 | −1.01028 | 0.979 | 0.036 | 0.991 | 0.049 | 0.991 | 0.035 |

2. According to the assay of $IC_{50}$, the $IC_{50}$ of blank Rg5, Taxol and Rg5+Taxol against human gastric cancer cell line (SGC-7901) was tested. The experimental data were shown in Table 65.

TABLE 65

| | Blank Rg5 | Taxol | Rg5 + Taxol |
|---|---|---|---|
| $IC_{50}$ (µM) | 77.4 | 1.51 | 0.523 (3.50) |

Table 64, Table 65 and FIG. 58 showed that activity of ginsenoside Rg5 blank liposome was relatively weak against human gastric cancer cell line (SGC-7901), and the activity of Rg5+Taxol was stronger than that of conventional paclitaxel injection against human gastric cancer cell line (SGC-7901).

TABLE 66

Cell survival rates of blank Rg5, Taxol, and Rg5 + Taxol against paclitaxel-resistant human gastric cancer cell line (SGC-7901/T)

TAX paclitaxel-resistant human gastric cancer cell line (SGC-7901/T)

| | | Cell survival rate | | | | | |
|---|---|---|---|---|---|---|---|
| C | LOGC (ug/ml) | Rg5 | SD | Taxol | SD | Rg5 + Taxol | SD |
| 100 | 2 | 1.011 | 0.016 | 0.015 | 0.017 | 0.002 | 0.002 |
| 50 | 1.69897 | 0.979 | 0.021 | 0.028 | 0.019 | 0.006 | 0.004 |
| 25 | 1.39794 | 0.983 | 0.007 | 0.217 | 0.019 | 0.004 | 0.017 |
| 12.5 | 1.09691 | 0.971 | 0.012 | 0.339 | 0.016 | 0.019 | 0.019 |
| 6.25 | 0.79588 | 0.987 | 0.024 | 0.531 | 0.021 | 0.157 | 0.009 |
| 3.125 | 0.49485 | 0.993 | 0.027 | 0.713 | 0.017 | 0.328 | 0.016 |
| 1.5625 | 0.19382 | 0.983 | 0.017 | 0.844 | 0.022 | 0.499 | 0.021 |

TABLE 66-continued

Cell survival rates of blank Rg5, Taxol, and Rg5 + Taxol against paclitaxel-resistant human gastric cancer cell line (SGC-7901/T)

| | | TAX paclitaxel-resistant human gastric cancer cell line (SGC-7901/T) | | | | | |
|---|---|---|---|---|---|---|---|
| | / | / | | Cell survival rate | | | |
| C | LOGC (ug/ml) | Rg5 | SD | Taxol | SD | Rg5 + Taxol | SD |
| 0.78175 | −0.10771 | 0.985 | 0.079 | 0.894 | 0.034 | 0.738 | 0.037 |
| 0.39063 | −0.40823 | 0.994 | 0.029 | 0.942 | 0.017 | 0.864 | 0.023 |
| 0.19531 | −0.70928 | 0.979 | 0.016 | 0.984 | 0.019 | 0.925 | 0.025 |
| 0.09766 | −1.01028 | 0.99 | 0.035 | 1.012 | 0.009 | 0.991 | 0.038 |

3. According to the assay of $IC_{50}$, the $IC_{50}$ of blank Rg5, Taxol and Rg5+Taxol against paclitaxel-resistant human gastric cancer cell line (SGC-7901/T) was tested. The experimental data were shown in Table 67.

TABLE 67

| / | Blank Rg5 | Taxol | Rg5 + Taxol |
|---|---|---|---|
| $IC_{50}$ (µM) | 127.4 | 9.735 | 2.0 (15.65) |

Table 66, Table 67 and FIG. 59 showed that the activity of ginsenoside Rg5 blank liposome was relatively weak against paclitaxel-resistant human gastric cancer cell line (SGC-7901/T), and the activity of Rg5+Taxol had obvious advantages compared to that of conventional paclitaxel injection against paclitaxel-resistant human gastric cancer cell line (SGC-7901/T).

4. Experiment In Vivo

27 Subcutaneous tumor-bearing mice were randomly divided into 3 groups (9 in each group), a control group (Control group, 0.9% NaCl), a Taxol+Rg5 group and an Abraxane group. Corresponding preparation was administered orally (a dose of 50 mg·kg-1). The changes of body weights of mice were recorded every 2 days, and the longest diameters and the shortest diameters of tumors were measured with a vernier caliper. The tumor volumes were calculated by the following formula: V=(dmax×dmin$^2$)/2, wherein dmin and dmax were respectively the shortest diameter and the longest diameter (mm) of the tumor; relative tumor volume (RTV) is calculated according to the measurement results, the calculation formula is: RTV=Vt/V0, wherein V0 was the tumor volume measure when the mice started to be administered and Vt was the tumor volume measured every 2 days.

Compare antitumor effects (pharmacological efficacy) of Abraxane and Taxol+Rg5 against human gastric cancer cell line (SGC-7901) and paclitaxel-resistant human gastric cancer cell line (SGC-7901/T). The detailed experimental data were shown in Table 68 and Table 69, FIG. 60 and FIG. 61. FIG. 60 and FIG. 61 were the antitumor graphs of the control group, Abraxane group and Taxol+Rg5 group against human gastric cancer cell line (SGC-7901) and paclitaxel-resistant human gastric cancer cell line (SGC-7901/T).

TABLE 68

Antitumor effects of the control group, Abraxane group and Taxol + Rg5 group against human gastric cancer cell line (SGC-7901)

| | Relative tumor volume | | | | | |
|---|---|---|---|---|---|---|
| SGC-7901 Time (d) | Control | SD | Taxol + Rg5 | SD | Abraxane | SD |
| 0 | 1 | 0.592 | 1 | 0.346 | 1 | 0.375 |
| 2 | 2.136 | 0.465 | 1.35 | 0.454 | 1.64 | 0.286 |
| 4 | 3.758 | 0.624 | 1.51 | 0.457 | 2.08 | 0.357 |
| 6 | 4.127 | 0.703 | 2.21 | 0.392 | 2.59 | 0.454 |
| 8 | 5.783 | 1.049 | 2.32 | 0.345 | 3.04 | 0.647 |
| 10 | 7.072 | 1.856 | 2.87 | 0.931 | 3.79 | 1.082 |
| 12 | 10.814 | 1.583 | 3.04 | 0.853 | 3.91 | 0.93 |
| 14 | 14.157 | 2.289 | 3.32 | 1.048 | 4.58 | 1.185 |

Table 68 and FIG. 60 showed that the pharmacological efficacy of Taxol+Rg5 had obvious advantages compared to that of conventional paclitaxel injection in treating tumor-bearing mice of human gastric cancer cell line (SGC-7901).

TABLE 69

Antitumor effects of the control group, Abraxane group and Rg5 + Taxol group against paclitaxel-resistant human gastric cancer cell line (SGC-7901/T)

| | Relative tumor volume | | | | | |
|---|---|---|---|---|---|---|
| SGC-7901/T Time (d) | Control | SD | Taxol + Rg5 | SD | Abraxane | SD |
| 0 | 1 | 0.392 | 1 | 0.346 | 1 | 0.375 |
| 2 | 1.936 | 0.375 | 1.235 | 0.254 | 1.64 | 0.386 |
| 4 | 2.758 | 0.424 | 1.63 | 0.353 | 2.08 | 0.457 |
| 6 | 4.527 | 0.603 | 2.01 | 0.392 | 2.79 | 0.354 |
| 8 | 5.383 | 1.049 | 2.32 | 0.345 | 3.54 | 0.543 |
| 10 | 6.772 | 0.856 | 2.59 | 0.631 | 4.09 | 0.812 |
| 12 | 8.914 | 1.083 | 3.27 | 0.753 | 5.21 | 0.743 |
| 14 | 10.157 | 1.489 | 3.12 | 0.748 | 6.48 | 1.085 |

Table 69 and FIG. 61 showed that the pharmacological efficacy of Taxol+Rg5 had obvious advantages compared to that of conventional paclitaxel injection in treating tumor-bearing mice of paclitaxel-resistant human gastric cancer cell line (SGC-7901/T).

Effect Embodiment

1. Ginsenoside Rg5 Paclitaxel Liposome

Egg lecithin 30 mg, ginsenoside Rg5, paclitaxel 3 mg and soybean oil 15 mg were added into 2 mL acetonitrile and stirred to form a clear solution at room temperature. The organic solvent was removed by a rotary evaporation in a thermostatic water bath at 40 to 50° C. to form a film, and 20 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials. The data of the dosage of ginsenoside Rg5, the appearance, the encapsulated efficiency of paclitaxel, the average particle size and the stability of the prepared ginsenoside Rg5 paclitaxel liposome are shown in the table below.

2 mL acetonitrile and stirred to form a clear solution at room temperature. The organic solvent was removed by a rotary evaporation in a thermostatic water bath at 40 to 50° C. to form a film, and 20 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg5 paclitaxel liposome. Then the aqueous solution was split charging into vials. The data of the dosage of the ginsenoside Rg5, the appearance, the encapsulated effi-

| The dosage of Rg5 | Appearance | Encapsulated efficiency (%) | Average particle size (nm) | Stability |
|---|---|---|---|---|
| 3 mg | Bright | ≥95% | 68.0 | 1) placing for 7 days, stable, encapsulated efficiency ≥90%; 2) placing for 15 days, stable, encapsulated efficiency ≥90%; 3) placing for 30 days, little precipitation, encapsulated efficiency ≤80%. |
| 6 mg | Bright | ≥95% | 90.78 | 1) placing for 7 days, stable, encapsulated efficiency ≥90%; 2) placing for 15 days, stable, encapsulated efficiency ≥90%; 3) placing for 30 days, little precipitation, encapsulated efficiency ≤80%. |
| 9 mg | Relatively bright | ≥98% | 91.96 | 1) placing for 7 days, stable, encapsulated efficiency ≥95%; 2) placing for 15 days, stable, encapsulation efficiency ≥95%; 3) placing for 30 days, little precipitation, encapsulated efficiency ≤80%. |
| 12 mg | Relatively bright | ≥98% | 102.6 | 1) placing for 7 days, stable, encapsulated efficiency ≥95%; 2) placing for 15 days, stable, encapsulated efficiency ≥95%; 3) placing for 30 days, stable, encapsulated efficiency ≥90%. |
| 15 mg | Bright | ≥95% | 103.7 | 1) placing for 7 days, stable, encapsulated efficiency ≥90%; 2) placing for 15 days, stable, encapsulated efficiency ≥90%; 3) placing for 30 days, little precipitation, encapsulated efficiency was ≤80%. |
| 18 mg | Bright | ≥95% | 115.6 | 1) placing for 7 days, stable, encapsulated efficiency ≥90%; 2) placing for 15 days, little precipitation, encapsulated efficiency ≤80%. |
| 21 mg | Bright | ≥90% | 135.7 | 1) placing for 7 days, stable, encapsulated efficiency ≥90%; 2) placing for 15 days, little precipitation, encapsulated efficiency ≤80%. |
| 24 mg | Bright | ≥90% | 205.2 | 1) placing for 7 days, stable, encapsulated efficiency ≥90%; 2) placing for 15 days, little precipitation, encapsulated efficiency ≤80%. |

2. Ginsenoside Rg5 Paclitaxel Liposome

Egg lecithin 30 mg, ginsenoside Rg5, paclitaxel 3 mg, soybean oil 15 mg and cholesterol 7.5 mg were added into ciency of the paclitaxel, the average particle size and the stability of the prepared ginsenoside Rg5 paclitaxel liposome are shown in the table below.

| The dosage of Rg5 | Appearance | Encapsulated efficiency (%) | Average particle size (nm) | Stability |
|---|---|---|---|---|
| 3 mg | Bright | ≥95% | 92.43 | 1) placing for 7 days, stable, encapsulated efficiency ≥90%; 2) placing for 15 days, stable, encapsulated efficiency ≥90%; 3) placing for 30 days, little precipitation, encapsulated efficiency ≤80%. |
| 6 mg | Bright | ≥95% | 103.5 | 1) placing for 7 days, stable, encapsulated efficiency ≥90%; 2) placing for 15 days, stable, encapsulated efficiency ≥90%; 3) placing for 30 days, little precipitation, encapsulated efficiency ≤80%. |
| 9 mg | Relatively bright | ≥98% | 115.1 | 1) placing for 7 days, stable, encapsulated efficiency ≥95%; 2) placing for 15 days, stable, encapsulated efficiency ≥90%; 3) placing for 30 days, little precipitation, encapsulated efficiency ≤80%. |
| 12 mg | Bright | ≥98% | 133.5 | 1) placing for 7 days, stable, encapsulated efficiency ≥90%; 2) placing for 15 days, stable, encapsulated efficiency ≥90%; 3) placing for 30 days, little precipitation, encapsulated efficiency ≤80%. |
| 15 mg | Bright | ≥90% | 138.7 | 1) placing for 7 days, stable, encapsulated efficiency ≥90%; 2) placing for 15 days, stable, encapsulated efficiency ≥80%; 3) placing for 30 days, little precipitation, encapsulated efficiency ≤80%. |
| 18 mg | Bright | ≥90% | 193.9 | 1) placing for 7 days, stable, encapsulated efficiency ≥90%; 2) placing for 15 days, little precipitation, encapsulated efficiency ≤80%. |
| 21 mg | Bright | ≥90% | 265.7 | 1) placing for 7 days, stable, encapsulated efficiency ≥90%; 2) placing for 15 days, little precipitation, encapsulated efficiency ≤80%. |
| 24 mg | Bright | ≥90% | 389.1 | 1) placing for 7 days, little precipitation, encapsulated efficiency ≤80%. |

3. Ginsenoside Rg3 Blank Liposome or Ginsenoside Rh2 Blank Liposome

The raw materials of the liposomes disclosed in CN201210151597.0 must contain cholesterol, i.e. ginsenoside Rg3: cholesterol=1:2.5; ginsenoside Rg3:phospholipid=1:10 to 1:20. However, when the mass of the ginsenoside Rg3 relative to 10% the mass of the egg lecithin, the encapsulated efficiency was less than 80%, which cannot meet the medicinal standards.

The ginsenoside Rg3 and the ginsenoside Rh2 in the following preparation methods were R configuration.

3.1. The preparation method:

Egg lecithin 30 mg, ginsenoside Rg3 or ginsenoside Rh2, and soybean oil 15 mg were added into 2 mL chloroform and stirred to form a clear solution at room temperature. The organic solvent was removed by a rotary evaporation in a thermostatic water bath at 40 to 50° C. to form a film, and 2 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg3 blank liposome or an aqueous solution containing ginsenoside Rh2 blank liposome. Then the aqueous solution was split charging into vials. The data of the dosage of the ginsenoside Rg3 or ginsenoside Rh2, the appearance, the average particle size and the stability of the prepared ginsenoside Rg3 blank liposome or ginsenoside Rh2 blank liposome are shown in the table below.

| The dosage of R-Rg3 or R-Rh2 | Appearance | Average particle size (nm) | Stability |
|---|---|---|---|
| 0.9 mg | Relatively the brightest | 356.4 | 1) placing for 7 days, little precipitation, encapsulated efficiency ≤80%. |
| 1.5 mg | Not very bright | 823.1 | 1) placing for 7 days, large amount of precipitation. |
| 2.4 mg-18 mg | Muddy | / | / |

3.2. The preparation method:

Egg lecithin 30 mg, ginsenoside Rg3 or ginsenoside Rh2, soybean oil 15 mg and cholesterol 7.5 mg were added into 2 mL chloroform and stirred to form a clear solution at room temperature. The organic solvent was removed by a rotary evaporation in a thermostatic water bath at 40 to 50° C. to form a film, and 2 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg3 blank liposome or an aqueous solution containing ginsenoside Rh2 blank liposome. Then the aqueous solution was split charging into vials. The data of the dosage of the ginsenoside Rg3 or ginsenoside Rh2, the appearance, the average particle size and the stability of the prepared ginsenoside Rg3 blank liposome or ginsenoside Rh2 blank liposome are shown in the table below.

were added into 2 mL chloroform and stirred to form a clear solution at room temperature. The organic solvent was removed by a rotary evaporation in a thermostatic water bath at 40 to 50° C. to form a film, and 2 mL 5% glucose aqueous solution (the percentage refers to the mass of the glucose relative to the total mass of the glucose aqueous solution) was added. An operation of ultrasound was carried out until the particle size of the liposome was between 0.1 and 0.3 micron. A 0.22 micron microporous membrane was used to filtration thereby obtaining an aqueous solution containing ginsenoside Rg3 paclitaxel liposome or an aqueous solution containing ginsenoside Rh2 paclitaxel liposome. Then the aqueous solution was split charging into vials. The data of the dosage of the ginsenoside Rg3 or ginsenoside Rh2, the appearance, the encapsulated efficiency of the paclitaxel, the average particle size and the stability of the prepared ginsenoside Rg3 paclitaxel liposome or ginsenoside Rh2 paclitaxel liposome are shown in the table below.

| The dosage of R-Rg3 or R-Rh2 | Appearance | Average particle size (nm) | Stability |
| --- | --- | --- | --- |
| 0.9 mg | Relatively the brightest | 105.2 | 1) placing for 7 days, stable, encapsulated efficiency ≥80%; 2) placing for 15 days, turning into not bright, little precipitation, encapsulated efficiency ≤80%. |
| 1.5 mg | Bright | 268.3 | 1) placing for 7 days, stable, encapsulated efficiency ≥90%; 2) placing for 15 days, turning into not bright, little precipitation, encapsulated efficiency ≤80%. |
| 2.4 mg | Bright | 635.4 | 1) placing for 7 days, stable, encapsulated efficiency ≥90%; 2) placing for 15 days, turning into not bright, little precipitation, encapsulated efficiency ≤80%. |
| 3 mg | Not very bright | ≥1 μm | 1) placing for 7 days, turning into not bright, little precipitation, encapsulated efficiency ≤80%. |
| 6 mg | Not bright | ≥1 μm | 1) placing for 7 days, large amount of precipitation. |
| 9 mg-18 mg | Muddy | / | / |

4. Ginsenoside Rg3 Paclitaxel Liposome or Ginsenoside Rh2 Paclitaxel Liposome

The preparation method:

Egg lecithin 30 mg, ginsenoside Rg3 or ginsenoside Rh2, paclitaxel 3 mg, soybean oil 15 mg and cholesterol 7.5 mg

| The dosage of R-Rg3 or R-Rh2 | Appearance | Encapsulated efficiency (%) | Average particle size (nm) | Stability |
| --- | --- | --- | --- | --- |
| 0.9 mg | Relatively the brightest | ≥80% | ≥1 μm | 1) placing for 7 days, little precipitation, encapsulated efficiency ≤80%. |
| 1.5 mg | Not very bright | ≤80% | ≥1 μm | 1) placing for 7 days, large amount of precipitation. |
| 2.4 mg-18 mg | Muddy | / | / | / |

While specific embodiments of the present invention are described above, those skilled in this field should understand that these are only illustrative, on condition of without departing from the principles and spirit of the present invention, various alterations or modifications can be made to these embodiments. Therefore, the scope of protection of the invention is defined by the appended claims.

What is claimed is:

1. A blank liposome having a membrane, wherein the membrane comprises lipid and a ginsenoside of Formula I:

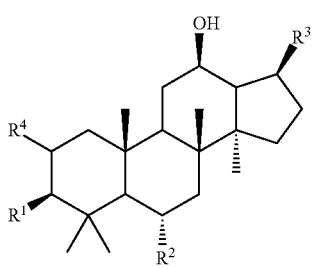

I wherein
each of $R^1$ and $R^2$ independently is H, OH, or $R^5$, and $R^1$ and $R^2$ are not both H at the same time;
$R^3$ is

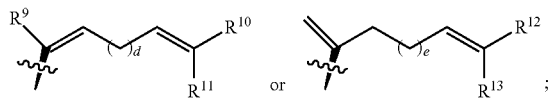

;

$R^4$ is H, OH, or $R^5$;
$R^5$ is $R^6$, $R^7$, or $R^8$;
$R^6$ is selected from the group consisting of: —O-Glc, —O-Rha, —O-Lyx, —O-Xyl, —O-Ara(p), —O-Ara (f), —O-Glc(2→1)Glc, —O-Glc(6→1)Glc, —O-Glc (2→1)Rha, —O-Glc(2→1)Xyl, —O-Glc(6→1)Xyl, —O-Glc(6→1)Rha, —O-Glc(2→1)Ara(p), —O-Glc (6→1)Ara(p), —O-Glc(2→1)Ara(f), —O-Glc(6→1) Ara(f), —O-Glc(2→1)Glc(2→1)Glc, —O-Glc(2→1) Glc(2→1)Xyl, —O-Glc(6→1)Glc(6→1)Xyl, —O-Glc (2→1)Glc(4→1)Xyl, —O-Glc(2→1)Lyx, —O-Glc (6→1)Lyx, —O-Glc(2→1)Glc(2→1)Rha, —O-Glc (2→1)Glc(2→1)Lyx, —O-Glc(2→1)Glc(2→1)Ara(f), —O-Glc(2→1)Glc(2→1)Ara(p), —O-Glc(2→1)Glc (6→1)Glc, —O-Glc(2→1)Glc(6→1)Rha, —O-Glc (2→1)Glc(6→1)Xyl, —O-Glc(2→1)Glc(6→1)Lyx, —O-Glc(2→1)Glc(6→1)Ara(f), —O-Glc(2→1)Glc (6→1)Ara(p), —O-Glc(6→1)Glc(2→1)Glc, —O-Glc (6→1)Glc(2→1)Rha, —O-Glc(6→1)Glc(2→1)Xyl, —O-Glc(6→1)Glc(2→1)Lyx, —O-Glc(6→1)Glc (2→1)Ara(f), —O-Glc(6→1)Glc(2→1)Ara(p), —O-Glc(6→1)Glc(6→1)Glc, —O-Glc(6→1)Glc (6→1)Rha, —O-Glc(6→1)Glc(6→1)Lyx, —O-Glc (6→1)Glc(6→1)Ara(f) or —O-Glc(6→1)Glc(6→1) Ara(p);
$R^7$ is a group formed by replacing one or more OH groups in $R^6$ with $R^8$ and each of the one or more than one $R^8$ groups independently can be the same as or different from each other;
$R^8$ is:
I) -mPEG, -Z-mPEG, -mPEO, -Z-PEO, -mPVP, —Z-PVP, -mEPEG, or -Z-EPEG, wherein m is H, alkyl, or acyl;

Z is -CO(CH$_2$)$_a$CO—, —NH(CH$_2$)$_a$CO—, —NH (CH$_2$)$_b$X—, or —CO—Ar—CH$_2$—; X is O, S, or NH; a is 1, 2, 3, 4, 5, 6, 7, or 8; and b is 1, 2, 3, 4, 5, 6, 7, 8, 9, or 10; or
II) $C_{4-22}$ aliphatic acyl, a phosphate group, a succinic acid ester group, a n-butyl acid ester group, a sulfonate group, a malic acid ester group, or a sodium sulfate salt; or
III) a group formed by dehydrogenizing the carboxyl contained in Boc-glycine, Boc-alanine, Boc-arginine, Boc-lysine, Boc-serine, Acetyl phenylalanine, Acetyl-proline, Asparagine, Aspartic acid, Cysteine, Glutamine, Glutamic acid, Histidine, Isoleucine, Leucine, Methionine, Phenylalanine, Proline, Threonine, Tryptophan, Tyrosine, or Valine; or
IV) —O-PEO, —O—PVP, —O-PEG, —O-MPEG, —O-EPEG, —O-Glc (2→1)Glc(6→1)Mal or —O-Glc (2→1)Glc(6→1)Ac;
each of $R^9$, $R^{10}$, $R^{11}$, $R^{12}$ and $R^{13}$, independently, is $C_{1-3}$ alkyl;
each of d and e, independently, is 1, 2, or 3; and
the ginsenoside of Formula I can be optionally modified by replacing one or more OH groups therein with one or more $R^8$ groups, and each of the $R^8$ replacement groups (when 2 or more) independently can be the same as or different from each other.

2. The blank liposome of claim 1, wherein the ginsenoside comprises ginsenoside Rg5, ginsenoside Rg6, ginsenoside Rk1, ginsenoside Rk2, ginsenoside Rk3, ginsenoside Rk4, ginsenoside Rh3, ginsenoside Rh4, ginsenoside F4, ginsenoside Rs4, ginsenoside Rs5, ginsenoside Rs6, ginsenoside Rs7, notoginsenoside T5, damulin A, or damulin B.

3. The blank liposome of claim 1, wherein the lipid in the membrane comprises phospholipid; and the mass ratio of the phospholipid to the ginsenoside is in the range of 0.5:1 to 100:1, 0.5:1 to 20:1, or 0.5:1 to 2:1.

4. The blank liposome of claim 1, wherein the lipid in the membrane comprises phospholipid; the membrane further comprises cholesterol; the mass ratio of the phospholipid to the ginsenoside of Formula I in the membrane is in the range of 1:0.01 to 1:3, 1:0.05 to 1:0.9, or 1:0.1 to 1:0.9; and the mass ratio of the ginsenoside of Formula I to the cholesterol is in the range of 0.1:1 to 100:1, 0.5:1 to 10:1, or 1.5:1 to 6:1.

5. The blank liposome of claim 4, wherein the mass percentage of the ginsenoside of Formula I in the membrane is in the range of 0.01% to 80%, 10% to 80%, 10% to 40%, or 20% to 40%; the mass percentage of the phospholipid in the membrane is in the range of 5% to 99.9%, 10% to 70%, 30% to 70%, or 30% to 60%; and the mass percentage of the cholesterol in the membrane is lower than 50% or is in the range of 0.5% to 50%, 5% to 40%, or 5% to 30%.

6. The blank liposome of claim 3, further comprising and encapsulating within the membrane an antioxidant, a cryoprotectant, or soybean oil and/or sodium oleate, wherein the antioxidant's mass percentage in the blank liposome is no more than 25%, in the range of 0.001% to 15%, 0.01% to 10%, or 0.01% to 5%; the mass percentage of the cryoprotectant in the blank liposome is no more than 80% or is in the range of 0.5% to 60%, 5% to 60%, or 30% to 60%; and the mass percentage of soybean oil and/or sodium oleate in the blank liposome is in the range of 1% to 90%, 15% to 80%, 20% to 70%, 20% to 30%, or 60% to 70%.

7. The blank liposome of claim 3, wherein the phospholipid comprises a natural phospholipid, semisynthetic phospholipid, or fully synthetic phospholipid; the natural phospholipid comprises natural lecithin, soyabean lecithin, egg lecithin, or cephalin; the semisynthetic phospholipid or the fully synthetic phospholipid comprises a phospholipid of phosphatidylcholline, phosphatidylserine, phosphatidylinositol, a phospholipid of phosphatidylethanolamine, phosphatidylglycerol, dicetyl phosphate, a PEG-modified phospholipid, cholesterol succinate, or 1-palmitoyl-2-oleoyl-sn-glycero-3-phosphocholine; the phospholipid of phosphatidylcholline comprises hydrogenated soybean lecithin, dipalmitoyl phosphatidylcholine, distearoyl phosphatidylcholine, dimyristoyl phosphatidylcholine, dilauroyl phosphatidylcholine, dioleoyl phosphatidylcholine, phosphatidylcholine, single palmitoyl phosphatidylcholine, or glycerol phosphatidylcholine; the phospholipid of phosphatidylethanolamine comprises 1-palmitoyl-2-oleoyl phosphatidylethanolamine, dilauroyl phosphatidylethanolamine, dierucoyl phosphatidylethanolamine, dioleoyl phosphatidylethanolamine, distearoyl phosphatidylethanolamine, dipalmitoyl phosphatidylethanolamine, or dimyristoyl phosphatidylethanolamine; the PEG-modified phospholipid comprises phosphatidylethanolamine-PEG, dipalmitoyl phosphatidylethanolamine-PEG, distearoyl phosphatidylethanolamine-PEG, dioleoyl phosphatidylethanolamine-PEG, C8 ceramide-PEG, C16 ceramide-PEG, distearoyl phosphatidylethanolamine-PEG-succinyl, distearoyl phosphatidylethanolamine-PEG-carboxyl, distearoyl phosphatidylethanolamine-PEG-maleimide, distearoyl phosphatidylethanolamine-PEG-propionamide bis-mercaptopyridine, distearoyl phosphatidylethanolamine-PEG-cyanuric chloride, distearoyl phosphatidylethanolamine-PEG-amino, distearoyl phosphatidylethanolamine-PEG-biotin, distearoyl phosphatidylethanolamine-PEG-folate, distearoyl phosphatidylethanolamine-PEG-folate, dilauroyl phosphatidylethanolamine-PEG, distearoyl phosphatidylethanolamine-PEG-active ester, phosphatidylethanolamine-PEG-active ester, dipalmitoyl phosphatidylethanolamine-PEG-active ester, dilauroyl phosphatidylethanolamine-PEG-active ester, distearoyl phosphatidylethanolamine-PEG-maleimide, phosphatidylethanolamine-PEG-maleimide, dipalmitoyl phosphatidylethanolamine-PEG-maleimide, dilauroyl phosphatidylethanolamine-PEG-maleimide, distearoyl phosphatidylethanolamine-PEG-biotin, distearoyl phosphatidylethanolamine-PEG-fluorescein, distearoyl phosphatidylethanolamine-PEG-hydroxyl, distearoyl phosphatidylethanolamine-PEG-amino, phosphatidylethanolamine-PEG-amino, dipalmitoyl phosphatidylethanolamine-PEG-amino, dilauroyl phosphatidylethanolamine-PEG-amino, distearoyl phosphatidylethanolamine-PEG-carboxyl, phosphatidylethanolamine-PEG-carboxyl, dipalmitoyl phosphatidylethanolamine-PEG-carboxyl, dilauroyl phosphatidylethanolamine-PEG-carboxyl, distearoyl phosphatidylethanolamine-PEG-thiol, distearoyl phosphatidylethanolamine-PEG-silane, distearoyl phosphatidylethanolamine-PEG-azide, cholesterol-PEG, methoxyl-PEG-cholesterol, cholesterol-PEG-active ester, cholesterol-PEG-maleimide, cholesterol-PEG-biotin, cholesterol-PEG-fluorescein, cholesterol-PEG-carboxyl, cholesterol-PEG-amino, or cholesterol-PEG-thiol; the antioxidant comprises sodium metabisulfite, sodium thiosulfate, propyl gallate, ascorbic acid, α-tocopherol, α-hydroxy acid, flavonoid, a phenylpropanoid phenolic compound, vitamin E, vitamin C, fumaric acid, cysteine, methionine, butyl hydroxy anisole, butyl hydroxytoluene, thiodipropionic acid, sulfites, hydrosulphite, dithioaminobenzoic acid compounds, citric acid, malic acid, sorbitol, glycerol, propylene glycol, hydroquinone, hydroxycoumarin, ethanolamine, phosphoric acid, or phosphorous acid; the cryoprotectant comprises a glucide, a polyol, an amino acid, or a buffer reagent; the glucide comprises a monosaccharide, a disaccharide, or a polysaccharide; the monosaccharide comprises glucose, mannitol, xylitol, or sorbitol, the disaccharide comprises sucrose, lactose, maltose, or galactose, the polysaccharide comprises trehalose; the polyol comprises propanediol or glycerol; the amino acid comprises an α-amino acid selected from the group consisting of threonine, glycine, glutamic acid, arginine and histidine; the buffer reagent comprises a buffer solution of pH in the range of 3 to 10, or 5 to 7, the buffer solution comprises an ethanol-acetic acid buffer solution, a tris(hydroxymethyl)aminomethane buffer solution, a barbital buffer solution, a sodium formate buffer solution, a phthalate buffer solution, a citrate buffer solution, a citric acid-disodium hydrogen phosphate buffer solution, an ammonia-ammonium chloride buffer solution, a borax-calcium chloride buffer solution, an acetate buffer solution, an acetic acid-lithium salt buffer solution, an acetic acid-sodium acetate buffer solution, an acetic acid-ammonium acetate buffer solution, a phosphoric acid-triethylamine buffer solution, or a phosphate buffer solution.

8. The blank liposome of claim 1, further comprising and encapsulating within the membrane a surfactant, a heat-sensitive excipient, a pH sensitive material, or an ion additive; the surfactant comprises polyethylene glycol and/or polysorbate; the polyethylene glycol has a number-average molecular weight of 200 to 8000; and the polysorbate comprises polyoxyethylene sorbitan monolaurate, polyoxyethylene sorbitan monopalmitate, polyoxyethylene sorbitan monostearate, polyoxyethylene sorbitan trioleate, PEG-phosphatidylethanolamine, PEG-polylactic acid, polylysine-polyl(actic-co-glycolic acid), polyetherimide-polylactic acid, PEG-polycaprolactone, PEG-poly-(lactic-co-glycolic) acid, poloxamer 188, polyoxyethylene fatty acid ester, polyoxyethylene fatty acid ether, or polyoxyethylene methyl castor oil ether; the heat-sensitive excipient comprises a polymer, a drug, or a surfactant and brings heat-sensitivity to the liposome; the polymer comprises polyisoprene acrylamide, polyisoprene acrylic acid, polyphosphate, or poly phospholipid-amide copolymer; the drug comprises zedoary turmeric oil, elemene, or brucea javanica oil; the ion additive comprise a cationic additive or an anion additive; the cationic additive comprises octadecylamine; and the anion additive comprises phosphatidic acid or phosphatidylserine.

9. A process for preparing the blank liposome of at least one of claims 1 to 8, comprising a first method or a second method, wherein the first method or the blank liposome prepared thereby does not include a cryoprotectant, and the second method or the blank liposome prepared thereby includes a cryoprotectant;

the first method includes the steps of:
(1) mixing a lipid and a ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and
(2) removing the organic solvent of the clear solution obtained in step (1), filming, mixing the film with water optionally containing a hydrophilic antioxidant, a hydrophilic surfactant, a hydrophilic heat-sensitive excipient, a hydrophilic pH sensitive material, and/or a hydrophilic ion additive to obtain an aqueous mixture, filtering the mixture after an operation of ultrasound, high pressure homogenization or pushing through a membrane to obtain an aqueous solution containing a blank liposome, drying to get the blank liposome;

the second method includes the steps of:
(1) mixing a lipid and a ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and
(2) removing the organic solvent of the clear solution obtained in step (1), filming, mixing the film with an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, filtering the mixture after an operation of ultrasound, high pressure homogenization or pushing through a membrane to obtain an aqueous solution containing a blank liposome, drying to get the blank liposome;

wherein the lipid, the ginsenoside of Formula I, the cholesterol, the antioxidant, the soybean oil and/or sodium oleate, the cryoprotectant, the surfactant, the heat-sensitive excipient, the pH sensitive material, and the ion additive are as defined in claims 1 to 8; and the organic solvent comprises a nitrile solvent, a $C_{1-4}$ alcohol solvent, a ketone solvent, an alkane solvent, an ether solvent, a halogenated hydrocarbon solvent, a sulfoxide solvent, or an aldehyde solvent.

10. The process of claim 9, wherein the organic solvent comprises a $C_{1-4}$ alcohol solvent, a nitrile solvent, an ether solvent, or a halogenated hydrocarbon solvent; the nitrile solvent comprises acetonitrile; the $C_{1-4}$ alcohol solvent comprises methanol, ethanol, isopropanol, or n-butanol; the ether solvent comprises tetrahydrofuran or diethyl ether; the halogenated hydrocarbon solvent comprises chloroform or dichloromethane; the ketone solvent comprises acetone or butanone; the alkane solvent comprises petroleum ether; the ratio of the organic solvent's volumn to the total mass of the components dissolved in the organic solvent in step (1) of the first or second method is 5 to 20 mL/g; step (1) of the first or second method is carried out at the temperature of 0 to 80° C., 10 to 80° C., or 10 to 65° C.; in step (2) of the first or second method, removal of the organic solvent of the clear solution obtained in step (1) is conducted with a rotary evaporator or a membrane evaporator at the temperature of 25 to 80° C., in step (2) of the first or second method, the filtration is microporous membrane filtration, and the pore size of the microporous membrane preferably is 0.22 micron; and in step (2) of the second method, the aqueous cryoprotectant solution has a 5% to 10% mass percentage of the cryoprotectant;

in step (2) of the first or second method, a freeze dryer is used for drying.

11. A loaded liposome comprising a blank liposome of at least one of claims 1 to 8 and an active substance loaded to and encapsulating within the liposome's membrane, wherein the active substance comprises a drug, a cosmetically active substance, or a substance with healthcare function; and the liposome is a blank liposome of at least one of claims 1 to 8.

12. The loaded liposome of claim 11, wherein the drug comprises an antitumor drug, an antifungal drug, an antiviral drug, an antibiotic, a non-steroidal anti-inflammatory drug, a calcium ion antagonist, an immunosuppressive agent, an anesthetic, a cardiovascular or vasodilation drug, a gastrointestinal drug, an antidepressant drug, a biological agent, a polynucleotide, or an oligonucleotide (including ribonucleotides and deoxyrbonucleotides); the antitumor drug comprises paclitaxel, docetaxel, cabazitaxel, irinotecan hydrochloride, hydroxycamptothecin, aminocamptothecin, 7-ethyl-10-hydroxy camptothecin, topotecan hydrochloride, lurtotecan, topotecan, belotecan, cisplatin, carboplatin, oxaliplatin, nedaplatin, lobaplatin, satraplatin, miriplatin, amyl platinum, aroplatin, carmustine, chlorambucil, melphalan, harringtonine, homoharringtonine, triptolide, tacrolimus, daunorubicin, pingyangmycin, doxorubicin hydrochloride, idarubicin, fluorouracil, cytarabine, methotrexate, etoposide phosphate, desoxy-podophyllotoxin, huperzine-A, vinorelbine tartrate, vincristine sulfate, vinblastine sulfate, vinorelbine, vindesine sulfate, temozolomide, tegafur, cyclophosphamide, ifosfamide, dacarbazine, epothilone A, epothilone B, epothilone C, epothilone D, epothilone E, epothilone F, bortezomib, gemcitabine hydrochloride, fludarabine phosphate, capecitabine, decitabine, pemetrexed disodium, sorafenib, recombinant human interferon a2b, cytosine arabinoside, all trans retinoic acid, interleukin-2, etoposide, thymidylate synthase inhibitor, mitoxantrone, minoxidil, azithromycin, epirubicin hydrochloride, doxorubicin hydrochloride (adriamycin), amrubicin hydrochloride, 5-aminolevulinic acid, gefitinib, imatinib, erlotinib, sunitinib, dasatinib, lapatinib, axitinib, apatinib, nilotinib, bosutinib, vandetanib, telatinib, neratinib, canertinib, saracatinib, octenidine, sorafenib, icotinib, mubritinib, lestaurtinib, tandutinib, dovitinib, 3',5'-dipalmitotyl cyclocytidine, or curcumenol; the antifungal drug comprises amphotericin B, gentamicin, indomethacin, penicillin G, econazole nitrate, flucytosine, fluconazole, itraconazole, voriconazole, posaconazole, ravuconazole, caspofungin, micafungin, anidulafungin, cefpiramide sodium, cefotaxime sodium, ceftriaxone, cefoperazone, cefditoren pivoxil, cefoxitin sodium, cefalexin, cefuroxime sodium, cefixime, cefpodoxime, cefmenoxime, cefodizime, cefsulodin, cefazonam, ceftizoxime, cefetamet pivoxil, cefterampivoxil, ceftibuten, cefdinir, cefamandole, cefotiam, ceforanide, cefonicid, ceftazidime, cefradine, cefprozil, cefazolin sodium, cefadroxil, cephalothin, cefathiamidine, cefaloridine, cephacetrile, ceftezole, cefapirin, cefpirome, cefclidin, cefepime, fusidate sodium, florfenicol, or tigecycline; the antiviral drug comprises ribavirin, acyclovir, cytarabine, idoxuridine, acyclovir laurate, acyclovir palmitate, iododeoxyuridine, cyclocytidine, dipalmitoyl cyclocytidine, phosphoric acid formate, phosphoric acid acetate, cimetidine, dipyridamole, rifampin, isoniazid, praziquantel, doxycycline, saquinavir, indinavir, ritonavir, nelfinavir, amprenavir, tipranavir, BMS232632, lamivudine, zidovudine, didanosine, zalcitabine stavudine, abacavir, adefovirdipivoail, tenofovi, fluoro lamivudine, nevirapine, delavirdin, efavirens, interleukin-2, tilmicosin, or diclazuril; the antibiotic comprises penicillin, penicillin V, amoxicillin, ampicillin, oxacillin, cloxacillin, procaine penicillin, benzathine penicillin, piperacillin, mezlocillin, ticarcillin, azlocillin, mezlocillin, carbenicillin, sulbenicillin, furbucillin, nafcillin, dicloxacillin, pivampicillin, apalcillin, amoxicillin, pivmecillinam, methicillin, lenampicillin, fomidacillin, flucloxacillin, kanamycin, natamycin, mitomycin, amikacin, tylosin, verteporfin, cefpiramide sodium, netilmicin sulfate, azithromycin, ofloxacin, ciprofloxacin, enoxacin, lomefloxacin, pefloxacin, rufloxacin, sparfloxacin, fleroxacin, moxifloxacin, grepafloxacin, trovafloxacin, norfloxacin, gemifloxacin, gatifloxacin, tosufloxacin, pazufloxacin, sparfloxacin, clarithromycin, clindamycin, polymyxin, tobramycin, vancomycin, azithromycin, doxycycline, tetracycline, oxytetracycline, minocycline, aureomycin, guamecycline, demeclocycline, metacycline, etimicin, netilmicin, sisomicin, amikacin, arbekacin, dibekacin, aztreonam, meropenem, imipenem, thienamycin, panipenem, ertapenem, neomycin, paromomycin, or spectinomycin; the calcium ion antagonist comprises nimodipine, nifedipine, nicardipine, nitrendipine, verapamil, amlodipine, diltiazem, flunarizine, prenvlamine, gallopamil, or tiapamil; the non-steroidal anti-inflammatory drug comprises indomethacin, aspirin, paracetamol, naproxen, diclofenac, ibuprofen, nimesulide, rofecoxib, or celecoxib; the immunosuppressive agent comprises cyclosporin, alprostadil, cyclosporine, tacrolimus, rapamycin, mycophenolate mofetil, or mizoribine; the anesthetic comprises halothane, sevoflurane, isoflurane, enflurane, propofol, fentanyl, urethane, lidocaine, procaine, tetracaine, bupivacaine, pelltobarbitalum natricum, chloral hydrate, ketamine, morphine, or chloralose; the cardiovascular or vasodilation drug comprises dabigatran etexilate, alogliptin, polysaccharide sodium, ginkgolides, gingko flavonoid, *Ginkgo biloba* extract, asarone, olmesartan medoxomi, repaglinide, lipoic acid, breviscapine, urapidil, niacin, captopril, losartan, puerarin, tanshinone IIA, sarpogrelate hydrochloride, fluvastatin, pravastatin, simvastatin, lovastatin, simvastatin, mevastatin, cerivastatin, rosuvastatin, atorvastatin calcium, or rosuvastatin calcium; the gastrointestinal drug comprises omeprazole, lansoprazole, ilaprazole, pantoprazole, rabeprazole, terazosin, esomeprazole, tenatoprazole, leminoprazole, tenatoprazole, disuprazole, or lafutidine; the antidepressant drug comprises agomelatine, fluoxetine, paroxetine, duloxetine, sertraline, fluvoxamine, citalopram, escitalopram, venlafaxine, mirtazapine, imipramine, amitriptyline, clomipramine, doxepin, remeron, venlafaxime, phenelzine, isocarboxazid, or tranylcypromine, the polynucleotide or oligonucleotide comprises a fragment having genetic functions and consisting of the basic groups of such as A, T, C, G or U, the biological agent comprises a conventional mono-antibody drug, insulin, gamma globulin, antitoxic serum, interferon, interleukin, tumor necrosis factor, active factor of skin, epidermal growth factor, influenza vaccine, hepatitis A vaccine, cancer vaccine, recombinant human acidic fibroblast growth factor, or vascular endothelial growth factor 2 monoclonal antibody, the cosmetically active substance comprises ursolic acid, superoxide dismutase, biological protein T4N5, vitamin D2, methyl nicotinate, refined snake oil, hyaluronic acid, essential oil, or ceramide, the substance with healthcare function comprises glycyrrhizin, glycyrrhizic acid, disodiumglycyrrhizinate, methyl glycyrrhizinate, diammoniumglycyrrhizinate, vitamin E, resveratrol, coenzyme Q10, silymarin, anthocyanins, proanthocyanidins, lutein, folic acid, folinic acid, curcumin, emodin, tea polyphenols, epigallocatechin gallate, catechin, blueberry extract, glutathione, or oxymatrine.

13. The loaded liposome of claim 11, wherein the loaded liposome is in a form suitable for injection, lyophilized injection, oral administration, or topical administration.

14. The loaded liposome of claim 11, wherein the drug comprises paclitaxel, docetaxel, or irinotecan hydrochloride, the liposome comprises phospholipid and a ginsenoside of Formula I, the ginsenoiside comprises ginsenoside Rg5, and the mass ratio of the phospholipid to the ginsenoside Rg5 is in the range of 0.5:1 to 100:1, 0.5:1 to 20:1, or 0.5:1 to 4:1.

15. The loaded liposome of claim 14, wherein the liposome further comprises a cholesterol; the mass ratio of the phospholipid to ginsenoside Rg5 is in the range of 1:0.01 to 1:3, 1:0.05 to 1:0.9, or 1:0.1 to 1:0.9; and the mass ratio of ginsenoside Rg5 to the cholesterol is in the range of 0.1:1 to 100:1, 0.5:1 to 50:1, or 0.5:1 to 10:1.

16. The loaded liposome of claim 14, wherein the mass percentage of ginsenoside Rg5 in the blank liposome is in the range of 0.01% to 80%, 10% to 80%, 10% to 40%, or 20% to 40%; the mass percentage of the phospholipid in the blank liposome is in the range of 5% to 99.9%, 10% to 70%, 30% to 70%, or 30% to 60%; and the mass percentage of the cholesterol in the blank liposome is in the range of 0% to 50%, 0.5% to 50%, 5% to 40%, or 5% to 30%.

17. The loaded liposome of claim 14, further comprising and encapsulating within the liposome's membrane an antioxidant, a cryoprotectant, or soybean oil and/or sodium oleate; wherein the mass percentage of the antioxidant (when present) in the blank liposome is no more than 25% or is in the range of 0.001% to 15%, 0.01% to 10%, or 0.01% to 5%; the mass percentage of the cryoprotectant (when present) in the blank liposome is no more than 80% or is in the range of 0.5% to 60%, 5% to 60%, or 30% to 60%; and the mass percentage of the soybean oil and/or sodium oleate (when present) in the blank liposome is in the range of 1% to 90%, 15% to 80%, 20% to 70%, 20% to 30%, or 60% to 70%.

18. The loaded liposome of claim 17, wherein the phospholipid comprises soyabean lecithin, egg lecithin, or dimyristoyl phosphatidylcholine; the antioxidant comprises ascorbic acid, vitamin E, vitamin C, or threonine; the cryoprotectant comprises glucose, mannitol, xylitol, sucrose, lactose, trehalose, or propanediol.

19. A process for preparing a loaded liposome of claim 11, wherein when the liposome includes a cryoprotectant, the process for preparing the loaded liposome comprises any of Methods A, B, C, and D, wherein when the liposome does not contain or include a cryoprotectant, the process for preparing the loaded liposome comprises any one of Methods A1, B1, C1, and D1;

Method A comprises:
(1) mixing the lipid, the ginsenoside of Formula I, and the active substantive, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and
(2) removing the organic solvent of the clear solution obtained in step (1), filming, mixing the film with an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, filtering the mixture after an operation of ultrasound, high pressure homogenization of the mixture or pushing the mixture through a membrane to obtain an aqueous solution containing the liposome loaded with the active substance, drying to give the loaded liposome;

Method B comprises:
(1) mixing the lipid and the ginsenoside of Formula I, optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution; and
(2) removing the organic solvent of the clear solution obtained in step (1), filming, mixing the film with an active substance and an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a loaded liposome after an operation of ultrasound, high pressure homogenization of the mixture or pushing the mixture through a membrane, dialyzing and filtering to obtain an aqueous solution containing the liposome loaded with the active substance, drying to give the loaded liposome;

Method C comprises:
(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution in an organic solvent to obtain a clear solution, and
(2) removing the organic solvent of the clear solution obtained in step (1), filming, mixing the film with an aqueous solution containing ammonium sulfate and a cryoprotectant, and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a blank liposome after an operation of ultrasound, high pressure homogenization of the mixture or pushing the mixture through a membrane, dialyzing, then mixing with an active substance, filtering to obtain an aqueous solution containing a liposome loaded with the active substance, drying to give the loaded liposome;

Method D comprises:
(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and
(2) removing the organic solvent of the clear solution obtained in step (1), filming, mixing the film with citric acid and an aqueous solution containing a cryoprotectant and optionally a hydrophilic antioxidant, a hydrophilic surfactant, a hydrophilic heat-sensitive excipient, a hydrophilic pH sensitive material, and/or a hydrophilic ion additive to give a mixture, obtaining a solution of a blank liposome after an operation of ultrasound, high pressure homogenization of the mixture or pushing the mixture through a membrane, mixing the solution with an active substance and an aqueous solution of disodium hydrogen phosphate, filtering to obtain an aqueous solution containing a liposome loaded with the active substance, drying to give the loaded liposome;

Method A1 comprises
(1) mixing the lipid, the ginsenoside of Formula I and an active substantive, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and
(2) removing the organic solvent of the clear solution obtained in step (1), filming, mixing the film with water to obtain an aqueous mixture, optionally adding to the aqueous mixture a hydrophilic antioxidant, a hydrophilic surfactant, a hydrophilic heat-sensitive excipient, a hydrophilic pH sensitive material, and/or a hydrophilic ion additive, filtering the mixture after an operation of ultrasound, high pressure homogenization of the mixture or pushing the mixture through a membrane to obtain an aqueous solution containing a liposome loaded with the active substance, drying to give the loaded liposome;

Method B1 comprises:
(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and
(2) removing the organic solvent of the clear solution obtained in step (1), filming, mixing the film with an active substance and optionally an aqueous solution containing a hydrophilic antioxidant, a hydrophilic surfactant, a hydrophilic heat-sensitive excipient, a hydrophilic pH sensitive material, and/or a hydrophilic ion additive, obtaining a solution containing a liposome loaded with an active substance after an operation of ultrasound, high pressure homogenization or pushing through a membrane, dialyzing and filtering to obtain an aqueous solution containing the liposome loaded with the active substance, drying to give the loaded liposome;

Method C1 comprises:
(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution, and
(2) removing the organic solvent of the clear solution obtained in step (1), filming, mixing the film with an aqueous solution containing ammonium sulfate and optionally a hydrophilic antioxidant, a hydrophilic surfactant, a hydrophilic heat-sensitive excipient, a hydrophilic pH sensitive material, and/or a hydrophilic ion additive, obtaining a solution of a blank liposome after an operation of ultrasound, high pressure homogenization or pushing through a membrane, dialyzing, then mixing the solution with an active substance, filtering to obtain an aqueous solution containing a liposome loaded with the active substance, drying to give the loaded liposome;

Method D1 comprises:
(1) mixing the lipid and the ginsenoside of Formula I, and optionally, a cholesterol, a hydrophobic antioxidant, soybean oil and/or sodium oleate, a hydrophobic surfactant, a hydrophobic heat-sensitive excipient, a hydrophobic pH sensitive material, and/or a hydrophobic ion additive in an organic solvent to obtain a clear solution,
(2) removing the organic solvent of the clear solution obtained in step (1), filming, mixing the film with an aqueous solution containing citric acid and optionally a hydrophilic antioxidant, a hydrophilic surfactant, a hydrophilic heat-sensitive excipient, a hydrophilic pH sensitive material, and/or a hydrophilic ion additive, obtaining a solution of a blank liposome after an operation of ultrasound, high pressure homogenization or pushing through a membrane, then mixing the blank liposome solution with an active substance and an aqueous solution of disodium hydrogen phosphate, filtering to obtain an aqueous solution containing a liposome loaded with the active substance, drying to give the loaded liposome;
wherein in the method A, B, C, D, A1, B1, C1 or D1, each condition or parameter is as defined in claim 10; the mass ratio of the active substance to the ginsenoside of Formula I is 1:0.1 to 1:10 or 1:2 to 1:6; and the lipid, the ginsenoside of Formula I, the cholesterol, the antioxidant, the soybean oil and/or sodium oleate, the cryoprotectant, the surfactant, the heat-sensitive excipient, the pH sensitive material, the ion additive, and the active substantive are each as defined above in claims 1-10 and 11-18.

20. The process of claim 19, wherein in Method B, C, B1, or C1, the operation of dialysis comprises putting a blank liposome solution or a loaded liposome solution in an aqueous solution of glucose or pure water to give a mixed solution, and then dialyzing the mixed solution for 5 to 20 hours or for about 12 hours; or in Method B, C, B1 or C1, the operation of dialysis is carried out before the operation of ultrasound, high pressure homogenization or pushing through a membrane; or in Method C or C1, the mass fraction of the ammonium sulfate in the aqueous solution of ammonium sulfate and the cryoprotectant or the aqueous solution of ammonium sulfate is in the range of 1% to 15%, or of 6.6%; in Method C or C1, there comprises an operation of warm-keeping before filtering, for keeping the solution at 30° C. to 80° C. for 5 minutes to 1 hour; in Method D or D1, the mass concentration of citric acid in its aqueous solution is in the range of 1% to 15% or is about 5.76%, the mass concentration of disodium hydrogen phosphate in its aqueous solution is in the range of 5% to 20% or is about 7.1%; in Method D or D1, there comprises an operation of warm-keeping before filtering, the operation of warm-keeping preferably comprises keeping warm at 30° C. to 80° C. for 5 minutes to 1 hour; in Method A, B, C, D, A1, B1, C1 or D1, the active substance is used in the form of its aqueous solution or organic solution based on the active substance's lipid solubility or water solubility, and the active substance's mass volume percentage in the aqueous solution or the organic solution is in the range of 1% to 20%.

21. A process for preparing a loaded liposome of claim 11, comprising Method ①, Method ②, Method ③, Method ④, Method ⑤, or Method ⑥, wherein
Method ① comprises: adding soybean lecithin, ginsenoside Rg5 and paclitaxel into acetonitrile and stirring to form a clear solution; wherein a mass ratio of the soybean lecithin, ginsenoside Rg5 and paclitaxel is 10:6:3, a ratio of the volume of the acetonitrile to the mass of the ginsenoside Rg5 is 100 mL/3 g; removing the organic solvent in a thermostatic water bath at 50 to 60° C. to form a film, and adding purified water, a ratio of the volume of the purified water to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing protective gas, sealing to give the ginsenoside Rg5 paclitaxel liposome;
Method ② comprises: adding egg lecithin, ginsenoside Rg5, paclitaxel and threonine into methanol and stirring to form a clear solution, wherein a mass ratio of the egg lecithin, ginsenoside Rg5, paclitaxel, cholesterol and threonine is 13:12:4:5:5, a ratio of the volume of the methanol to the mass of the ginsenoside Rg5 is 100 mL/3 g, removing the organic solvent in a thermostatic water bath at 60 to 70° C. to form a film, and adding 5% glucose aqueous solution, a ratio of the volume of the glucose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing a protective gas, sealing to give the ginsenoside Rg5 paclitaxel liposome;
Method ③ comprises: adding egg lecithin, ginsenoside Rg5, paclitaxel, soybean oil and vitamin C into chloroform and stirring to form a clear solution, wherein a mass ratio of the egg lecithin, ginsenoside Rg5, paclitaxel, soybean oil and vitamin C is 8:6:1.5:4:0.5, a ratio of the volume of the chloroform to the mass of the ginsenoside Rg5 is 100 mL/3 g, the organic solvent is removed at 30 to 60° C. to form a film, and adding 10% trehalose aqueous solution, a ratio of the volume of the trehalose aqueous solution to the mass of the ginsenoside Rg5 is 100 mL/3 g, carrying out an operation of homogenization by a high pressure homogenizer until the particle size of the liposome is between 0.1 and 0.3 micron, filtering through a 0.22 micron microporous membrane thereby obtaining an aqueous solution containing ginsenoside Rg5 paclitaxel liposome, freeze drying the aqueous solution containing ginsenoside Rg5 paclitaxel liposome, introducing a protective gas, and sealing to give the ginsenoside Rg5 paclitaxel liposome;
Method ④ comprises: adding egg lecithin, ginsenoside Rg5, paclitaxel, soybean oil, cholesterol and vitamin E into chloroform and stirred to form a clear solution, wherein a mass ratio of the egg lecithin, ginsenoside Rg5, paclitaxel, soybean oil, cholesterol and vitamin E is 14:12:4:8:0.5:0.1, a ratio of the volume of the chloroform to the mass of the ginsenoside Rg5 is 100 mL/3 g, removing the organic solvent at 30 to 60° C. to form a film, and adding 5% saccharose aqueous solution, a ratio of the volume of the saccharose aqueous solution to the mass of the ginsenoside Rg5 is 100 mL/3 g, carrying out an operation of homogenization by a high pressure homogenizer until the particle size of the liposome is between 0.1 and 0.3 micron, filtering through a 0.22 micron microporous membrane thereby obtaining an aqueous solution containing ginsenoside Rg5 paclitaxel liposome, then freeze drying the aqueous solution containing ginsenoside Rg5 paclitaxel liposome, then introducing protective gas, sealing to give the ginsenoside Rg5 paclitaxel liposome;
Method ⑤ comprises: adding egg lecithin, ginsenoside Rg5, docetaxel, soybean oil, and vitamin C into chloroform and stirred to form a clear solution, wherein a mass ratio of the egg lecithin, ginsenoside Rg5, docetaxel, soybean oil, and vitamin C is 8:6:3:4:5, a ratio of the volume of the chloroform to the mass of the ginsenoside Rg5 is 100 mL/3 g, removing the organic solvent at 30 to 60° C. to form a film, and adding 10% trehalose aqueous solution, a ratio of the volume of the trehalose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane thereby obtaining an aqueous solution containing ginsenoside Rg5 docetaxel liposome, freeze drying the aqueous solution containing ginsenoside Rg5 docetaxel liposome, introducing protective gas, sealing to give the ginsenoside Rg5 docetaxel liposome;

Method ⑥ comprises: adding egg lecithin, ginsenoside Rg5, irinotecan hydrochloride and soybean oil into chloroform and stirring to form a clear solution, wherein a mass ratio of the egg lecithin, ginsenoside Rg5, irinotecan hydrochloride and soybean oil is 8:6:2:4:5, a ratio of the volume of the chloroform to the ginsenoside Rg5 is 100 mL/3 g, removing the organic solvent at 30 to 60° C. to form a film, and adding 10% trehalose aqueous solution, a ratio of the volume of the trehalose aqueous solution to the mass of the ginsenoside Rg5 is 100 mL/3 g, carrying out an operation of ultrasound until the particle size of the liposome is between 0.1 and 0.3 micron, filtering through a 0.22 micron microporous membrane to obtain an aqueous solution containing ginsenoside Rg5 docetaxel liposome, freeze drying the aqueous solution to contain ginsenoside Rg5 docetaxel liposome, introducing protective gas, and sealing to give the ginsenoside Rg5 docetaxel liposome.

\* \* \* \* \*